(12) United States Patent
Yongjun

(10) Patent No.: US 12,139,536 B2
(45) Date of Patent: Nov. 12, 2024

(54) GUIDED COMBINATIONAL THERAPEUTIC ANTIBODY

(71) Applicant: Antibody BioPharm, Inc., Clarksville, MD (US)

(72) Inventor: Guan Yongjun, Clarksville, MD (US)

(73) Assignee: Antibody Biopharm Inc.

( * ) Notice: Subject to any disclaimer, the term of this patent is extended or adjusted under 35 U.S.C. 154(b) by 0 days.

(21) Appl. No.: 16/619,769

(22) PCT Filed: Jun. 7, 2018

(86) PCT No.: PCT/US2018/036497
§ 371 (c)(1),
(2) Date: Dec. 5, 2019

(87) PCT Pub. No.: WO2018/226985
PCT Pub. Date: Dec. 13, 2018

(65) Prior Publication Data
US 2021/0332135 A1    Oct. 28, 2021

Related U.S. Application Data

(60) Provisional application No. 62/516,683, filed on Jun. 8, 2017.

(51) Int. Cl.
*C07K 16/28* (2006.01)
*C07K 16/32* (2006.01)

(52) U.S. Cl.
CPC .......... *C07K 16/2827* (2013.01); *C07K 16/32* (2013.01); *C07K 2317/31* (2013.01); *C07K 2317/92* (2013.01)

(58) Field of Classification Search
CPC ............ C07K 2317/30; C07K 2317/31; C07K 2317/92; C07K 2319/30
USPC ...................................................... 424/133.1
See application file for complete search history.

(56) References Cited

U.S. PATENT DOCUMENTS

| 11,059,909 B2 * | 7/2021 | Leusen | C07K 16/2803 |
| 11,091,562 B2 * | 8/2021 | Leusen | C07K 16/00 |
| 2016/0356600 A1 * | 12/2016 | Fan | G01C 21/3638 |
| 2023/0114801 A1 * | 4/2023 | Zhu | C07K 16/3007 530/387.3 |

FOREIGN PATENT DOCUMENTS

| CA | 3066074 | * | 6/2018 |
| NL | 2017270 B | * | 2/2018 |

OTHER PUBLICATIONS

BerenbaumClin.Exp.Immunol.28:1-18(1977).*
BerenbaumPharmacol. Rev.41:93-141(1989)).*
Tallarida"DrugSynergismandDoseEffectAnalysis" Ed.Chapman &Hall(2000),pp. 1-13and57-71.*
Castoldi et al (Protein Eng, Design, & Selection 25(10):551-559 (2012).*
Almagro & Franssen, (Frontiers in Bioscience, 13:1619-33 (2008)).*
Edwards et al., (J Mol Biol 334:103-118 (2003)).*
Marchalonis et al., (Dev & Comp Immunol. 30:223-247 (2006)).*
Lippow et al., "Computational design of antibody-affinity improvement beyond in vivo maturation," Nature Biotechnology, 25(10): 1171-1176 (2007).*
Sulea et al., "Application of Assisted Design of Antibody and Protein Therapeutics (ADAPT) improves efficacy of a Clostridium difficile toxin A single-domain antibody," Scientific Reports, 8(260): 1-11 (2018) ).*
Altshuler et al., "Generation of Recombinant Antibodies and Means for Increasing Their Affinity," Biochemistry (Moscow), 75(13): 1584-1605 (2010)).*
Vajda et al., "Progress toward improved understanding of antibody maturation," Current Opinion in Structural Biology, 67 pp. 226-231 (2021).*
Marks et al., "How repertoire data are changing antibody science," J. Biol. Chem. 295(29) 9823-9837 (2020).*
Akbar et al., Cell Reports 34, 108856, Mar. 16, 2021).*
Lo et al., "Conformational epitope matching and prediction based on protein surface spiral features," BMC Genomics vol. 22, Article No. 116 (2021).*
Hasegawa et al., "Single amino acid substitution in LC-CDR1 induces Russell body phenotype that attenuates cellular protein synthesis through eIF2a phosphorylation and thereby downregulates IgG secretion despite operational secretory pathway traffic," MABS, vol. 9, No. 5, pp. 854-873 (2017).*
Wu et al (Journal for ImmunoTherapy of Cancer, (Nov. 2022) vol. 10, Supp. Supplement 2, pp. A1349. Abstract No. 1301. Meeting Info: 37th Annual Meeting of the Society for Immunotherapy of Cancer's, SITC 2022. Boston, MA, United States. Nov. 8, 2022-Nov. 10, 2022.*
Rudman Toxicologic Pathology vol. 41, Issue 2, pp. 310-314 (Feb. 2013).*
Krah et al. (Immunopharmacology and Immunotoxicology, 38:1, 21-28 (2016)).*
Kim et al. (Biochimica et Biophysica Acta 1844 (2014) 1983-2001).*

* cited by examiner

*Primary Examiner* — Lynn A Bristol
(74) *Attorney, Agent, or Firm* — Xi Chen

(57) ABSTRACT

The present invention relates to multi-specific antibodies comprising fine tuned combination of low affinity single binding domain fragments to selectively target double targets on cancer cell, and use thereof for therapy, such as for guided immunotherapy.

6 Claims, 11 Drawing Sheets

Specification includes a Sequence Listing.

Bi-specific GCT Ab ABP366 and ABP336

ELISA Results for ABP366 Series Antibodies

Cell Surface staining Results for AbD066 Detected by Flow Cytometry

Cell Surface staining Results for AbD068-1
Detected by Flow Cytometry

ELISA Results for ABP336 Series Antibodies

Cell Surface staining Results for AbD036
Detected by Flow Cytometry

Cell Surface staining Results for AbD037 Detected by Flow Cytometry

GUIDED COMBINATIONAL THERAPEUTIC ANTIBODY

FIELD OF THE INVENTION

The present invention relates to novel bi-specific and multi-specific antibody comprising fine-tuned combination of single binding-domain fragments, and use thereof for therapy, such as for guided immunotherapy.

BACKGROUND OF THE INVENTION

Monoclonal antibodies (mAbs) have wide diagnostic and therapeutic potentials in clinical practices against cancer and other diseases. Monoclonal antibodies play a central role in cancer immunotherapy, either in naked forms, or as conjugates to cytotoxic agents, such as radioisotopes, drugs, toxins, or prodrug-converting enzymes. These approaches are under active evaluation, with different levels of developmental and clinical successes. Naked mAbs potentially may achieve clinical responses by inducing a cytotoxic effect upon binding to cell surface proteins that are overexpressed on cancer cells. Studies have shown that these therapeutic effects were accomplished by controlling diseases via neutralization of toxin or pathogen, programmed cell death (apoptosis), or by the induction of anti-target innate and active immune responses.

Because its unique features of specific targeting and mediating effector functions, antibody was explored as drug for targeting immunotherapy against diseases since the invention of monoclonal antibody technology by Cesar Milstein and Georges J. F. Kohler on 1975. There are currently more than 60 approved antibody-based biologic drugs with global annual sales of >$50 billion. The successful application of the current generation of antibody drugs has shaped the pharmaceutical industry and has been greatly improving public health. The development of optimal combinational therapies and innovative bi-specific antibodies, in addition to the development of antibody drugs against novel targets, are among the perspective future directions.

Therapeutic antibodies have been used in clinical applications for over twenty years. Currently, there are many anti-tumor antibody drugs in clinic, including Rituxan® (1997), Herceptin® (1998), Mylotarg® (2000), Campath® (2001), Zevalin® (2002), Bexxer® (2003), Avastin® (2004), Erbitux (2004), Vectibix® (2006), Arzerra® (2009); Benlysta® (2011); Yervoy® (2011), Adcetris® (2011), Perjeta® (2012), Kadcyla® (2013), Opdivo® (2014), Keytruda® (2014), Tecentriq® (2016). These antibodies target mainly EGFR, Her2, CD20 or VEGF, and more recently PD1 or PD-L1.

Bispecific antibodies are antibodies with dual epitope binding specificities, with one specificity being the capacity to bind a first epitope or target and a second specificity being the capacity to bind a second epitope or target.

Such bispecific antibodies are, in some embodiments, potentially valuable molecules for immunotherapy. For example, bispecific antibodies can crosslink cytotoxic effector cells to target cells, resulting in the killing of the target cell. Although numerous bispecific antibodies have been shown effective in vitro, few have been approved clinically as therapeutic agents. One bispecific antibody, Catumaxomab (trade name Removab) was approved in Europe in 2009. One of the reasons for the slow development of bispecific antibodies as therapeutic agents has been the difficulty in manufacturing them in sufficient purity and quantity.

Bispecific antibodies have been produced by chemical cross-linking, by hybrid-hybridomas or transfectomas, or by disulfide exchange at the hinge of two different Fab'. The first method yields heterogeneous and ill-defined products. The second method requires extensive purification of the bispecific antibodies from many hybrid-antibody side products, the presence of which may interfere with the cell cross-linking activity. The disulfide exchange method applies essentially only to F(ab')2, and is thus limited by the susceptibility of the monoclonal antibodies to cleavage by enzyme digestion. Further, since Fab' have little affinity for each other, very high protein concentrations are required for the formation of the inter-Fab' disulfide bonds. The disulfide exchange method has been improved by the use of Ellman's reagent to modify one of the Fab' prior to oxidation with the other Fab', reducing the incidence of homodimerization. However, even with this improvement, heterodimeric F(ab')2 can rarely be produced in better than 50% yield.

However, adverse safety issues, low response rate and limited effectiveness are general reality of the current antibody drugs. These disadvantages can be from off-target effect to normal tissues/cells because the antibody's epitope or target is in general from self antigen, inhibitory microenvironment for immune effector cells, unexpected Fc-mediated effector functions, etc. Thus, it remains a significant need for improved methods for efficiently producing bispecific antibodies and other similar compounds at high purity and with safer design.

SUMMARY OF THE INVENTION

In one aspect, the present invention provides an engineered bi-specific antibody, comprising: (i) a first chain comprising a first antigen binding domain which binds a first target, and having a first affinity about $10^{-5} \sim 10^{-8}$M; and (ii) a second chain comprising a second antigen binding domain which binds a second target, and having a second affinity about $10^{-5} \sim 10^{-8}$M; wherein said first antigen binding domain is linked to the N-terminal of the first constant heavy chain of said bi-specific antibody, wherein said second antigen binding domain is linked to the N-terminal of a light chain of said bi-specific antibody, wherein said first target and second target are both co-localized on a target cell; and wherein said bi-specific antibody preferably bind to said target cell than to cells only expressing either said first target or said second target, with an avidity about $10^{-9} \sim 10^{-12}$M.

In some aspect, the first target and second target is selected from a list comprising a tumor target, a disease-specific receptor, and an immune regulatory function target.

In some aspect, the tumor target is selected from a list comprising Her2, CEA, ROR2, TROP2, mGluR1, and EGFR.

In some aspect, the checkpoint receptor is selected from a list comprising PD-L1, CD47, LAG3, CD59 and Tim 3.

In some aspect, the light chain comprises any one of the sequences of Seq ID No. 1, Seq ID No. 2, Seq ID No. 3, Seq ID No. 4, Seq ID No. 5, Seq ID No. 6, Seq ID No. 7, Seq ID No. 8, Seq ID No. 9, Seq ID No. 10, Seq ID No. 11, Seq ID No. 12, Seq ID No. 30, Seq ID No. 31, Seq ID No. 34, Seq ID No. 35, Seq ID No. 38, Seq ID No. 39, Seq ID No. 42, and Seq ID No. 43.

In some aspect, the heavy chain of the above antibody comprises any one of the sequences of SEQ ID No. 1, No. 2, No. 3, No. 4, No. 36, No. 37, No. 40, No. 41; and the light chain of the above antibody comprises any one of the sequences of SEQ ID No. 5, No. 6, No. 7, No. 8, No. 38, No.

39, No. 42, No. 43, wherein said antibody binds to Her2 and CD47 double positive target cell.

In some aspect, the heavy chain of the above antibody comprises any one of the sequences of SEQ ID No. 5, No. 6, No. 7, No. 8, No. 28, No. 29, No. 32, No. 33; and the light chain of the above antibody comprises any one of the sequences of SEQ ID No. 9, No. 10, No. 11, No. 12, No. 30, No. 31, No. 34, No. 35, wherein said antibody binds to PD-L1 and CD47 double positive target cell.

In another aspect, the present invention provides an engineered tri-specific antibody, comprising: (i) a first chain comprising a first antigen binding domain that binds a first target, having a first affinity about $10^{-5}$~$10^{-8}$M; (ii) a second chain comprising a second antigen binding domain which binds a second target, having a second affinity about $10^{-5}$~$10^{-8}$M; and a third antigen binding domain which binds a third target, having a third affinity about $10^{-5}$~$10^{-8}$M; wherein said first antigen binding domain is linked to the N-terminal of the first constant heavy chain of said tri-specific antibody, wherein said second antigen binding domain is linked to the N-terminal of a light chain of said tri-specific antibody, wherein said first target and second target are both co-localized on a same target cell; and wherein said tri-specific antibody preferably bind to said target cell than to cells only expressing either said first target or said second target, with an avidity about $10^{-9}$~$10^{-12}$M, wherein said third antigen binding domain is linked to the c-terminal of the light chain of said tri-specific antibody; and wherein said third target is an effector function target or a regulatory factor; and wherein said third antigen binding domain preferably mediates effector cells or a regulatory factor to the target cell.

In some aspect, the first target and second target is selected from a list comprising a tumor target, a disease-specific receptor, and an immune regulatory function target.

In some aspect, the tumor target is selected from a list comprising Her2, CEA, ROR2, TROP2, mGluR1, and EGFR.

In some aspect, the checkpoint receptor is selected from a list comprising PD-L1, CD47, LAG3, CD59 and Tim 3.

In some aspect, the third target is selected from a list comprising CD3, CD16a, and CD59.

In some aspect, the heavy chain comprises any one of the sequences of Seq ID No. 1, Seq ID No. 2, Seq ID No. 3, Seq ID No. 4, Seq ID No. 5, Seq ID No. 6, Seq ID No. 7, Seq ID No. 8, Seq ID No. 9, Seq ID No. 10, Seq ID No. 11, Seq ID No. 2, Seq ID No. 28, Seq ID No. 29, Seq ID No. 32, Seq ID No. 33, Seq ID No. 36, Seq ID No. 37, Seq ID No. 40, Seq ID No. 41, Seq ID No. 60, Seq ID No. 61, Seq ID No. 66, Seq ID No. 67, Seq ID No. 68, and Seq ID No. 69.

In some aspect, the light chain comprises any one of the sequences of Seq ID No. 44, Seq ID No. 45, Seq ID No. 46, Seq ID No. 47, Seq ID No. 48, Seq ID No. 49, Seq ID No. 50, Seq ID No. 51, Seq ID No. 52, Seq ID No. 53, Seq ID No. 54, Seq ID No. 55, Seq ID No. 56, Seq ID No. 57, Seq ID No. 58, Seq ID No. 59, Seq ID No. 62, Seq ID No. 63, Seq ID No. 64, and Seq ID No. 65.

In some aspect, the heavy chain of the above antibody comprises any one of the sequences of SEQ ID No. 1, No. 2, No. 3, No. 4, No. 36, No. 37, No. 40, No. 41; and the light chain of the above antibody comprises any one of the sequences of SEQ ID No. 5, No. 6, No. 7, No. 8, No. 52, No. 53, No. 54, No. 55, No. 56, No. 57, No. 58, No. 59, wherein said antibody binds to Her2 and CD47 double positive target cell.

In some aspect, the heavy chain of the above antibody comprises any one of the sequences of SEQ ID No. 5, No. 6, No. 7, No. 8, No. 28, No. 29, No. 32, No. 33; and the light chain of the above antibody comprises any one of the sequences of SEQ ID No. 9, No. 10, No. 11, No. 12, No. 44, No. 45, No. 46, No. 47, No. 48, No. 49, No. 50, No. 51, wherein said antibody binds to PD-L1 and CD47 double positive target cell.

In another aspect, the present invention provides an antibody that is described above, for use in manufacture of medicament for treating cancer or a condition related thereto.

In another aspect, the present invention provides a method of treating cancer or a condition related thereto, comprising administering to a person, a therapeutically effective amount of the antibody that is described above.

In another aspect, the present invention provides a method for treating a subject in need of treatment using an antibody provided herein.

In some embodiments, the treatment results in a sustained response in the individual after cessation of the treatment.

In some embodiments, the immunotherapeutic is administered continuously, intermittently.

In some embodiments, the individual has colorectal cancer, melanoma, non-small cell lung cancer, ovarian cancer, breast cancer, pancreatic cancer, a hematological malignancy or renal cell carcinoma.

In some embodiments, wherein the antibody is administered intravenously, intramuscularly, subcutaneously, topically, orally, transdermally, intraperitoneally, intraorbitally, by implantation, by inhalation, intrathecally, intraventricularly, or intranasally.

In some embodiments, the therapeutic combination or pharmaceutical composition of the present invention further comprise an effective amount of an additional therapeutic agent, such as an anticancer agent.

In some embodiments, the anticancer agent is an antimetabolite, an inhibitor of topoisomerase I and II, an alkylating agent, a microtubule inhibitor, an antiandrogen agent, a GNRh modulator or mixtures thereof.

In some embodiments, the additional therapeutic agent is a chemotherapeutic agent selected from the group consisting of tamoxifen, raloxifene, anastrozole, exemestane, letrozole, imatinib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

In another aspect, the present invention provides a method for treating a disease condition in a subject that is in need of such treatment, comprising administering to the subject the therapeutic combination or pharmaceutical composition provided herein.

In some embodiments, the diseases condition is tumor. In some embodiments, the disease condition comprises abnormal cell proliferation.

In some embodiments, the abnormal cell proliferation comprises a pre-cancerous lesion. In some embodiments, the abnormal proliferation is of cancer cells.

In some embodiments, the cancer is selected from the group consisting of: breast cancer, colorectal cancer, diffuse large B-cell lymphoma, endometrial cancer, follicular lymphoma, gastric cancer, glioblastoma, head and neck cancer, hepatocellular cancer, lung cancer, melanoma, multiple myeloma, ovarian cancer, pancreatic cancer, prostate cancer, and renal cell carcinoma.

In a further aspect, the present invention provides a kit that contains the therapeutic combination provided herein, and optionally with an instruction.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
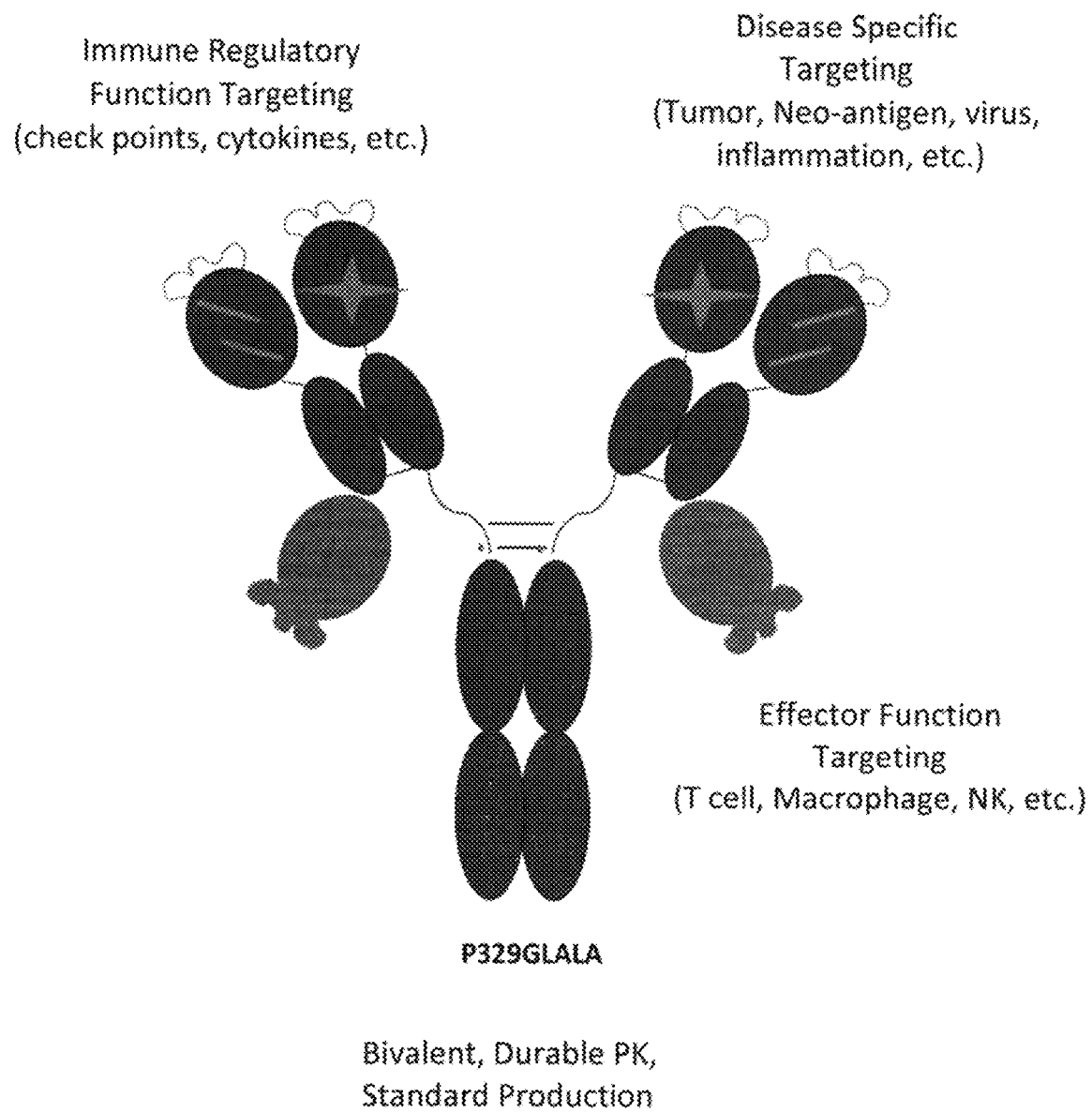
FIG. 1 depicts a Guided Combinational Therapeutic Antibody (GCT Ab). It has the following features: (1) safety fine-tuned affinity combination of pairs of binding domains; (2) Bi- and tri-specific antibody design with combination of synergistic targets and effector function; (3) bivalent nature for each of the multiple-functions targeting domain; and (4) defined Fc-region without unexpected detrimental effector function in a standard IgG antibody format with durable PK and standard production for a highly effective drug.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events.

Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

I. Definitions and Abbreviations

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well-known and commonly employed in the art. Standard techniques are used for nucleic acid and peptide synthesis. The techniques and procedures are generally performed according to conventional methods in the art and various general references, which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the disclosure.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The terms "polypeptide", "peptide", and "protein" are used interchangeably herein to designate a linear series of amino acid residues connected one to the other by peptide bonds, which includes proteins, polypeptides, oligopeptides, peptides, and fragments thereof. The protein may be made up of naturally occurring amino acids and/or synthetic (e.g. modified or non-naturally occurring) amino acids. Thus "amino acid", or "peptide residue", as used herein means both naturally occurring and synthetic amino acids. The terms "polypeptide", "peptide", and "protein" includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Furthermore, it should be noted that a dash at the beginning or end of an amino acid residue sequence indicates either a peptide bond to a further sequence of one or more amino acid residues or a covalent bond to a carboxyl or hydroxyl end group. However, the absence of a dash should not be taken to mean that such peptide bonds or covalent bond to a carboxyl or hydroxyl end group is not present, as it is conventional in representation of amino acid sequences to omit such.

By "nucleic acid" herein is meant either DNA or RNA, or molecules which contain deoxy- and/or ribonucleotides. Nucleic acid may be naturally occurring or synthetically made, and as such, includes analogs of naturally occurring polynucleotides in which one or more nucleotides are modified over naturally occurring nucleotides.

The terms "conjugated" and "joining" generally refer to a chemical linkage, either covalent or non-covalent that proximally associates one molecule with second molecule.

The term "isolated" is intended to mean that a compound is separated from all or some of the components that accompany it in nature. "Isolated" also refers to the state of a compound separated from all or some of the components that accompany it during manufacture (e.g., chemical synthesis, recombinant expression, culture medium, and the like).

The term "purified" is intended to mean a compound of interest has been separated from components that accompany it in nature or during manufacture and provided in an enriched form.

The "potent" or "potency" used in the context of a compound herein refers to ability or capacity of the compound to exhibit a desired activity.

The term "concentration" used in the context of a molecule such as peptide fragment refers to an amount of molecule present in a given volume. In some embodiments, a concentration of a molecule is given in a molar concentration where the number of moles of the molecules present in a given volume of solution is indicated.

The terms "antigen" and "epitope" interchangeably refer to the portion of a molecule (e.g., a polypeptide) which is specifically recognized by a component of the immune system, e.g., an antibody. As used herein, the term "antigen" encompasses antigenic epitopes, e.g., fragments of an antigen which are antigenic epitopes.

The term "antibody" encompasses polyclonal and monoclonal antibody where the antibody may be of any class of interest (e.g., IgG, IgM, and subclasses thereof), as well as hybrid antibodies, altered antibodies, F(ab')2 fragments, F(ab) molecules, Fv fragments, single chain fragment variable displayed on phage (scFv), single chain antibodies, single domain antibodies, diabodies, chimeric antibodies, humanized antibodies, and a fragment thereof. In some embodiments, the fragments of an antibody may be functional fragments which exhibit immunological binding properties of the parent antibody molecule. The antibodies described herein can be detectably labeled, e.g., with a radioisotope, an enzyme which generates a detectable product, a fluorescent protein, and the like. Detectable labels that find use in in vivo imaging are of interest. The antibodies may be further conjugated to other moieties, such as a cytotoxic molecule or other molecule, members of specific binding pairs, and the like.

A typical antibody structural unit, especially when it is in full length, is known to include a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains, respectively.

An "antigen-binding site" or "binding domain" refers to the part of an antibody molecule or fragment domain thereof that participates in antigen binding. The antigen binding site is formed by amino acid residues of the N-terminal variable heavy chain (VH) and variable light chain (VL). Three highly divergent stretches within the variable regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three-dimensional space to form an antigen binding "surface". This surface mediates recognition and binding of the target antigen. The three hypervariable regions of each of the heavy and light chains are referred to as "complementarity determining regions" or "CDRs". The CDRs are primarily responsible for binding to an epitope of an antigen. The "binding domain" is formed by fragment domain of a protein that form a stable subunit mediating in antigen binding or receptor/ligand interaction.

Antibody and fragments thereof according to the present disclosure encompass bispecific antibodies and fragments thereof. Bispecific antibodies may resemble single antibodies (or antibody fragments) but have two different antigen binding sites or domains. Bispecific antibodies may have binding specificities for at least two different epitopes. Bispecific antibodies and fragments can also be in form of heteroantibodies. Heteroantibodies are two or more antibodies, or antibody binding fragments (e.g., Fab) linked together, each antibody or fragment having a different specificity.

Antibody conjugates are also provided. The conjugates include any antibody of the present disclosure and an agent. The agent may be selected from a therapeutic agent, an imaging agent, a labeling agent, or an agent useful for therapeutic and/or labeling purposes.

The strength or affinity of immunological binding interactions between an antibody (or fragment thereof) and the specific antigen (or epitope) can be expressed in terms of the dissociation constant (Kn) of the interaction, wherein a smaller Kn represents a greater affinity. Immunological binding properties of selected polypeptides can be quantified using methods well known in the art. One such method entails measuring the rates of antigen binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of koff/kon enables cancellation of all parameters not related to affinity and is thus equal to the equilibrium dissociation constant $K_D$ (see, generally, Davies et al. Ann. Rev. Biochem. 1990, 59: 439-15 473).

The term "specific binding of an antibody" or "antigen-specific antibody" in the context of a characteristic of an antibody refers to the ability of an antibody to preferentially bind to a particular antigen that is present in a mixture of different antigens. In certain embodiments, a specific binding interaction will discriminate between desirable and undesirable antigens (or "target" and "non-target" antigens) in a sample, in some embodiments more than about 10 to 100-fold or more (e.g., more than about 1000- or 10,000-fold). In certain embodiments, the affinity between an antibody and antigen when they are specifically bound in an antibody antigen complex is characterized by a $K_D$ (dissociation constant) of less than $10^{-6}$M, less than $10^{-7}$ M, less than $10^{-8}$ M, less than $10^{-9}$ M, less than $10^{-9}$ M, less than $10^{-11}$M, or less than about $10^{-12}$M or less.

The term "monoclonal antibody" refers to an antibody composition having a homogeneous antibody population. The term encompasses whole antibody molecules, as well as Fab molecules, F(ab')2 fragments, Fv fragments, single chain fragment variable displayed on phage (scFv), fusion proteins comprising an antigen-binding portion of an antibody and a non-antibody protein, and other molecules that exhibit immunological binding properties of the parent monoclonal antibody molecule. Methods of making and screening polyclonal and monoclonal antibodies are known in the art.

The terms "derivative" and "variant" refer to without limitation any compound or antibody which has a structure or sequence derived from the compounds and antibodies of the present disclosure and whose structure/sequence is sufficiently similar to those disclosed herein and based upon that similarity, would be expected, by one skilled in the art, to exhibit the same or similar activities and utilities as the claimed and/or referenced compounds or antibody, thereby also interchangeably referred to "functional equivalent". Modifications to obtain "derivative" or "variant" includes, for example, by addition, deletion and/or substitution of one or more of the amino acid residues. The functional equivalent or fragment of the functional equivalent may have one or more conservative amino acid substitutions. The term "conservative amino acid substitution" refers to substitution of an amino acid to another amino acid that has similar properties to the original amino acid. The groups of conservative amino acids are known in the art.

Conservative substitutions may be introduced in any position of a preferred predetermined peptide or fragment thereof It may however also be desirable to introduce nonconservative substitutions, particularly, but not limited to, a non-conservative substitution in any one or more positions. A non-conservative substitution leading to the formation of a functionally equivalent fragment of the peptide would for example differ substantially in polarity, in electric charge, and/or in steric bulk while maintaining the functionality of the derivative or variant fragment.

"Percentage of sequence identity" is determined by comparing two optimally aligned sequences over a comparison window, wherein the portion of the polynucleotide or polypeptide sequence in the comparison window may have additions or deletions (i.e., gaps) as compared to the reference sequence (which does not have additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity" in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences or individual domains of the polypeptides), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 5 to 50 nucleotides or polypeptide sequences in length, or more preferably over a region that is 100 to 500 or 1000 or more nucleotides or polypeptide sequences in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full-length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) Adv. Appl. Math. 2:482, by the homology alignment algorithm of Needleman and Wunsch (1970) J Mol. Biol. 48:443, by the search for similarity method of Pearson and Lipman (1988) Proc. Natl. Acad Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J Mol. Biol. 215:403-410, respectively. Software for performing BLAST analyses is publicly available through the website of the National Center for Biotechnology Information.

"Cell(s) of interest" or "target cell(s)" used herein interchangeably refers to a cell or cells where one or more signaling pathways are intended to modulated. In some embodiments, the target cell(s) includes, but not limited to, a cancer cell(s). In some other embodiments, the target cell(s) includes immune effector cells such as natural killer cell(s), T cell(s), dendritic cell(s) and macrophage(s).

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage independent growth potential, ability to promote tumor growth and/or development in an immunocompromised non-human animal model, and/or any appropriate indicator of cellular transformation. "Cancer cell" may be used interchangeably herein with "tumor cell" or "cancerous cell", and encompasses cancer cells of a solid tumor, a semi-solid tumor, a primary tumor, a metastatic tumor, and the like.

By "treatment" in the context of disease or condition is meant that at least an amelioration of the symptoms associated with the condition afflicting an individual is achieved, where amelioration is used in a broad sense to refer to at least a reduction in the magnitude of a parameter, e.g. symptom, associated with the condition (e.g., cancer) being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus, treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells, or so as to protect against disease caused by bacterial infection, which protection can include elimination of detectable bacterial cells; and/or (iii) relief, that is, causing the regression of clinical symptoms.

The term "effective amount" of a composition as provided herein is intended to mean a non-lethal but sufficient amount of the composition to provide the desired utility. For instance, for eliciting a favorable response in a cell(s) of interest ("target cell(s)") such as modulating a signaling pathway, the effective amount of an (active, effective, potent or functional) antibody is the amount which results in notable and substantial change in the level of the activity of the signaling pathway, including downregulation and upregulation of the signaling pathway, when compared to use of no antibody or a control (inactive, ineffective, or non-functional) antibody. The measurement of changes in the level of the activity of the signaling pathway can be done by a variety of methods known in the art. In another example, for eliciting a favorable response in a subject to treat a disease (e.g., cancer), the effective amount is the amount which reduces, eliminates or diminishes the symptoms associated with the disorder, e.g., so as to provide for control of cancer metastasis, to eliminate cancer cells, and/or the like. As well be understood by a person having ordinary skill in the art, the exact amount required will vary from subject to subject, depending on the species, age, and general condition of the subject, the severity of the condition or disease that is being treated, the particular composition used, its mode of administration, and the like. Thus, it is not possible to specify an exact "effective amount." However, an appropriate effective amount may be determined by one of ordinary skill in the art using only routine experimentation.

The term "pharmaceutically acceptable excipient" as used herein refers to any suitable substance which provides a pharmaceutically acceptable compound for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

The terms "individual" or "subject" are intended to cover humans, mammals and other animals. The terms "individual" or "subject" are used interchangeably herein to refer to any mammalian subject to whom antibodies or fragments thereof in the present disclosure is subjected.

Certain embodiments feature a bispecific antibody, antigen binding fragment, or recombinant protein thereof, which is capable of modulating of the activity of one or more signaling pathway in a cell or cells of interest. The modulation of the one or more signaling pathway may lead to certain changes in target cell(s)'s behavior, such as stimulating or reducing cell proliferation, cell growth, cell differentiation, cell survival, cell secretion, modulation of adhesion and/or motility of cells.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto (e.g., phenol or hydroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

As used herein, the term "pharmaceutically acceptable carrier/excipient" includes any and all solvents, dispersion media, coatings, surfactants, antioxidants, preservatives (e.g., antibacterial agents, antifungal agents), isotonic agents, absorption delaying agents, salts, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except in so far as any conventional carrier is incompatible with the active ingredient, its use in the therapeutic or pharmaceutical compositions is contemplated.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "therapeutic combination" or "combination" refers to a combination of one or more active drug substances, i.e., compounds having a therapeutic utility. Typically, each such compound in the therapeutic combinations of the present invention will be present in a pharmaceutical composition comprising that compound and a pharmaceutically acceptable carrier. The compounds in a therapeutic combination of the present invention may be administered simultaneously or separately, as part of a regimen.

II. Compositions

In general, the present invention provides engineered bi-, tri-, and tetera-specific antibodies and compositions, engineered antibodies that recognize two, three, or four different cell surface antigens and design methods of generating such antibodies. The engineer antibodies of the present inventions comprise two single chain fragments, such as one light chain (domain 1 and CL) and one heavy chain (domain 2 and CH1), with each recognize a different antigen with relative low affinity, such as lower than $10^{-8}$M, and preferably $10^{-5}$M to $10^{-7}$M. The two chains are linked via the constant region of each chain, such as the linking of CL and CH1.

Although each single chain has low affinity, such as $10^{-5}$M to $10^{-8}$M, the combined affinity is much higher, such as $10^{-9}$M to $10^{-12}$M.

In one aspect, the instant invention provides an innovative multi-specific antibody drug platform of Guided Combinational Therapeutic Antibody (GCT Ab) that is aimed to greatly improve the safety, potency and effectiveness of antibody immunotherapies. As illustrated in FIG. 1, the invention includes features of: (1) minimalized off-target effect by bispecific antibody with selection of fine-tuned binding affinities of pairs of binding fragments against each target(s); (2) substantially improved potency by a novel tri-specific combination of antibody binding fragments against disease specific target, immune regulatory function target and defined effector function targeting; and (3) high effectiveness by novel design of an IgG format with multiple single domain binding fragments and bivalent nature of each binding domains together with durable PK and standard antibody production property.

Figure 2:
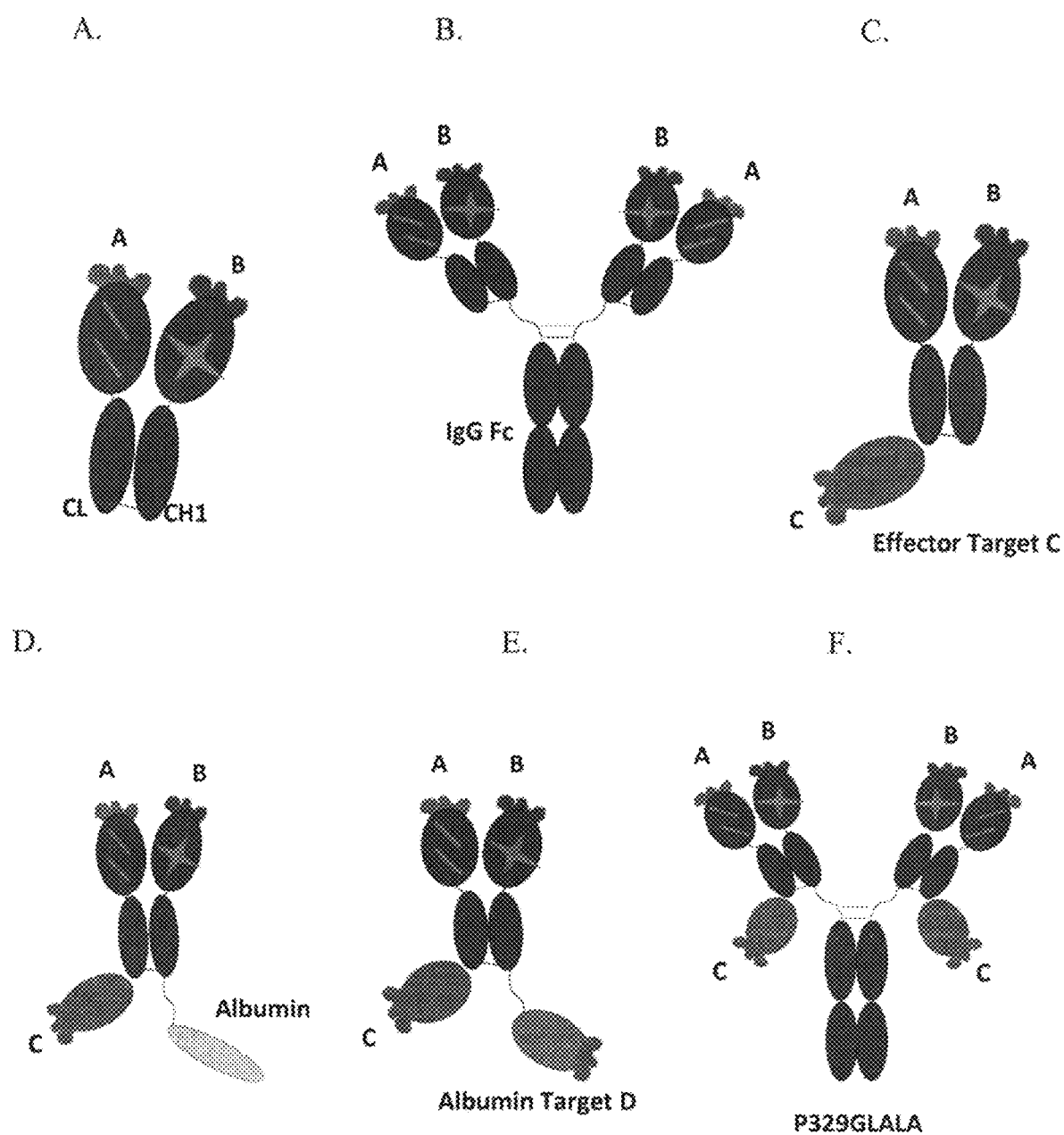
FIGS. 2A-F depict single binding domain based Fab and IgG antibody formats. A: Monovalent bi-specific antibody fragment. B: Double bivalent bi-specific antibody (DBB Ab). C: Monovalent tri-specific antibody fragment. D: Monovalent tetra-specific antibody fragment. E: Monovalent tri-specific antibody-albumin drug. F: Guided combinational therapeutic antibody (GCT Ab).

The design of safety fine-tuned binding affinities of a pair of antibody binding fragments against each target is selected to mimic a theory of human nature immune control mechanism on the interaction among the TCR complex and MHC complex. (Alberti, S. A high affinity T cell receptor? Immunology and cell biology 74, 292-297 (1996)). The affinity of TCR to a MHC-peptide is fine tuned during T cell development and maturation to a safe range that does not cause adverse interaction with normal MHC without foreign peptide and can effectively recognize specific MHC-peptide complex through synergistic binding effect from CD4/CD8 to MHC. Although the affinity of CD4/CD8 with MHC is in a low range $10^4$~$10^6$M$^{-1}$ (Davies, D. R., Padlan, E. A. & Sheriff, S. Antibody-antigen complexes. Annual review of biochemistry 59, 439-473 (1990)), and the affinity of TCR to MHC-peptide is in a low range $10^5$~$10^6$M$^{-1}$, (Matsui, K., et al. Low affinity interaction of peptide-MHC complexes with T cell receptors. Science 254, 1788-1791 (1991)). T cells can safely and effectively recognize specific MHC-peptide complex on target cells by synergistic binding. (Alberti, S. A high affinity T cell receptor? Immunology and cell biology 74, 292-297 (1996)). Disease specific targets are usually up-regulatory expressed self-proteins that may also present individually on normal cells at lower level. Highly affinity antibody may mediate off-target to normal cells and cause adverse effect. To employ the natural TCR/MHC safety control mechanism (FIG. 2A), our invention selects a pair of disease specific targets and a pair of binding domains to the targets with low individual affinities so that they will only loosely bind targets on normal tissue cells and can effectively bind disease targets through additive and/or synergistic effect in a format of bi-specific binding as illustrated in FIG. 2B.

In another aspect, the present invention provides an antibody comprise a controlled Fc-function design (e.g. P329G LALA-Fc (WO2012130831 A1)) that is devoid of all Fc-mediated effector functions to avoid potential uncontrolled/unexpected adverse effects4, while retain FcRn affinity for long half life (PK) and Protein A binding for standard production.

In another aspect, the present invention provides a novel tri-specific combination of antibody binding fragments against disease specific target, immune regulatory function target and defined effector function target to substantially improve drug's potency.

Figure 3A:
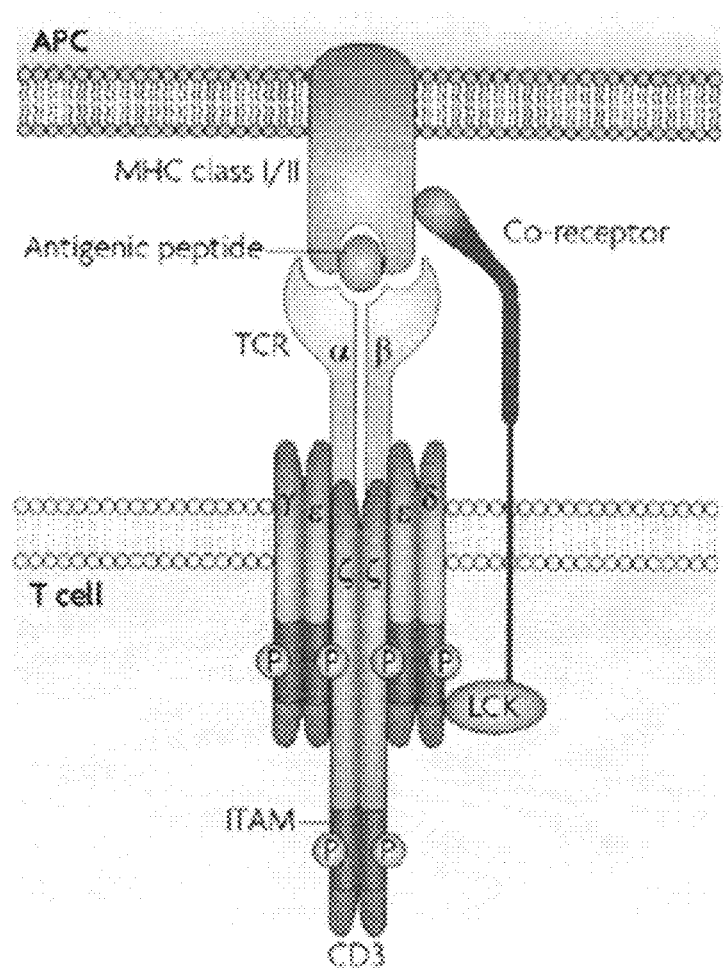
FIGS. 3A and 3B depict fine tuned affinity for safer specific targeting. 3A: Synergistic Binding of TCR and CD4/CD8 co-receptor with MHC-Peptide. 3B: Fine turned affinities for a pair of binding domains in GCT to safely mediate killing of tumor cell without affect normal cells.
Figure 3B:
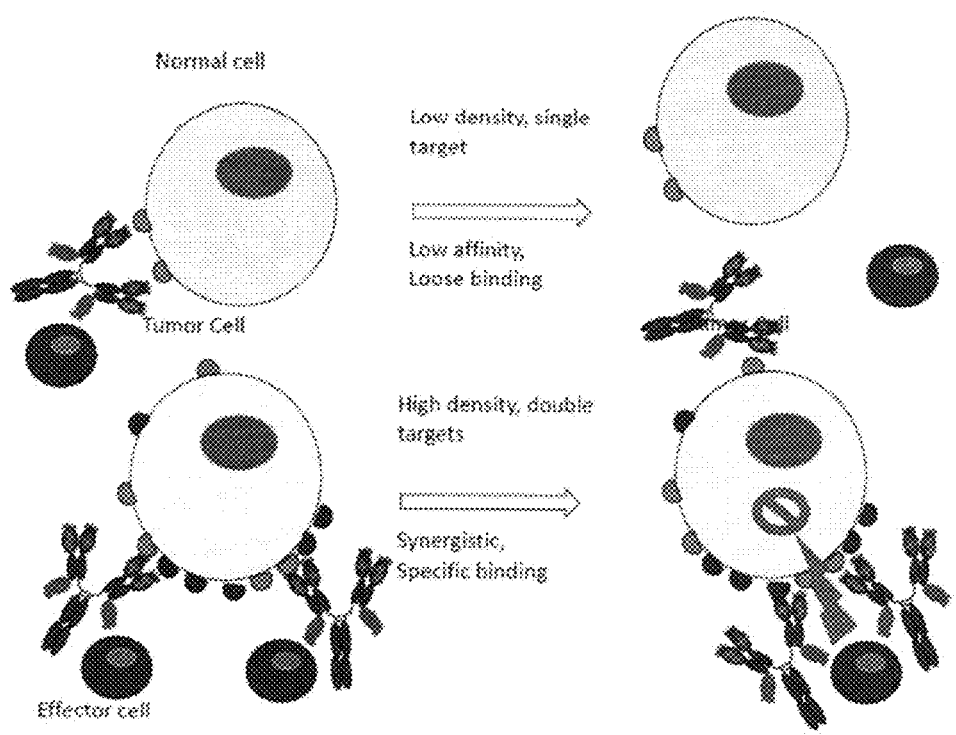

In a further aspect, the present invention provides a novel design of an antibody format with multiple single domain binding fragments and bivalent nature of each binding domains together with durable PK and standard antibody production property (FIGS. 1 and 3F). A pair of disease specific binding domains is individually linked to CH1 and CL with full function of each binding domains. This single binding domain based hi-specific antibody design could be alone used as a Fab form for a monovalent bi-specific antibody fragment or as a full IgG antibody form for a Double Bivalent Bi-specific antibody (DBB Ab) (FIGS. 3A and 3B). Further, a third binding domain for effector function targeting is linked at the C-terminus of CL to direct effector cells to the site of disease. This innovative Fab-like format of tri-specific antibody design could be used alone as an improved version of BiTE antibody in combination with check-point inhibitor (U.S. Pat. No. 9,315,567 B2 and WO2015095418 A1) (FIG. 3C) and could also be linked with a forth binding domain against albumin or directly linked with albumin at the C-terminus of CH1 (Patent WO1992001476 A1 and WO2010056550 A1) as a durable, highly effective antibody drug (FIGS. 3D and 3E). The use of full-length heavy chain with Fc in the design will dimerize the tri-specific antibody to the natural IgG bivalency for each of the three binding domains, which will greatly improve the drug's durability, productivity and effectiveness.

A. Single Binding Domain Based Fab and IgG Antibody Formats

The present invention provides various antibodies, such as Fab and IgG antibodies based on combination of single binding domains.

A1. Monovalent Bispecific Antibody

In one aspect, the present invention provides an engineered monovalent bispecific antibody, comprising: (i) a first chain comprising a first antigen binding single domain linked to the N-terminal of CH1 of Fab heavy chain that binds a first target and having a first affinity about $10^{4}$~$10^{-7}$M, and preferably $10^{-4}$~$10^{-6}$M; and (ii) a second chain comprising a second antigen binding single domain linked to the N-terminal of CL of light chain (kappa or lamda chain) that binds a second target, and having a second affinity about $10^{-4}$~$10^{-7}$M, and preferably $10^{-4}$~$10^{-6}$M.

In some embodiments, the engineered antibody only has two single chains, such as one light chain and one heavy chain, covalently linked after co-transfection of both genes in expression cassette into an expression cell system. One example is illustrated in FIG. 2A.

In general, the first antigen is a disease specific target, and the second antigen is an immune regulatory function target related to the same disease, as provided herein.

A2. Double Bivalent Bispecific Antibody

In another aspect, the present invention provides an engineered double bivalent bispecific (DBB) antibody, comprising (i) a first chain comprising a first antigen binding single domain linked to the N-terminal of CH1 of IgG heavy chain that binds a first target and having a first affinity about $10^{-5}$~$10^{-8}$M; (ii) a second chain comprising a second antigen binding single domain linked to the N-terminal of CL of light chain (kappa or lamda chain) that binds a second target, and having a second affinity about $10^{-5}$~$10^{-8}$M; (iii) a third chain that is same as the first chain and (iv) a fourth chain that is the same as the second chain, wherein said first chain is linked to said second chain to form a first arm, said third chain is linked to said fourth chain to form a second arm, and wherein said first arm is linked to second arm. The said first arm and said second arm is linked by the IgG Fc dimerization. One example is illustrated in FIG. 2B.

In some embodiments, the engineered antibody has total four chains, such as two light chain (each comprising one binding domain and one CL) and two heavy chains (each comprising one binding domain and one CH1). The two light chains have the same sequence, and the two heavy chains have the same sequence. Each of the light chain is linked to a heavy chain to form two arms. The two arms are linked to an Fc fragment, preferably IgG Fc fragment. The engineered antibody can be produced through common antibody production technologies in the art, which typically include steps of construction of expression cassette for the heavy and light chain genes, co-transfect the two genes into a suitable cell system to produce the recombinant antibody and to make a stable and high-productive cell clone, cell fermentation to produce cGMP final antibody product.

In general, the first antigen is a disease specific target, and the second antigen is an immune regulatory function target related to the same disease, as provided herein.

A3. Monovalent Tri-Specific Antibody

In another aspect, the present invention provides an engineered monovalent tri-specific antibody, comprising: (i) a first chain comprising a first antigen binding single domain linked to the N-terminal of CH1 of Fab heavy chain that binds a first target and having a first affinity about $10^{-5}$~$10^{-8}$M, preferably $10^{-5}$~$10^{-7}$M; (ii) a second chain comprising a second antigen binding single domain linked to the N-terminal of CL of light chain (kappa or lamda chain) that binds a second target, and having a second affinity about $10^{-5}$~$10^{-8}$M, preferably $10^{-5}$~$10^{-7}$M, as well as a third antigen binding single domain linked to the C-terminal of CL of light chain (kappa or lamda chain) that binds to a third antigen, and having a second affinity about $10^{-5}$~$10^{-7}$M. One example is illustrated in FIG. 2C.

In some embodiments, the engineered antibody only has two chains, such as one light chain and one heavy chain, covalently linked through the Fab constant region of CH1 and CL1.

In general, the first antigen is a disease specific target, the second antigen is an immune regulatory function target related to the same disease, and the third antigen is an effector function target.

A4. Monovalent Tetra-Specific Antibody

In one aspect, the present invention provides an engineered monovalent tetra-specific antibody, comprising: (i) a first chain comprising a first antigen binding single domain linked to the N-terminal of CH1 of Fab heavy chain that binds a first target, having a first affinity about $10^{-5}$~$10^{-8}$M; and a fourth antigen binding single domain linked to the C-terminal of CH1 of Fab heavy chain that binds a forth target, having a first affinity about $10^{-5}$~$10^{-7}$M (ii) a second chain comprising a second antigen binding single domain linked to the N-terminal of CL of light chain (kappa or lamda chain) that binds a second target, and having a second affinity about $10^{-5}$~$10^{-8}$M, as well as a third antigen binding single domain linked to the C-terminal of CL of light chain (kappa or lamda chain) that binds to a third antigen, and having a second affinity about $10^{-6}$~$10^{-7}$M. One example is illustrated in FIG. 2D.

In general, the first antigen is a disease specific target, the second antigen is an immune regulatory function target related to the disease, the third antigen is an effector function target, and the fourth antigen is fourth function target, such as albumin or other targets that, after binding, can safely extend the in vivo half life of the antibody.

A5. Monovalent Tri-Specific Antibody-Albumin Drug

In one aspect, the present invention provides an engineered monovalent tri-specific antibody-albumin conjugate, comprising: (i) a first chain comprising a first antigen binding single domain linked to the N-terminal of CH1 of Fab heavy chain that binds a first target, having a first affinity about $10^{-5}$~$10^{-8}$M; and an forth protein fragment linked to the C-terminal of CH1 of Fab heavy chain that can extend the in vivo half life of the fusion protein (ii) a second chain comprising a second antigen binding single domain linked to the N-terminal of CL of light chain (kappa or lamda chain) that binds a second target, and having a second affinity about $10^{-5}$~$10^{-8}$M, and (iii) a third antigen binding single domain linked to the C-terminal of CL of light chain (kappa or lamda chain) that binds to a third antigen, and having a second affinity about $10^{-5}$~$10^{-7}$M. One example is illustrated in FIG. 2E.

In general, the first antigen is a disease specific target, the second antigen is an immune regulatory function target related to the disease, the third antigen is an effector function target, and the fourth fragment that is albumin or other targets that, after binding, can safely extend the in vivo half life of the antibody.

A6. Guided Combinational Therapeutic Antibody (GCT Ab)

In one aspect, the present invention provides an engineered guided combinational therapeutic antibody, comprising (i) a first chain comprising a first antigen binding single domain linked to the N-terminal of CH1 of IgG heavy chain that binds a first target and having a first affinity about $10^{-5}$~$10^{-8}$M; (ii) a second chain comprising a second antigen binding single domain linked to the N-terminal of CL of light chain (kappa or lamda chain) that binds a second target, and having a second affinity about $10^{-5}$~$10^{-8}$M, as well as a third antigen binding single domain linked to the C-terminal of CL of light chain (kappa or lamda chain) that binds to a third antigen, and having a third affinity about $10^{-5}$~$10^{-7}$M. (iii) a third chain that is same as the first chain; (iv) a fourth chain that is the same as the second chain, wherein said first chain is linked to said second chain to form a first arm, said third chain is linked to said fourth chain to form a second arm, and wherein said first arm is linked to second arm. The said first arm and said second arm is linked by the IgG Fc dimerization; and (v) an modified Fc region that is devoid of all Fc-mediated effector functions except that of FcRn binding for long half life. One example is illustrated in FIG. 2F.

In general, the first antigen is a disease specific target, the second antigen is an immune regulatory function target related to the disease, the third antigen is an effector function target and the Fc if an IgG Fc containing P329G-LALA modifications In some embodiments, the first chain and the third chain have the same sequence.

In some embodiments, the first antigen binding domain and the third antigen binding domain have the same sequence.

In some embodiments, the second chain and the fourth chain have the same sequence.

In some embodiments, the second antigen binding domain and the fourth antigen binding domain chain have the same sequence.

In some embodiments, each of the first affinity, second affinity, third affinity, or fourth affinity, when applicable, is less than $10^{-8}$M, such as $10^{-5}$~$10^{-8}$M, and preferably about $10^{-5}$~$10^{-7}$M.

B. Disease Specific Target

In general, the first antigen is a disease specific target.

The disease specific target could be a tumor target (e.g Her2, Jamnani, F. R., et al. T cells expressing VHH-directed oligoclonal chimeric HER2 antigen receptors: towards tumor-directed oligoclonal T cell therapy. Biochimica et biophysica acta 1840, 378-386 (2014), Even-Desrumeaux, K., Fourquet, P., Secq, V., Baty, D. & Chames, P. Single-domain antibodies: a versatile and rich source of binders for breast cancer diagnostic approaches. Molecular bioSystems 8, 2385-2394 (2012)), neo-antigen (e.g. TRK (Patent publication U.S. Pat. No. 7,750,122 B2)), or disease-specific receptors (e.g. EGFR, see Patent WO2010037838 and Bell, A., et al. Differential tumor-targeting abilities of three single-domain antibody formats. Cancer letters 289, 81-90 (2010)).

In some embodiments, the disease specific target is selected from one of the disease markers, cytokines, or chemokines provided in Table 1, or the target list provided in Table 2.

TABLE 1

Target List

| Receptors | Cytokines | Chemokines | Disease Markers |
|---|---|---|---|
| PDL1 | IL-4 | CCL1 | HER2 |
| PDL2 | IL-16 | CCL2 | HER3 |
| CTLA4 | TGF beta | CCL3 | CEA |
| KIR | IL-1 | CCL4 | Muc-1 |
| IDO-1 | IL-6 | CCL5 | GPCR3 |
| 4-1BB | IL-10 | CCL6 | Alpha fetoprotein (AFP) |
| OX40L | IL-12 | CCL7 | CA15-3 |
| LAG3 | IL-18 | CCL8 | CA27-29 |
| CD47 | IL-17 | CCL9 | CA19-9 |
| CD80 | IL-15 | CCL10 | CA-125 |
| CD86 | IL13 | CCL11 | Calcitonin |
| B7RP1 | IL-23 | CCL12 | Calretinin |
| B7-H3 | IL21 | CCL13 | Carcinoembryonic antigen |

TABLE 1-continued

Target List

| Receptors | Cytokines | Chemokines | Disease Markers |
| --- | --- | --- | --- |
| HVEM | IL-32 | CCL14 | CD34 |
| CD137L | IL-9 | CCL15 | CD99MIC 2 |
| CD70 | IL28 | CCL16 | CD117 |
| GAL9 | Leptin | CCL17 | Chromogranin |
| CD4 | IL9 | CCL18 | TRK |
| TIM3 | IFN | CCL19 | Cytokeratin (various types: TPA, TPS, Cyfra21-1) |
| TIM4 | BAFF | CCL20 | Desmin |
| Adenosine receptor | Oncostatin | CCL21 | Epithelial membrane antigen (EMA) |
| TAM | VEGF | CCL22 | Factor VIII, CD31 FL1 |
| Vista | | CCL23 | Glial fibrillary acidic protein (GFAP) |
| BTLA | Type I IFNs | CCL24 | Gross cystic disease fluid protein (GCDFP-15) |
| HLA-G | TNF | CCL25 | HMB-45 |
| IDO-2 | RANKL | CCL26 | Human chorionic gonadotropin (hCG) |
| ARG1 | NGF | CCL27 | immunoglobulin |
| GCP3 | CSF | CCL28 | inhibin |
| Trop-2 | TNF-alpha | CXCL1 | keratin (various types) |
| Claudin | CD30L | CXCL2 | lymphocyte marker (various types |
| FOXO | CD40L | CXCL3 | MART-1 (Melan-A) |
| BCMA | CD27L | CXCL4 | Myo D1 |
| TRK | TNFSF10 | CXCL5 | muscle-specific actin (MSA) |
| EGFR | BMP | CXCL6 | neurofilament |
| GITR | GDF | CXCL7 | neuron-specific enolase (NSE) |
| PD1 | GDNF | CXCL8 | placental alkaline phosphatase (PLAP) |
| CD3 | | CXCL9 | prostate-specific antigen (PSA) |
| CD8 | | CXCL10 | PTPRC (CD45) |
| CD16 | | CXCL11 | S100 protein |
| CD19 | | CXCL12 | smooth muscle actin (SMA) |
| CD20 | | CXCL13 | synaptophysin |
| CD21 | | CXCL14 | thymidine kinase |
| CD22 | | CXCL15 | thyroglobulin (Tg) |
| CD23 | | CXCL16 | thyroid transcription factor-1 (TTF-1) |
| CD24 | | CXCL17 | Tumor M2-PK |
| CD27 | | FAM19 | vimentin |
| CD38 | | | CA-125 |
| CD40 | | | Epithelial tumor antigen (ETA) |
| CD32 | | | Tyrosinase |
| CD64 | | | Melanoma-associated antigen (MAGE) |
| CCR1 | | | abnormal products of ras, p53 |
| CCR2 | | | |
| CCR3 | | | |
| CCR4 | | | |
| CCR5 | | | |
| CCR6 | | | |
| CCR7 | | | |
| CCR8 | | | |
| CXCR1 | | | |
| CXCR2 | | | |
| CXCR3 | | | |
| CXCR4 | | | |
| CXCR5 | | | |
| CXCR6 | | | |
| CXCR7 | | | |
| CD116/GM-CSFR | | | |
| CD131/CSFR2B/JL3RB/IL5RB | | | |
| CD115/MCSF R/CSF1R | | | |
| CD114/G-CSFR | | | |
| BMP receptor | | | |
| GDNF receptor | | | |
| TGF-beta recepor | | | |
| FcRn | | | |
| DR | | | |
| IL6R | | | |
| IL | | | |
| GPCR | | | |
| MUC1 | | | |
| prostate stem cell antigen | | | |
| prostate membrane antigen | | | |
| Mesothelin | | | |

TABLE 2

| Entry | Protein names | Cross-reference (HGNC) | Cross-reference (CHEMBL) |
|---|---|---|---|
| P04229 | HLA class II histocompatibility antigen, DRB1 . . . | HGNC: 4948. HLA-DRB1. | CHEMBL1943. |
| P26439 | 3 beta-hydroxysteroid dehydrogenase/Delta 5-- . . . | HGNC: 5218. HSD3B2. | CHEMBL3670. |
| P08908 | 5-hydroxytryptamine receptor 1A | HGNC: 5286. HTR1A. | CHEMBL2096904. |
| P28222 | 5-hydroxytryptamine receptor 1B | HGNC: 5287. HTR1B. | CHEMBL2096904. |
| P28223 | 5-hydroxytryptamine receptor 2A | HGNC: 5293. HTR2A. | CHEMBL2095200. |
| P41595 | 5-hydroxytryptamine receptor 2B | HGNC: 5294. HTR2B. | CHEMBL1833. |
| P28335 | 5-hydroxytryptamine receptor 2C | HGNC: 5295. HTR2C. | CHEMBL2096904. |
| P46098 | 5-hydroxytryptamine receptor 3A | HGNC: 5297. HTR3A. | CHEMBL1899. |
| P01009 | Alpha-1-antitrypsin | HGNC: 8941. SERPINA1. | |
| P05067 | Amyloid beta A4 protein | HGNC: 620. APP. | CHEMBL2487. |
| O95342 | Bile salt export pump | HGNC: 42. ABCB11. | CHEMBL6020. |
| P00519 | Tyrosine-protein kinase ABL1 | HGNC: 76. ABL1. | CHEMBL2111414. |
| P42684 | Abelson tyrosine-protein kinase 2 | HGNC: 77. ABL2. | CHEMBL4014. |
| P22303 | Acetylcholinesterase | HGNC: 108. ACHE. | CHEMBL2095233. |
| P12821 | Angiotensin-converting enzyme | HGNC: 2707. ACE. | CHEMBL1808. |
| Q01718 | Adrenocorticotropic hormone receptor | HGNC: 6930. MC2R. | CHEMBL1965. |
| P08913 | Alpha-2A adrenergic receptor | HGNC: 281. ADRA2A. | CHEMBL1867. |
| P00813 | Adenosine deaminase | HGNC: 186. ADA. | CHEMBL1910. |
| P07550 | Beta-2 adrenergic receptor | HGNC: 286. ADRB2. | CHEMBL2096974. |
| P12235 | ADP/ATP translocase 1 | HGNC: 10990. SLC25A4. | |
| P14550 | Alcohol dehydrogenase [NADP(+)] | HGNC: 380. AKR1A1. | CHEMBL2246. |
| P02768 | Serum albumin | HGNC: 399. ALB. | CHEMBL3253. |
| P15121 | Aldose reductase | HGNC: 381. AKR1B1. | CHEMBL1900. |
| P04746 | Pancreatic alpha-amylase | HGNC: 477. AMY2A. | CHEMBL2045. |
| P54802 | Alpha-N-acetylglucosaminidase | HGNC: 7632. NAGLU. | |
| P10275 | Androgen receptor | HGNC: 644. AR. | CHEMBL1871. |
| Q5XXA6 | Anoctamin-1 | HGNC: 21625. ANO1. | CHEMBL2046267. |
| P01008 | Antithrombin-III | HGNC: 775. SERPINC1. | CHEMBL1950. |
| P21397 | Amine oxidase [flavin-containing] A | HGNC: 6833. MAOA. | CHEMBL1951. |
| P27338 | Amine oxidase [flavin-containing] B | HGNC: 6834. MAOB. | CHEMBL2095205. |
| P04114 | Apolipoprotein B-100 | HGNC: 603. APOB. | CHEMBL4549. |
| P05023 | Sodium/potassium-transporting ATPase subunit . . . | HGNC: 799. ATP1A1. | CHEMBL2095186. |
| P53004 | Biliverdin reductase A | HGNC: 1062. BLVRA. | |
| P15056 | Serine/threonine-protein kinase B-raf | HGNC: 1097. BRAF. | CHEMBL5145. |
| P15538 | Cytochrome P450 11B1, mitochondrial | HGNC: 2591. CYP11B1. | CHEMBL1908. |
| P09871 | Complement C1s subcomponent | HGNC: 1247. C1S. | CHEMBL3913. |
| Q13936 | Voltage-dependent L-type calcium channel subu . . . | HGNC: 1390. CACNA1C. | CHEMBL2095229. |
| P00918 | Carbonic anhydrase 2 | HGNC: 1373. CA2. | CHEMBL205. |
| P30988 | Calcitonin receptor | HGNC: 1440. CALCR. | CHEMBL2111189. |
| P41180 | Extracellular calcium-sensing receptor | HGNC: 1514. CASR. | CHEMBL1878. |
| P08185 | Corticosteroid-binding globulin | HGNC: 1540. SERPINA6. | CHEMBL2421. |
| P51681 | C-C chemokine receptor type 5 | HGNC: 1606. CCR5. | CHEMBL274. |
| P06126 | T-cell surface glycoprotein CD1a | HGNC: 1634. CD1A. | |
| P10747 | T-cell-specific surface glycoprotein CD28 | HGNC: 1653. CD28. | CHEMBL5191. |
| P06729 | T-cell surface antigen CD2 | HGNC: 1639. CD2. | CHEMBL2040. |
| P33681 | T-lymphocyte activation antigen CD80 | HGNC: 1700. CD80. | CHEMBL2364157. |
| P42081 | T-lymphocyte activation antigen CD86 | HGNC: 1705. CD86. | CHEMBL2364156. |
| P13569 | Cystic fibrosis transmembrane conductance reg . . . | HGNC: 1884. CFTR. | CHEMBL4051. |
| P06276 | Cholinesterase | HGNC: 983. BCHE. | CHEMBL2095233. |
| P51788 | Chloride channel protein 2 | HGNC: 2020. CLCN2. | CHEMBL1628478. |
| P01031 | Complement C5 | HGNC: 1331. C5. | CHEMBL2364163. |
| P21964 | Catechol O-methyltransferase | HGNC: 2228. COMT. | CHEMBL2023. |
| P05108 | Cholesterol side-chain cleavage enzyme, mitoc . . . | HGNC: 2590. CYP11A1. | CHEMBL2033. |
| P05093 | Steroid 17-alpha-hydroxylase/17,20 lyase | HGNC: 2593. CYP17A1. | CHEMBL3522. |
| P11511 | Cytochrome P450 19A1 | HGNC: 2594. CYP19A1. | CHEMBL1978. |
| P10635 | Cytochrome P450 2D6 | HGNC: 2625. CYP2D6. | CHEMBL289. |
| P08684 | Cytochrome P450 3A4 | HGNC: 2637. CYP3A4. | CHEMBL2364675. |
| P31327 | Carbamoyl-phosphate synthase [ammonia], mitoc . . . | HGNC: 2323. CPS1. | CHEMBL2362990. |
| P50416 | Carnitine O-palmitoyltransferase 1, liver iso . . . | HGNC: 2328. CPT1A. | CHEMBL1293194. |
| P07333 | Macrophage colony-stimulating factor 1 recept . . . | HGNC: 2433. CSF1R. | CHEMBL1844. |
| P15509 | Granulocyte-macrophage colony-stimulating fac . . . | HGNC: 2435. CSF2RA. | CHEMBL2364169. |
| Q99062 | Granulocyte colony-stimulating factor recepto . . . | HGNC: 2439. CSF3R. | CHEMBL1996. |
| P16410 | Cytotoxic T-lymphocyte protein 4 | HGNC: 2505. CTLA4. | CHEMBL2364164. |
| P61073 | C-X-C chemokine receptor type 4 | HGNC: 2561. CXCR4. | CHEMBL2107. |
| P11926 | Ornithine decarboxylase | HGNC: 8109. ODC1. | CHEMBL1869. |
| P20711 | Aromatic-L-amino-acid decarboxylase | HGNC: 2719. DDC. | CHEMBL1843. |
| P16444 | Dipeptidase 1 | HGNC: 3002. DPEP1. | CHEMBL1989. |
| P27487 | Dipeptidyl peptidase 4 | HGNC: 3009. DPP4. | CHEMBL2111469. |
| P14416 | D(2) dopamine receptor | HGNC: 3023. DRD2. | CHEMBL2111460. |
| P35462 | D(3) dopamine receptor | HGNC: 3024. DRD3. | CHEMBL2096905. |
| P00374 | Dihydrofolate reductase | HGNC: 2861. DHFR. | CHEMBL202. |
| P25101 | Endothelin-1 receptor | HGNC: 3179. EDNRA. | CHEMBL2096678. |
| P24530 | Endothelin B receptor | HGNC: 3180. EDNRB. | CHEMBL1785. |
| P00533 | Epidermal growth factor receptor | HGNC: 3236. EGFR. | CHEMBL2363049. |
| P08246 | Neutrophil elastase | HGNC: 3309. ELANE. | CHEMBL248. |
| P19235 | Erythropoietin receptor | HGNC: 3416. EPOR. | CHEMBL1817. |
| P04626 | Receptor tyrosine-protein kinase erbB-2 | HGNC: 3430. ERBB2. | CHEMBL1824. |

TABLE 2-continued

| Entry | Protein names | Cross-reference (HGNC) | Cross-reference (CHEMBL) |
|---|---|---|---|
| P03372 | Estrogen receptor | HGNC: 3467. ESR1. | CHEMBL2093866. |
| Q92731 | Estrogen receptor beta | HGNC: 3468. ESR2. | CHEMBL242. |
| P00742 | Coagulation factor X | HGNC: 3528. F10. | CHEMBL2111419. |
| P12259 | Coagulation factor V | HGNC: 3542. F5. | CHEMBL3618. |
| P00451 | Coagulation factor VIII | HGNC: 3546. F8. | CHEMBL3143. |
| P49327 | Fatty acid synthase | HGNC: 3594. FASN. | CHEMBL4158. |
| P12318 | Low affinity immunoglobulin gamma Fc region r . . . | HGNC: 3616. FCGR2A. | CHEMBL5841. |
| P21802 | Fibroblast growth factor receptor 2 | HGNC: 3689. FGFR2. | CHEMBL4142. |
| P36888 | Receptor-type tyrosine-protein kinase FLT3 | HGNC: 3765. FLT3. | CHEMBL1974. |
| Q04609 | Glutamate carboxypeptidase 2 | HGNC: 3788. FOLH1. | CHEMBL1892. |
| P14324 | Farnesyl pyrophosphate synthase | HGNC: 3631. FDPS. | CHEMBL1782. |
| P23945 | Follicle-stimulating hormone receptor | HGNC: 3969. FSHR. | CHEMBL2024. |
| P06241 | Tyrosine-protein kinase Fyn | HGNC: 4037. FYN. | CHEMBL1841. |
| P32239 | Gastrin/cholecystokinin type B receptor | HGNC: 1571. CCKBR. | CHEMBL298. |
| P04150 | Glucocorticoid receptor | HGNC: 7978. NR3C1. | CHEMBL2034. |
| P10912 | Growth hormone receptor | HGNC: 4263. GHR. | CHEMBL1976. |
| P43220 | Glucagon-like peptide 1 receptor | HGNC: 4324. GLP1R. | CHEMBL1784. |
| P30968 | Gonadotropin-releasing hormone receptor | HGNC: 4421. GNRHR. | CHEMBL1855. |
| P69905 | Hemoglobin subunit alpha | HGNC: 4823. HBA1. HGNC: 4824. HBA2. | CHEMBL2095168. |
| P68871 | Hemoglobin subunit beta | HGNC: 4827. HBB. | CHEMBL4331. |
| Q13547 | Histone deacetylase 1 | HGNC: 4852. HDAC1. | CHEMBL2093865. |
| P13716 | Delta-aminolevulinic acid dehydratase | HGNC: 395. ALAD. | CHEMBL3126. |
| P22830 | Ferrochelatase, mitochondrial | HGNC: 3647. FECH. | |
| P05546 | Heparin cofactor 2 | HGNC: 4838. SERPIND1. | |
| P04035 | 3-hydroxy-3-methylglutaryl-coenzyme A reducta . . . | HGNC: 5006. HMGCR. | CHEMBL402. |
| P50135 | Histamine N-methyltransferase | HGNC: 5028. HNMT. | CHEMBL2190. |
| Q9Y251 | Heparanase | HGNC: 5164. HPSE. | CHEMBL3921. |
| P35367 | Histamine H1 receptor | HGNC: 5182. HRH1. | CHEMBL231. |
| P11142 | Heat shock cognate 71 kDa protein | HGNC: 5241. HSPA8. | CHEMBL1275223. |
| P14735 | Insulin-degrading enzyme | HGNC: 5381. IDE. | CHEMBL1293287. |
| P08069 | Insulin-like growth factor 1 receptor | HGNC: 5465. IGF1R. | CHEMBL1957. |
| P01584 | Interleukin-1 beta | HGNC: 5992. IL1B. | CHEMBL1909490. |
| P14778 | Interleukin-1 receptor type 1 | HGNC: 5993. IL1R1. | CHEMBL1959. |
| Q9NPF7 | Interleukin-23 subunit alpha | HGNC: 15488. IL23A. | CHEMBL2364154. |
| P01589 | Interleukin-2 receptor subunit alpha | HGNC: 6008. IL2RA. | CHEMBL2364167. |
| P08887 | Interleukin-6 receptor subunit alpha | HGNC: 6019. IL6R. | CHEMBL2364155. |
| P40189 | Interleukin-6 receptor subunit beta | HGNC: 6021. IL6ST. | |
| P20839 | Inosine-5'-monophosphate dehydrogenase 1 | HGNC: 6052. IMPDH1. | CHEMBL1822. |
| P12268 | Inosine-5'-monophosphate dehydrogenase 2 | HGNC: 6053. IMPDH2. | CHEMBL2002. |
| P17181 | Interferon alpha/beta receptor 1 | HGNC: 5432. IFNAR1. | CHEMBL1887. |
| P48551 | Interferon alpha/beta receptor 2 | HGNC: 5433. IFNAR2. | CHEMBL2364170. |
| P06213 | Insulin receptor | HGNC: 6091. INSR. | CHEMBL1981. |
| P48544 | G protein-activated inward rectifier potassiu . . . | HGNC: 6266. KCNJ5. | |
| P13612 | Integrin alpha-4 | HGNC: 6140. ITGA4. | CHEMBL1907599. |
| P20701 | Integrin alpha-L | HGNC: 6148. ITGAL. | CHEMBL2096661. |
| Q14643 | Inositol 1,4,5-trisphosphate receptor type 1 | HGNC: 6180. ITPR1. | CHEMBL2111451. |
| P52333 | Tyrosine-protein kinase JAK3 | HGNC: 6193. JAK3. | CHEMBL2148. |
| Q12791 | Calcium-activated potassium channel subunit a . . . | HGNC: 6284. KCNMA1. | CHEMBL4304. |
| Q12809 | Potassium voltage-gated channel subfamily H m . . . | HGNC: 6251. KCNH2. | CHEMBL2362996. |
| P51787 | Potassium voltage-gated channel subfamily KQT . . . | HGNC: 6294. KCNQ1. | CHEMBL2363063. |
| P10721 | Mast/stem cell growth factor receptor Kit | HGNC: 6342. KIT. | CHEMBL1936. |
| P03952 | Plasma kallikrein | HGNC: 6371. KLKB1. | CHEMBL2111419. |
| P06239 | Tyrosine-protein kinase Lck | HGNC: 6524. LCK. | CHEMBL258. |
| P06858 | Lipoprotein lipase | HGNC: 6677. LPL. | CHEMBL2060. |
| P09917 | Arachidonate 5-lipoxygenase | HGNC: 435. ALOX5. | CHEMBL2111402. |
| P22888 | Lutropin-choriogonadotropic hormone receptor | HGNC: 6585. LHCGR. | CHEMBL1854. |
| P08235 | Mineralocorticoid receptor | HGNC: 7979. NR3C2. | CHEMBL1994. |
| Q00987 | E3 ubiquitin-protein ligase Mdm2 | HGNC: 6973. MDM2. | CHEMBL5023. |
| P08581 | Hepatocyte growth factor receptor | HGNC: 7029. MET. | CHEMBL3717. |
| P22894 | Neutrophil collagenase | HGNC: 7175. MMP8. | CHEMBL4588. |
| Q02750 | Dual specificity mitogen-activated protein ki . . . | HGNC: 6840. MAP2K1. | CHEMBL2111351. |
| P36507 | Dual specificity mitogen-activated protein ki . . . | HGNC: 6842. MAP2K2. | CHEMBL2964. |
| P34949 | Mannose-6-phosphate isomerase | HGNC: 7216. MPI. | CHEMBL2758. |
| P33527 | Multidrug resistance-associated protein 1 | HGNC: 51. ABCC1. | CHEMBL3004. |
| P42345 | Serine/threonine-protein kinase mTOR | HGNC: 3942. MTOR. | CHEMBL2221341. |
| P22033 | Methylmalonyl-CoA mutase, mitochondrial | HGNC: 7526. MUT. | |
| P08473 | Neprilysin | HGNC: 7154. MME. | CHEMBL1944. |
| P25103 | Substance-P receptor | HGNC: 11526. TACR1. | CHEMBL249. |
| P35228 | Nitric oxide synthase, inducible | HGNC: 7873. NOS2. | CHEMBL2096621. |
| Q9UHC9 | Niemann-Pick C1-like protein 1 | HGNC: 7898. NPC1L1. | CHEMBL2027. |
| Q96RI1 | Bile acid receptor | HGNC: 7967. NR1H4. | CHEMBL2047. |
| P04629 | High affinity nerve growth factor receptor | HGNC: 8031. NTRK1. | CHEMBL2815. |
| P03886 | NADH-ubiquinone oxidoreductase chain 1 | HGNC: 7455. MT-ND1. | CHEMBL2363065. |
| P03891 | NADH-ubiquinone oxidoreductase chain 2 | HGNC: 7456. MT-ND2. | CHEMBL2363065. |
| P41145 | Kappa-type opioid receptor | HGNC: 8154. OPRK1. | CHEMBL2095151. |
| P35372 | Mu-type opioid receptor | HGNC: 8156. OPRM1. | CHEMBL2095149. |

TABLE 2-continued

| Entry | Protein names | Cross-reference (HGNC) | Cross-reference (CHEMBL) |
|---|---|---|---|
| P09874 | Poly [ADP-ribose] polymerase 1 | HGNC: 270. PARP1. | CHEMBL3105. |
| P27815 | cAMP-specific 3',5'-cyclic phosphodiesterase . . . | HGNC: 8780. PDE4A. | CHEMBL2093863. |
| Q08499 | cAMP-specific 3',5'-cyclic phosphodiesterase . . . | HGNC: 8783. PDE4D. | CHEMBL2095153. |
| P07202 | Thyroid peroxidase | HGNC: 12015. TPO. | CHEMBL1839. |
| P00747 | Plasminogen | HGNC: 9071. PLG. | CHEMBL1801. |
| Q07869 | Peroxisome proliferator-activated receptor al . . . | HGNC: 9232. PPARA. | CHEMBL239. |
| P37231 | Peroxisome proliferator-activated receptor ga . . . | HGNC: 9236. PPARG. | CHEMBL2095162. |
| P05186 | Alkaline phosphatase, tissue-nonspecific isoz . . . | HGNC: 438. ALPL. | CHEMBL5979. |
| P62937 | Peptidyl-prolyl cis-trans isomerase A | HGNC: 9253. PPIA. | CHEMBL1949. |
| P23284 | Peptidyl-prolyl cis-trans isomerase B | HGNC: 9255. PPIB. | CHEMBL2075. |
| P06401 | Progesterone receptor | HGNC: 8910. PGR. | CHEMBL208. |
| P04070 | Vitamin K-dependent protein C | HGNC: 9451. PROC. | CHEMBL4444. |
| Q03431 | Parathyroid hormone/parathyroid hormone-relat . . . | HGNC: 9608. PTH1R. | CHEMBL1793. |
| Q13332 | Receptor-type tyrosine-protein phosphatase S | HGNC: 9681. PTPRS. | |
| P10276 | Retinoic acid receptor alpha | HGNC: 9864. RARA. | CHEMBL2363071. |
| P13631 | Retinoic acid receptor gamma | HGNC: 9866. RARG. | CHEMBL2363071. |
| P00797 | Renin | HGNC: 9958. REN. | CHEMBL286. |
| P07949 | Proto-oncogene tyrosine-protein kinase recept . . . | HGNC: 9967. RET. | CHEMBL2041. |
| P31350 | Ribonucleoside-diphosphate reductase subunit . . . | HGNC: 10452. RRM2. | CHEMBL1954. |
| P21817 | Ryanodine receptor 1 | HGNC: 10483. RYR1. | CHEMBL1846. |
| Q92736 | Ryanodine receptor 2 | HGNC: 10484. RYR2. | |
| P55017 | Solute carrier family 12 member 3 | HGNC: 10912. SLC12A3. | CHEMBL1876. |
| P21453 | Sphingosine 1-phosphate receptor 1 | HGNC: 3165. S1PR1. | CHEMBL4333. |
| Q4U2R8 | Solute carrier family 22 member 6 | HGNC: 10970. SLC22A6. | CHEMBL1641347. |
| Q01959 | Sodium-dependent dopamine transporter | HGNC: 11049. SLC6A3. | CHEMBL2363064. |
| P35498 | Sodium channel protein type 1 subunit alpha | HGNC: 10585. SCN1A. | CHEMBL2331043. |
| P35499 | Sodium channel protein type 4 subunit alpha | HGNC: 10591. SCN4A. | CHEMBL2331043. |
| Q14524 | Sodium channel protein type 5 subunit alpha | HGNC: 10593. SCN5A. | CHEMBL2331043. |
| Q15858 | Sodium channel protein type 9 subunit alpha | HGNC: 10597. SCN9A. | CHEMBL4296. |
| P37088 | Amiloride-sensitive sodium channel subunit al . . . | HGNC: 10599. SCNN1A. | CHEMBL1791. |
| Q99720 | Sigma non-opioid intracellular receptor 1 | HGNC: 8157. SIGMAR1. | CHEMBL287. |
| P12931 | Proto-oncogene tyrosine-protein kinase Src | HGNC: 11283. SRC. | CHEMBL2111336. |
| P51649 | Succinate-semialdehyde dehydrogenase, mitocho . . . | HGNC: 408. ALDH5A1. | CHEMBL1911. |
| P40763 | Signal transducer and activator of transcript . . . | HGNC: 11364. STAT3. | CHEMBL4026. |
| P21731 | Thromboxane A2 receptor | HGNC: 11608. TBXA2R. | CHEMBL2069. |
| P10827 | Thyroid hormone receptor alpha | HGNC: 11796. THRA. | CHEMBL2111462. |
| P00734 | Prothrombin | HGNC: 3535. F2. | CHEMBL2096988. |
| P01375 | Tumor necrosis factor | HGNC: 11892. TNF. | CHEMBL1825. |
| P63316 | Troponin C, slow skeletal and cardiac muscles | HGNC: 11943. TNNC1. | CHEMBL2095202. |
| P11387 | DNA topoisomerase 1 | HGNC: 11986. TOP1. | CHEMBL1781. |
| P11388 | DNA topoisomerase 2-alpha | HGNC: 11989. TOP2A. | CHEMBL1806. |
| Q02880 | DNA topoisomerase 2-beta | HGNC: 11990. TOP2B. | CHEMBL3396. |
| P40238 | Thrombopoietin receptor | HGNC: 7217. MPL. | CHEMBL1864. |
| Q16881 | Thioredoxin reductase 1, cytoplasmic | HGNC: 12437. TXNRD1. | CHEMBL2096978. |
| P16473 | Thyrotropin receptor | HGNC: 12373. TSHR. | CHEMBL1963. |
| P07101 | Tyrosine 3-monooxygenase | HGNC: 11782. TH. | CHEMBL1969. |
| P14679 | Tyrosinase | HGNC: 12442. TYR. | CHEMBL1973. |
| P04818 | Thymidylate synthase | HGNC: 12441. TYMS. | CHEMBL1952. |
| P30518 | Vasopressin V2 receptor | HGNC: 897. AVPR2. | CHEMBL1790. |
| P11473 | Vitamin D3 receptor | HGNC: 12679. VDR. | CHEMBL1977. |
| P15692 | Vascular endothelial growth factor A | HGNC: 12680. VEGFA. | CHEMBL1864. |
| P17948 | Vascular endothelial growth factor receptor 1 | HGNC: 3763. FLT1. | CHEMBL1868. |
| P35968 | Vascular endothelial growth factor receptor 2 | HGNC: 6307. KDR. | CHEMBL2111336. |
| P35916 | Vascular endothelial growth factor receptor 3 | HGNC: 3767. FLT4. | CHEMBL1955. |
| P38435 | Vitamin K-dependent gamma- carboxylase | HGNC: 4247. GGCX. | CHEMBL2012. |
| P07947 | Tyrosine-protein kinase Yes | HGNC: 12841. YES1. | CHEMBL2073. |
| P14060 | 3 beta-hydroxysteroid dehydrogenase/Delta 5-- . . . | HGNC: 5217. HSD3B1. | CHEMBL1958. |
| P28221 | 5-hydroxytryptamine receptor 1D | HGNC: 5289. HTR1D. | CHEMBL1983. |
| Q13639 | 5-hydroxytryptamine receptor 4 | HGNC: 5299. HTR4. | CHEMBL1875. |
| P30542 | Adenosine receptor A1 | HGNC: 262. ADORA1. | CHEMBL2096908. |
| P29274 | Adenosine receptor A2a | HGNC: 263. ADORA2A. | CHEMBL2096982. |
| P33765 | Adenosine receptor A3 | HGNC: 268. ADORA3. | CHEMBL2095195. |
| O00763 | Acetyl-CoA carboxylase 2 | HGNC: 85. ACACB. | CHEMBL4829. |
| Q15822 | Neuronal acetylcholine receptor subunit alpha . . . | HGNC: 1956. CHRNA2. | CHEMBL2109236. |
| P43681 | Neuronal acetylcholine receptor subunit alpha . . . | HGNC: 1958. CHRNA4. | CHEMBL1882. |
| P36544 | Neuronal acetylcholine receptor subunit alpha . . . | HGNC: 1960. CHRNA7. | CHEMBL2492. |
| P11229 | Muscarinic acetylcholine receptor M1 | HGNC: 1950. CHRM1. | CHEMBL2094109. |
| P08172 | Muscarinic acetylcholine receptor M2 | HGNC: 1951. CHRM2. | CHEMBL2094109. |
| P20309 | Muscarinic acetylcholine receptor M3 | HGNC: 1952. CHRM3. | CHEMBL245. |
| O00767 | Acyl-CoA desaturase | HGNC: 10571. SCD. | CHEMBL5555. |
| P35368 | Alpha-1B adrenergic receptor | HGNC: 278. ADRA1B. | CHEMBL2094251. |
| P25100 | Alpha-1D adrenergic receptor | HGNC: 280. ADRA1D. | CHEMBL2095203. |
| Q06278 | Aldehyde oxidase | HGNC: 553. AOX1. | CHEMBL3257. |
| P08588 | Beta-1 adrenergic receptor | HGNC: 285. ADRB1. | CHEMBL2331074. |
| P13945 | Beta-3 adrenergic receptor | HGNC: 288. ADRB3. | CHEMBL2097169. |
| P30556 | Type-1 angiotensin II receptor | HGNC: 336. AGTR1. | CHEMBL2094256. |
| P50052 | Type-2 angiotensin II receptor | HGNC: 338. AGTR2. | CHEMBL2094256. |

TABLE 2-continued

| Entry | Protein names | Cross-reference (HGNC) | Cross-reference (CHEMBL) |
|---|---|---|---|
| P16066 | Atrial natriuretic peptide receptor 1 | HGNC: 7943. NPR1. | CHEMBL1988. |
| P54289 | Voltage-dependent calcium channel subunit alp . . . | HGNC: 1399. CACNA2D1. | CHEMBL1919. |
| Q00975 | Voltage-dependent N-type calcium channel subu . . . | HGNC: 1389. CACNA1B. | CHEMBL2097170. |
| O43497 | Voltage-dependent T-type calcium channel subu . . . | HGNC: 1394. CACNA1G. | CHEMBL2362995. |
| O95180 | Voltage-dependent T-type calcium channel subu . . . | HGNC: 1395. CACNA1H. | CHEMBL2363032. |
| Q9P0X4 | Voltage-dependent T-type calcium channel subu . . . | HGNC: 1396. CACNA1I. | CHEMBL5558. |
| P49913 | Cathelicidin antimicrobial peptide | HGNC: 1472. CAMP. | |
| P11836 | B-lymphocyte antigen CD20 | HGNC: 7315. MS4A1. | CHEMBL2058. |
| P20273 | B-cell receptor CD22 | HGNC: 1643. CD22. | CHEMBL3218. |
| P20138 | Myeloid cell surface antigen CD33 | HGNC: 1659. CD33. | CHEMBL1842. |
| P07766 | T-cell surface glycoprotein CD3 epsilon chain | HGNC: 1674. CD3E. | CHEMBL2364168. |
| P31358 | CAMPATH-1 antigen | HGNC: 1804. CD52. | CHEMBL1912. |
| P40198 | Carcinoembryonic antigen-related cell adhesio . . . | HGNC: 1815. CEACAM3. | |
| Q9Y271 | Cysteinyl leukotriene receptor 1 | HGNC: 17451. CYSLTR1. | CHEMBL2094254. |
| P21554 | Cannabinoid receptor 1 | HGNC: 2159. CNR1. | CHEMBL2096981. |
| Q16850 | Lanosterol 14-alpha demethylase | HGNC: 2649. CYP51A1. | CHEMBL3849. |
| Q92523 | Carnitine O-palmitoyltransferase 1, muscle is . . . | HGNC: 2329. CPT1B. | CHEMBL2216739. |
| Q9HBH1 | Peptide deformylase, mitochondrial | HGNC: 30012. PDF. | CHEMBL4647. |
| Q96PD7 | Diacylglycerol O-acyltransferase 2 | HGNC: 16940. DGAT2. | CHEMBL5853. |
| P21728 | D(1A) dopamine receptor | HGNC: 3020. DRD1. | CHEMBL2096905. |
| P21918 | D(1B) dopamine receptor | HGNC: 3026. DRD5. | CHEMBL2096905. |
| Q14534 | Squalene monooxygenase | HGNC: 11279. SQLE. | CHEMBL3592. |
| O00519 | Fatty-acid amide hydrolase 1 | HGNC: 3553. FAAH. | CHEMBL2243. |
| P12319 | High affinity immunoglobulin epsilon receptor . . . | HGNC: 3609. FCER1A. | CHEMBL2248. |
| P30273 | High affinity immunoglobulin epsilon receptor . . . | HGNC: 3611. FCER1G. | |
| P14207 | Folate receptor beta | HGNC: 3793. FOLR2. | CHEMBL5064. |
| P80404 | 4-aminobutyrate aminotransferase, mitochondri . . . | HGNC: 23. ABAT. | CHEMBL2044. |
| P14867 | Gamma-aminobutyric acid receptor subunit alph . . . | HGNC: 4075. GABRA1. | CHEMBL2095172. |
| P47870 | Gamma-aminobutyric acid receptor subunit beta . . . | HGNC: 4082. GABRB2. | CHEMBL2093872. |
| P18507 | Gamma-aminobutyric acid receptor subunit gamm . . . | HGNC: 4087. GABRG2. | CHEMBL2094130. |
| Q02153 | Guanylate cyclase soluble subunit beta-1 | HGNC: 4687. GUCY1B3. | CHEMBL2111348. |
| Q02643 | Growth hormone-releasing hormone receptor | HGNC: 4266. GHRHR. | CHEMBL2032. |
| P47871 | Glucagon receptor | HGNC: 4192. GCGR. | CHEMBL1985. |
| P39086 | Glutamate receptor ionotropic, kainate 1 | HGNC: 4579. GRIK1. | CHEMBL2109241. |
| Q8TDS4 | Hydroxycarboxylic acid receptor 2 | HGNC: 24827. HCAR2. | CHEMBL3785. |
| P49019 | Hydroxycarboxylic acid receptor 3 | HGNC: 16824. HCAR3. | CHEMBL4421. |
| P25021 | Histamine H2 receptor | HGNC: 5183. HRH2. | CHEMBL1941. |
| Q14626 | Interleukin-11 receptor subunit alpha | HGNC: 5967. IL11RA. | CHEMBL2050. |
| P14902 | Indoleamine 2,3-dioxygenase 1 | HGNC: 6059. IDO1. | CHEMBL4685. |
| P29459 | Interleukin-12 subunit alpha | HGNC: 5969.1L12A. | CHEMBL2364153. |
| P14784 | Interleukin-2 receptor subunit beta | HGNC: 6009. IL2RB. | CHEMBL3276. |
| P15260 | Interferon gamma receptor 1 | HGNC: 5439. IFNGR1. | CHEMBL2364171. |
| P38484 | Interferon gamma receptor 2 | HGNC: 5440. IFNGR2. | CHEMBL2364171. |
| P49895 | Type I iodothyronine deiodinase | HGNC: 2883. DIO1. | CHEMBL2019. |
| P78508 | ATP-sensitive inward rectifier potassium chan . . . | HGNC: 6256. KCNJ10. | CHEMBL2146348. |
| Q14571 | Inositol 1,4,5-trisphosphate receptor type 2 | HGNC: 6181. ITPR2. | CHEMBL2111451. |
| Q14573 | Inositol 1,4,5-trisphosphate receptor type 3 | HGNC: 6182. ITPR3. | CHEMBL3904. |
| Q9UK17 | Potassium voltage-gated channel subfamily D m . . . | HGNC: 6239. KCND3. | CHEMBL1964. |
| O15554 | Intermediate conductance calcium- activated po . . . | HGNC: 6293. KCNN4. | CHEMBL4305. |
| P56696 | Potassium voltage-gated channel subfamily KQT . . . | HGNC: 6298. KCNQ4. | CHEMBL3576. |
| P07098 | Gastric triacylglycerol lipase | HGNC: 6622. LIPF. | CHEMBL1796. |
| O43451 | Maltase-glucoamylase, intestinal | HGNC: 7043. MGAM. | CHEMBL2074. |
| P20645 | Cation-dependent mannose-6-phosphate receptor | HGNC: 6752. M6PR. | CHEMBL5788. |
| Q12879 | Glutamate receptor ionotropic, NMDA 2A | HGNC: 4585. GRIN2A. | CHEMBL1972. |
| Q14994 | Nuclear receptor subfamily 1 group 1 member 3 | HGNC: 7969. NR1I3. | CHEMBL5503. |
| P03897 | NADH-ubiquinone oxidoreductase chain 3 | HGNC: 7458. MT-ND3. | CHEMBL2363065. |
| P41143 | Delta-type opioid receptor | HGNC: 8153. OPRD1. | CHEMBL2095149. |
| Q9H244 | P2Y purinoceptor 12 | HGNC: 18124.P2RY12. | CHEMBL2001. |
| P04054 | Phospholipase A2 | HGNC: 9030. PLA2G1B. | CHEMBL4426. |
| P54750 | Calcium/calmodulin-dependent 3',5'-cyclic nuc . . . | HGNC: 8774. PDE1A. | CHEMBL2363066. |
| Q01064 | Calcium/calmodulin-dependent 3',5'-cyclic nuc . . . | HGNC: 8775. PDE1B. | CHEMBL4425. |
| Q14123 | Calcium/calmodulin-dependent 3',5'-cyclic nuc . . . | HGNC: 8776. PDE1C. | CHEMBL2095150. |
| Q14432 | cGMP-inhibited 3',5'-cyclic phosphodiesterase . . . | HGNC: 8778. PDE3A. | CHEMBL2363066. |
| O76074 | cGMP-specific 3',5'-cyclic phosphodiesterase . . . | HGNC: 8784. PDE5A. | CHEMBL1341140. |
| P43088 | Prostaglandin F2-alpha receptor | HGNC: 9600. PTGFR. | CHEMBL1987. |
| P23219 | Prostaglandin G/H synthase 1 | HGNC: 9604. PTGS1. | CHEMBL2094253. |
| P35354 | Prostaglandin G/H synthase 2 | HGNC: 9605. PTGS2. | CHEMBL230. |
| P43119 | Prostacyclin receptor | HGNC: 9602. PTGIR. | CHEMBL1995. |
| Q02127 | Dihydroorotate dehydrogenase (quinone), mitoc . . . | HGNC: 2867. DHODH. | CHEMBL1966. |
| P08922 | Proto-oncogene tyrosine-protein kinase ROS | HGNC: 10261. ROS1. | CHEMBL5568. |
| Q15413 | Ryanodine receptor 3 | HGNC: 10485. RYR3. | CHEMBL2062. |
| P55011 | Solute carrier family 12 member 2 | HGNC: 10911. SLC12A2. | CHEMBL1615383. |
| Q9UGH3 | Solute carrier family 23 member 2 | HGNC: 10973. SLC23A2. | CHEMBL3271. |
| Q99808 | Equilibrative nucleoside transporter 1 | HGNC: 11003. SLC29A1. | CHEMBL1997. |
| Q9HAB3 | Solute carrier family 52, riboflavin transpor . . . | HGNC: 30224. SLC52A2. | |
| P23975 | Sodium-dependent noradrenaline transporter | HGNC: 11048. SLC6A2. | CHEMBL222. |
| Q9UI33 | Sodium channel protein type 11 subunit alpha | HGNC: 10583. SCN11A. | CHEMBL5167. |

TABLE 2-continued

| Entry | Protein names | Cross-reference (HGNC) | Cross-reference (CHEMBL) |
|---|---|---|---|
| P47872 | Secretin receptor | HGNC: 10608. SCTR. | CHEMBL1925. |
| Q99835 | Smoothened homolog | HGNC: 11119. SMO. | CHEMBL5971. |
| P61278 | Somatostatin | HGNC: 11329. SST. | CHEMBL1795130. |
| P60880 | Synaptosomal-associated protein 25 | HGNC: 11132. SNAP25. | CHEMBL2364159. |
| P30874 | Somatostatin receptor type 2 | HGNC: 11331. SSTR2. | CHEMBL1804. |
| P07437 | Tubulin beta chain | HGNC: 20778. TUBB. | CHEMBL5444. |
| Q9NYK1 | Toll-like receptor 7 | HGNC: 15631. TLR7. | CHEMBL2111471. |
| O14788 | Tumor necrosis factor ligand superfamily memb . . . | HGNC: 11926. TNFSF11. | CHEMBL2364162. |
| O75762 | Transient receptor potential cation channel s . . . | HGNC: 497. TRPA1. | CHEMBL6007. |
| Q7Z2W7 | Transient receptor potential cation channel s . . . | HGNC: 17961. TRPM8. | CHEMBL1075319. |
| P30536 | Translocator protein | HGNC: 1158. TSPO. | CHEMBL5742. |
| P37288 | Vasopressin V1a receptor | HGNC: 895. AVPR1A. | CHEMBL1889. |
| P23763 | Vesicle-associated membrane protein 1 | HGNC: 12642. VAMP1. | |
| P63027 | Vesicle-associated membrane protein 2 | HGNC: 12643. VAMP2. | CHEMBL2364160. |
| P38606 | V-type proton ATPase catalytic subunit A | HGNC: 851. ATP6V1A. | |
| P49765 | Vascular endothelial growth factor B | HGNC: 12681. VEGFB. | |
| Q9BQB6 | Vitamin K epoxide reductase complex subunit 1 | HGNC: 23663. VKORC1. | CHEMBL1930. |
| Q05940 | Synaptic vesicular amine transporter | HGNC: 10935. SLC18A2. | CHEMBL1893. |
| P47989 | Xanthine dehydrogenase/oxidase | HGNC: 12805. XDH. | CHEMBL1929. |
| P29275 | Adenosine receptor A2b | HGNC: 264. ADORA2B. | CHEMBL2096679. |
| P08173 | Muscarinic acetylcholine receptor M4 | HGNC: 1953. CHRM4. | CHEMBL 1821. |
| P08912 | Muscarinic acetylcholine receptor M5 | HGNC: 1954. CHRM5. | CHEMBL2094109. |
| Q08828 | Adenylate cyclase type 1 | HGNC: 232. ADCY1. | CHEMBL2899. |
| P20648 | Potassium-transporting ATPase alpha chain 1 | HGNC: 819. ATP4A. | CHEMBL2095173. |
| Q06432 | Voltage-dependent calcium channel gamma-1 sub . . . | HGNC: 1405. CACNG1. | CHEMBL2363032. |
| Q16739 | Ceramide glucosyltransferase | HGNC: 12524. UGCG. | CHEMBL2063. |
| O75907 | Diacylglycerol O-acyltransferase 1 | HGNC: 2843. DGAT1. | CHEMBL6009. |
| P41439 | Folate receptor gamma | HGNC: 3795. FOLR3. | |
| O95838 | Glucagon-like peptide 2 receptor | HGNC: 4325. GLP2R. | CHEMBL5844. |
| P48039 | Melatonin receptor type 1A | HGNC: 7463. MTNR1A. | CHEMBL1945. |
| P49286 | Melatonin receptor type 1B | HGNC: 7464. MTNR1B. | CHEMBL 1946. |
| P30559 | Oxytocin receptor | HGNC: 8529. OXTR. | CHEMBL2049. |
| P43116 | Prostaglandin E2 receptor EP2 subtype | HGNC: 9594. PTGER2. | CHEMBL2363068. |
| Q07326 | Phosphatidylinositol-glycan biosynthesis clas . . . | HGNC: 8962. PIGF. | |
| Q13621 | Solute carrier family 12 member 1 | HGNC: 10910. SLC12A1. | CHEMBL1874. |
| P31639 | Sodium/glucose cotransporter 2 | HGNC: 11037. SLC5A2. | CHEMBL3884. |
| Q9Y5Y9 | Sodium channel protein type 10 subunit alpha | HGNC: 10582. SCN10A. | CHEMBL2331043. |

In some embodiments, the disease specific target is selected from antigens that are overexpressed in cancer cells, including intercellular adhesion molecule 1 (ICAM-1), ephrin type-A receptor 2 (EphA2), ephrin type-A receptor 3 (EphA3), ephrin type-A receptor 4 (EphA4), or activated leukocyte cell adhesion molecule (ALCAM).

In some embodiments, the disease specific target is selected from cancer- or tumor-associated guide antigens, include CD30, CD33, PSMA, mesothelin, CD44, CD73, CD38, Mucin 1 cell surface associated (MUC1), Mucin 2 oligomeric mucus gel-forming (MUC2), and MUC16 (CA-125).

In some embodiments, the disease specific target is selected from CD30, CD33, carcinoembroyonic antigen (CEA), mesothelin, cathepsin G, CD44, CD73, CD38, Muc1, Muc2, Muc16, preferentially expressed antigen of melanoma (PRAME), CD52, EpCAM, CEA, gpA33, Mucins, tumor associated glycoprotein 72 (TAG-72), carbonic anhydrase IX, PSMA, folate binding protein, gangliosides, Lewis-Y, immature laminin receptor, BING-4, calcium-activated chloride channel 2 (CaCC), gp100, synovial sarcoma X breakpoint 2 (SSX-2), or SAP-1.

In some embodiments, the disease specific target is selected from CD30, CD33, arcinoembroyonic antigen (CEA), mesothelin, cathepsin G, CD44, CD73, CD38, Muc1, Muc16, preferentially expressed antigen of melanoma (PRAME), CD52, EpCAM, CEA, gpA33, Mucins, TAG-72, carbonic anhydrase IX, PSMA, folate binding protein, gangliosides or Lewis-Y, ICAM-1, EphA2, or ALCAM.

C. Immuno Regulatory Function Target

In general, the second antigen is an immune regulatory function target that is related to the disease target.

The immune regulatory function target could be a checkpoint receptor (e.g. PD-L1 (patent WO2017020801-PAMPH-866 and Zhang, F., et al. Structural basis of a novel PD-L1 nanobody for immune checkpoint blockade. Cell discovery 3, 17004 (2017).8), or a regulatory cytokines receptor, etc.

In some embodiments, the immune regulatory function target is selected from one of the receptors provided in Table 1.

In some embodiments, the immune regulatory function target is related to NK cell activating or inhibiting pathway, and is selected from CD16, CD38, NKG2D, NKG2A, NKp46 or Killer-cell immunoglobulin like receptors (KIRs).

In some embodiments, the immune regulatory function target is related to checkpoint inhibitory pathway (which can be active in T cell, NK cell or complemental system), and is selected, but not limited from PD1, CTLA4, CD47, CD59 and Tim3.

D. Effector Function Target

In general, the third antigen is an effector function target.

The defined effector function target could be T cell marker (e.g. CD3 (Patent WO2010037838), NK cell (e.g. CD16, Behar, G., et al. Isolation and characterization of anti-Fcgamma RIII (CD16) llama single-domain antibodies that activate natural killer cells. Protein engineering, design & selection: PEDS 21, 1-10 (2008)), Macrophage (e.g. CD47 (patent publication U.S. Pat. No. 8,377,448 B2)), etc. Pairing effector cells with disease specific targets could direct effector cells to disease site to mediate potent effects on disease target with the help of blocking inhibitory immune regulatory target. Further, the fine-tuned affinity of effector function targeting domain pairing with blocking inhibitory immune regulatory target could also improve the safety of effector targeting as described above.

In some embodiments, the effector function target is selected from one of the receptors provided in Table 1.

E. Single Domain Antibody Binding Fragments

In general, the antibodies provided herein comprise multiple single domain antigen binding fragments.

The single domain antibody can be obtained by direct screening methods known in the art against the desired antigen, by modifying a known antibody against a selected target, antigen, or epitope.

The $V_H$ or $V_L$ binding domains could be derived from any single domain binding sources, including but not limited to animal sources (Camel, Llama, Alpaca, engineered mouse/rat, human Ig transgenic mouse/rat etc.), engineered heavy chain only antibody library, engineered light chain only antibody library, humanized antibody binding domains, or by engineering a know binding domain of receptor, ligand, soluable factor against a selected target, antigen, or epitope, etc.

Most antibodies have KD values in the nanomolar ($10^{-7}$ to $10^{-9}$) range. High affinity antibodies generally considered in the picomolar range ($10^{-9}$ to $10^{-11}$) with very high affinity antibodies being in the low picomolar ($10^{-11}$ to $10^{-12}$) range.

Single domain antibody with lower affinity can be generated by fine-tuning an existing antibody, such as by change one or more of the amino acid sequence, thus change the affinity to a desired range, but still retain the specificity. The modification can be in CDR1, CDR2 and/or CDR3 region of an existing antibody. It can also be modifications in frame region of VH or VL. Depending on each antibody, the modification can be rationally designed based on protein 3D structure information. In general, fine-tuning of affinity and specificity can be achieved through engineering and panning a library containing the respective modifications.

The single domain of the present invention binds specifically to a target.

By "target" or "marker" herein is meant any entity that is capable of specifically binding to a particular targeted therapeutic, such as Her2/Neu. In some embodiments, targets are specifically associated with one or more particular cell or tissue types. In some embodiments, targets are specifically associated with one or more particular disease states. In some embodiments, targets are specifically associated with one or more particular developmental stages. For example, a cell type specific marker is typically expressed at levels at least 2-fold greater in that cell type than in a reference population of cells. In some embodiments, the cell type specific marker is present at levels at least 3-fold, at least 4-fold, at least 5-fold, at least 6-fold, at least 7-fold, at least 8-fold, at least 9-fold, at least 10-fold, at least 50-fold, at least 100-fold, or at least 1,000-fold greater than its average expression in a reference population. Detection or measurement of a cell type specific marker may make it possible to distinguish the cell type or types of interest from cells of many, most, or all other types. In some embodiments, a target can comprise a protein, a carbohydrate, a lipid, and/or a nucleic acid, as described herein.

By "specifically binds" or "preferably binds" herein is meant that the binding between two binding partners (e.g., between a targeting moiety and its binding partner) is selective for the two binding partners and can be discriminated from unwanted or non-specific interactions. For example, the ability of an antigen-binding moiety to bind to a specific antigenic determinant can be measured either through an enzyme-linked immunosorbent assay (ELISA) or other techniques familiar to one of skill in the art, e.g. surface plasmon resonance technique (analyzed on a BIAcore® instrument) (Liljeblad et al., Glyco J 17, 323-329 (2000)), and traditional binding assays (Heeley, Endocr Res 28, 217-229 (2002)). The terms "anti-[antigen] antibody" and "an antibody that binds to [antigen]" refer to an antibody that is capable of binding the respective antigen with sufficient affinity such that the antibody is useful as a diagnostic and/or therapeutic agent in targeting the antigen. In some embodiments, the extent of binding of an anti-[antigen] antibody to an unrelated protein is less than about 10% of the binding of the antibody to the antigen as measured, e.g., by a radioimmunoassay (RIA).

In some embodiments, the antigen binding that binds to antigen has a dissociation constant (KD) of <100 μM, <10 μM, <1 μM, <100 nM, <10 nM, <1 nM, <0.1 nM, <0.01 nM, or <0.001 nM (e.g. $10^{-4}$ M or less, e.g. from $10^{-4}$ M to $10^{-12}$ M, e.g., from $10^{-9}$ M to $10^{-13}$ M), and preferably from $10^{-4}$ M to $10^{-6}$ M.

In some embodiments, the targeted therapeutic comprises an antibody, or a functional fragment thereof.

In certain specific embodiments, a target is a tumor marker. In some embodiments, a tumor marker is an antigen that is present in a tumor that is not present in normal organs, tissues, and/or cells. In some embodiments, a tumor marker is an antigen that is more prevalent in a tumor than in normal organs, tissues, and/or cells. In some embodiments, a tumor marker is an antigen that is more prevalent in malignant cancer cells than in normal cells.

By "tumor antigen" herein is meant an antigenic substance produced in tumor cells, i.e., it triggers an immune response in the host. Normal proteins in the body are not antigenic because of self-tolerance, a process in which self-reacting cytotoxic T lymphocytes (CTLs) and autoantibody-producing B lymphocytes are culled "centrally" in primary lymphatic tissue (BM) and "peripherally" in secondary lymphatic tissue (mostly thymus for T-cells and spleen/lymph nodes for B cells). Thus, any protein that is not exposed to the immune system triggers an immune response. This may include normal proteins that are well sequestered from the immune system, proteins that are normally produced in extremely small quantities, proteins that are normally produced only in certain stages of development, or proteins whose structure is modified due to mutation.

In some embodiments, a target is preferentially expressed in tumor tissues and/or cells versus normal tissues and/or cells.

In some embodiments of the invention a marker is a tumor marker. The marker may be a polypeptide that is expressed at higher levels on dividing than on non-dividing cells. For example, Her-2/neu (also known as ErbB-2) is a member of the EGF receptor family and is expressed on the cell surface of tumors associated with breast cancer. Another example is a peptide known as F3 that is a suitable targeting agent for directing a nanoparticle to nucleolin (Porkka et al., 2002, Proc. Natl. Acad. Sci., USA, 99:7444; and Christian et al., 2003, J. Cell Biol., 163:871). It has been shown that targeted particles comprising a nanoparticle and the MO aptamer (which specifically binds to PSMA) were able to specifically and effectively deliver docetaxel to prostate cancer tumors.

Antibodies or other drug that specifically target these tumor targets specifically interfere with and regulate signaling pathways of the biological behavior of tumor cells regulate directly, or block signaling pathway to inhibit tumor cell growth or induce apoptosis. To date, there are dozens of target drugs have been approved for solid tumors or hematological malignancies clinical research and treatment, and there are number of targeted drugs for hematological malignancies.

In some embodiments, the tumor antigen (or tumor target) is selected from the group consisting of: CD2, CD19, CD20, CD22, CD27, CD33, CD37, CD38, CD40, CD44, CD47, CD52, CD56, CD70, CD79, and CD137.

In some embodiments, the tumor antigen (or tumor target) is selected from the group consisting of: 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin an, Integrin anb, KIR, LAG-3, Lewis Y antigen, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3, and variants thereof. The variants of the tumor antigen encompass various mutants or polypormisms known in the art and/or naturally occurred.

By immunoglobulin" or "antibody" herein is meant a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An antibody or antibody fragment may be conjugated or otherwise derivatized within the scope of the claimed subject matter. Such antibodies include IgG1, IgG2a, IgG3, IgG4 (and IgG4 subforms), as well as IgA isotypes.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity and comprise an Fc region or a region equivalent to the Fc region of an immunoglobulin The terms "full-length antibody", "intact antibody", "and "whole antibody" are used herein interchangeably to refer to an antibody having a structure substantially similar to a native antibody structure or having heavy chains that contain an Fc region as defined herein.

By "native antibodies" herein is meant naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The light chain of an antibody may be assigned to one of two types, called kappa (κ) and lambda (λ), based on the amino acid sequence of its constant domain.

By "antibody fragment" herein is meant a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), single-domain antibodies, and multispecific antibodies formed from antibody fragments. For a review of certain antibody fragments, see Hudson et al., Nat Med 9, 129-134 (2003). For a review of scFv fragments, see e.g. Pliickthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

By "antigen binding domain" herein is meant a protein domain that comprises the area which specifically binds to and is complementary to part or all of an antigen. An antigen binding domain may be provided by, for example, one or more antibody variable domains (also called antibody variable regions, or single domain antibody, or domain antibody). Particularly, an antigen binding domain comprises an antibody light chain variable region (VL) and an antibody heavy chain variable region (VH). An antigen binding domain may be also provided by, for example, soluble domain of receptors or ligands, for example, soluble PD-1 domain binding PD-L1/L2, or soluble SIRPa domain binding CD47.

By "variable region" or "variable domain" herein is meant the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

By "hypervariable region" or "HVR" herein is meant each of the regions of an antibody variable domain which are hypervariable in sequence and/or form structurally defined loops "hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The antibody of the present invention can be chimeric antibodies, humanized antibodies, human antibodies, or antibody fusion proteins.

By "chimeric antibody" herein is meant a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a subhuman primate, cat or dog.

By "humanized antibody" herein is meant a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody. In some embodiments, specific residues of the framework region of the humanized antibody, particularly those that are touching or close to the CDR sequences, may be modified, for example replaced with the corresponding residues from the original rodent, subhuman primate, or other antibody.

By "human antibody" herein is meant an antibody obtained, for example, from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al, Nature Genet. 7: 13 (1994), Lonberg et al, Nature 368:856 (1994), and Taylor et al, Int. Immun. 6:579 (1994). A fully human antibody also can be constructed by genetic or chromosomal transfection methods, as well as phage display technology, all of which are known in the art. See for example, McCafferty et al, Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, which are incorporated herein by reference in their entirety.

By "antibody fusion protein" herein is meant a recombinantly-produced antigen-binding molecule in which two or more of the same or different natural antibody, single-chain antibody or antibody fragment segments with the same or different specificities are linked. A fusion protein comprises at least one specific binding site. Valency of the fusion protein indicates the total number of binding arms or sites the fusion protein has to antigen(s) or epitope(s); i.e., monovalent, bivalent, trivalent or multivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent.

By "target" or "marker" herein is meant any entity that is capable of specifically binding to a particular targeting moiety. In some embodiments, targets are specifically associated with one or more particular cell or tissue types. In some embodiments, targets are specifically associated with one or more particular disease states. In some embodiments, targets are specifically associated with one or more particular developmental stages. For example, a cell type specific marker is typically expressed at levels at least 2 fold greater in that cell type than in a reference population of cells. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1,000 fold greater than its average expression in a reference population. Detection or measurement of a cell type specific marker may make it possible to distinguish the cell type or types of interest from cells of many, most, or all other types. In some embodiments, a target can comprise a protein, a carbohydrate, a lipid, and/or a nucleic acid, as described herein.

A substance is considered to be "targeted" for the purposes described herein if it specifically binds to a nucleic acid targeting moiety. In some embodiments, a nucleic acid targeting moiety specifically binds to a target under stringent conditions. An inventive complex or compound comprising targeting moiety is considered to be "targeted" if the targeting moiety specifically binds to a target, thereby delivering the entire complex or compound composition to a specific organ, tissue, cell, extracellular matrix component, and/or intracellular compartment.

In certain embodiments, antibody in accordance with the present invention comprise a single domain antibody or fragment which specifically binds to one or more targets (e.g. antigens) associated with an organ, tissue, cell, extracellular matrix component, and/or intracellular compartment. In some embodiments, compounds comprise a targeting moiety which specifically binds to targets associated with a particular organ or organ system. In some embodiments, compounds in accordance with the present invention comprise a nuclei targeting moiety which specifically binds to one or more intracellular targets (e.g. organelle, intracellular protein). In some embodiments, compounds comprise a targeting moiety which specifically binds to targets associated with diseased organs, tissues, cells, extracellular matrix components, and/or intracellular compartments. In some embodiments, compounds comprise a targeting moiety which specifically binds to targets associated with particular cell types (e.g. endothelial cells, cancer cells, malignant cells, prostate cancer cells, etc.).

In some embodiments, antibodys in accordance with the present invention comprise a domain antibody or fragment which binds to a target that is specific for one or more particular tissue types (e.g. liver tissue vs. prostate tissue). In some embodiments, compounds in accordance with the present invention comprise a domain which binds to a target that is specific for one or more particular cell types (e.g. T cells vs. B cells). In some embodiments, antibodies in accordance with the present invention comprise a domain which binds to a target that is specific for one or more particular disease states (e.g. tumor cells vs. healthy cells). In some embodiments, compounds in accordance with the present invention comprise a targeting moiety which binds to a target that is specific for one or more particular developmental stages (e.g. stem cells vs. differentiated cells).

In some embodiments, a target may be a marker that is exclusively or primarily associated with one or a few cell types, with one or a few diseases, and/or with one or a few developmental stages. A cell type specific marker is typically expressed at levels at least 2 fold greater in that cell type than in a reference population of cells which may consist, for example, of a mixture containing cells from a plurality (e.g., 5-10 or more) of different tissues or organs in approximately equal amounts. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1000 fold greater than its average expression in a reference population. Detection or measurement of a cell type specific marker may make it possible to distinguish the cell type or types of interest from cells of many, most, or all other types.

In some embodiments, a target comprises a protein, a carbohydrate, a lipid, and/or a nucleic acid. In some embodiments, a target comprises a protein and/or characteristic portion thereof, such as a tumor-marker, integrin, cell surface receptor, transmembrane protein, intercellular protein, ion channel, membrane transporter protein, enzyme, antibody, chimeric protein, glycoprotein, etc. In some embodiments, a target comprises a carbohydrate and/or characteristic portion thereof, such as a glycoprotein, sugar (e.g., monosaccharide, disaccharide, polysaccharide), glycocalyx (i.e., the carbohydrate-rich peripheral zone on the outside surface of most eukaryotic cells) etc. In some embodiments, a target comprises a lipid and/or characteristic portion thereof, such as an oil, fatty acid, glyceride, hormone, steroid (e.g., cholesterol, bile acid), vitamin (e.g, vitamin E), phospholipid, sphingolipid, lipoprotein, etc. In some embodiments, a target comprises a nucleic acid and/or characteristic portion thereof, such as a DNA nucleic acid; RNA nucleic acid; modified DNA nucleic acid; modified RNA nucleic acid; nucleic acid that includes any combination of DNA, RNA, modified DNA, and modified RNA.

Numerous markers are known in the art. Typical markers include cell surface proteins, e.g., receptors. Exemplary receptors include, but are not limited to, the transferrin receptor; LDL receptor; growth factor receptors such as epidermal growth factor receptor family members (e.g., EGFR, Her2, Her3, Her4) or vascular endothelial growth factor receptors, cytokine receptors, cell adhesion molecules, integrins, selectins, and CD molecules. The marker can be a molecule that is present exclusively or in higher amounts on a malignant cell, e.g., a tumor antigen.

In some embodiments, the binding domain binds to a tumor cell specifically or preferably in comparison to a non-tumor cell.

The binding of target moiety to tumor cell can be measured using assays known in the art.

In some embodiments, the tumor cell is of a carcinoma, a sarcoma, a lymphoma, a myeloma, or a central nervous system cancer.

In some embodiments, the binding domain is capable of binding to a tumor antigen specifically or preferably in comparison to a non-tumor antigen.

In certain specific embodiments, a target is a tumor marker. In some embodiments, a tumor marker is an antigen that is present in a tumor that is not present in normal organs, tissues, and/or cells. In some embodiments, a tumor marker is an antigen that is more prevalent in a tumor than in normal organs, tissues, and/or cells. In some embodiments, a tumor marker is an antigen that is more prevalent in malignant cancer cells than in normal cells.

In some embodiments, the targeting moiety comprises folic acid or a derivative thereof.

In recent years, research on folic acid had made great progress. Folic acid is a small molecule vitamin that is necessary for cell division. Tumor cells divide abnormally and there is a high expression of folate receptor (FR) on tumor cell surface to capture enough folic acid to support cell division.

Data indicate FR expression in tumor cells is 20-200 times higher than normal cells. The expression rate of FR in various malignant tumors are: 82% in ovarian cancer, 66% in non-small cell lung cancer, 64% in kidney cancer, 34% in colon cancer, and 29% in breast cancer (Xia W, Low P S. Late-targeted therapies for cancer. J Med Chem. 2010; 14; 53 (19):6811-24). The expression rate of FA and the degree of malignancy of epithelial tumor invasion and metastasis is positively correlated. FA enters cell through FR mediated endocytosis, and FA through its carboxyl group forms FA complexes with drugs which enter the cells. Under acidic conditions (pH value of 5), FR separates from the FA, and FA releases drugs into the cytoplasm.

Clinically, the system can be used to deliver drugs selectively attack the tumor cells. Folic acid has small molecular weight, has non-immunogenicity and high stability, and is inexpensive to synthesis. More importantly, chemical coupling between the drug and the carrier is simple, and as such using FA as targeting molecule to construct drug delivery system has become a research hotspot for cancer treatment. Currently EC145 (FA chemotherapy drug conjugate compound) that is in clinical trials can effectively attack cancer cells (Pribble P and Edelman M J. EC145: a novel targeted agent for adenocarcinoma of the lung. Expert Opin. Investig. Drugs (2012) 21:755-761).

In some embodiments, the targeting moiety comprises extracellular domains (ECD) or soluble form of PD-1, PDL-1, CTLA4, CD47, BTLA, KIR, TIM3, 4-1BB, and LAG3, full length of partial of a surface ligand Amphiregulin, Betacellulin, EGF, Ephrin, Epigen, Epiregulin, IGF, Neuregulin, TGF, TRAIL, or VEGF.

In some embodiments, the targeting moiety comprises a Fab, Fab', F(ab')2, single domain antibody, T and Abs dimer, Fv, scFv, dsFv, ds-scFv, Fd, linear antibody, minibody, diabody, bispecific antibody fragment, bibody, tribody, sc-diabody, kappa (lamda) body, BiTE, DVD-Ig, SIP, SMIP, DART, or an antibody analogue comprising one or more CDRs.

In some embodiments, the targeting moiety is an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies that are known in the art can be used in the compounds of the invention, in particular for the treatment of the disease with which the target antigen is associated. Examples of target antigens (and their associated diseases) to which an antibody-linker-drug conjugate of the invention can be targeted include: CD2, CD19, CD20, CD22, CD27, CD33, CD37, CD38, CD40, CD44, CD47, CD52, CD56, CD70, CD79, CD137, 4-1BB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin an, Integrin anb , KIR, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3.

F. Manufacturing the Antibodies

All of the antibody formats are based on heavy chain and light chain of an IgG antibody that can be manufactured using methods known in the art, which typically include steps of construction of expression cassette for the heavy and light chain genes, co-transfect the two genes into a suitable cell system to produce the recombinant antibody and to make a stable and high-productive cell clone, cell fermentation to produce cGMP final antibody product.

III. Pharmaceutical Formulations and Administration

The present invention further relates to a pharmaceutical formulation comprising a compound of the invention or a pharmaceutically acceptable salt thereof, and one or more pharmaceutically acceptable carriers.

The compounds described herein including pharmaceutically acceptable carriers such as addition salts or hydrates thereof, can be delivered to a patient using a wide variety of routes or modes of administration. Suitable routes of administration include, but inhalation, transdermal, oral, rectal, transmucosal, intestinal and parenteral administration, including intramuscular, subcutaneous and intravenous injections. Preferably, the compounds of the invention comprising an antibody or antibody fragment as the targeting moiety are administered parenterally, more preferably intravenously.

As used herein, the terms "administering" or "administration" are intended to encompass all means for directly and indirectly delivering a compound to its intended site of action.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from a disease state caused by an organism that relies on an autoinducer, the compounds of the invention can be administered in cocktails containing agents used to treat the pain, infection and other symptoms and side effects commonly associated with the disease. Such agents include, e.g., analgesics, antibiotics, etc.

When administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); Ca+2 antagonists (e.g., verapamil, nifedipine, nitrendipine and caroverine); amphotericin; tri-paranol analogues (e.g., tamoxifen); antiarrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, and suspensions for oral ingestion by a patient to be treated. Pharmaceutical preparations for oral use can be obtained solid excipient, optionally grinding a resulting mixture, and processing the mixture of granules, after adding suitable auxiliaries, if desired to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include calcium carbonate, calcium phosate, various sugars, starches, cellulose derivatives, gelatin, and polymers such as polyethylene glycols.

A preferred pharmaceutical composition is a composition formulated for injection such as intravenous injection and includes about 0.01% to about 100% by weight of the compound of the present invention, based upon 100% weight of total pharmaceutical composition. The drug-ligand conjugate may be an antibody-cytotoxin conjugate where the antibody has been selected to target a particular cancer.

In some embodiments, the pharmaceutical composition of the present invention further comprises an additional therapeutic agent.

In some embodiments, the additional therapeutic agent is an anticancer agent.

In some embodiments, the additional anticancer agent is selected from an antimetabolite, an inhibitor of topoisomerase I and II, an alkylating agent, a microtubule inhibitor, an antiandrogen agent, a GNRh modulator or mixtures thereof.

In some embodiments, the additional therapeutic agent is a chemotherapeutic agent.

By "chemotherapeutic agent" herein is meant a chemical compound useful in the treatment of cancer. Examples are but not limited to: Gemcitabine, Irinotecan, Doxorubicin, 5-Fluorouracil, Cytosine arabinoside ("Ara-C"), Cyclophosphamide, Thiotepa, Busulfan, Cytoxin®, TAXOL®, Methotrexate, Cisplatin, Melphalan, Vinblastine and Carboplatin.

In some embodiments, the second chemotherapeutic agent is selected from the group consisting of tamoxifen, raloxifene, anastrozole, exemestane, letrozole, imatinib, paclitaxel, cyclophosphamide, lovastatin, minosine, gemcitabine, cytarabine, 5-fluorouracil, methotrexate, docetaxel, goserelin, vincristine, vinblastine, nocodazole, teniposide etoposide, gemcitabine, epothilone, vinorelbine, camptothecin, daunorubicin, actinomycin D, mitoxantrone, acridine, doxorubicin, epirubicin, or idarubicin.

IV. Kits

In another aspect, the present invention provides kits containing the therapeutic combinations provided herein and directions for using the therapeutic combinations. The kit may also include a container and optionally one or more vial, test tube, flask, bottle, or syringe. Other formats for kits will be apparent to those of skill in the art and are within the scope of the present invention.

V. Medical Use

In another aspect, the present invention provides a method for treating a disease condition in a subject that is in need of such treatment, comprising: administering to the subject a therapeutic combination or pharmaceutical composition comprising a therapeutically effective amount of the compound of the present invention or a pharmaceutically acceptable salt thereof, and a pharmaceutical acceptable carrier.

In addition to the compositions and constructs described above, the present invention also provides a number of uses of the combinations of the invention. Uses of the combinations of the current invention include: killing or inhibiting the growth, proliferation or replication of a tumor cell or cancer cell, treating cancer, treating a pre-cancerous condition, preventing the multiplication of a tumor cell or cancer cell, preventing cancer, preventing the multiplication of a cell that expresses an auto-immune antibody. These uses comprise administering to an animal such as a mammal or a human in need thereof an effective amount of a compound of the present invention.

The combination of the current invention is useful for treating diseases such as cancer in a subject, such as a human being. Combinations and uses for treating tumors by providing a subject the composition in a pharmaceutically acceptable manner, with a pharmaceutically effective amount of a composition of the present invention are provided.

By "cancer" herein is meant the pathological condition in humans that is characterized by unregulated cell proliferation. Examples include but are not limited to: carcinoma, lymphoma, blastoma, and leukemia. More particular examples of cancers include but are not limited to: lung (small cell and non-small cell), breast, prostate, carcinoid, bladder, gastric, pancreatic, liver (hepatocellular), hepatoblastoma, colorectal, head and neck squamous cell carcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML).

By "inhibiting" or "treating" or "treatment" herein is meant to reduction, therapeutic treatment and prophylactic or preventative treatment, wherein the objective is to reduce or prevent the aimed pathologic disorder or condition. In one example, following administering of a compound of the present invention, a cancer patient may experience a reduction in tumor size. "Treatment" or "treating" includes (1) inhibiting a disease in a subject experiencing or displaying the pathology or symptoms of the disease, (2) ameliorating a disease in a subject that is experiencing or displaying the pathology or symptoms of the disease, and/or (3) affecting any measurable decrease in a disease in a subject or patient that is experiencing or displaying the pathology or symptoms of the disease. To the extent a compound of the present invention may prevent growth and/or kill cancer cells, it may be cytostatic and/or cytotoxic.

By "therapeutically effective amount" herein is meant an amount of a compound provided herein effective to "treat" a disorder in a subject or mammal. In the case of cancer, the therapeutically effective amount of the drug may either reduce the number of cancer cells, reduce the tumor size, inhibit cancer cell infiltration into peripheral organs, inhibit tumor metastasis, inhibit tumor growth to certain extent, and/or relieve one or more of the symptoms associated with the cancer to some extent.

Administration "in combination with" one or more further therapeutic agents includes simultaneous (concurrent) and consecutive administration in any order. As used herein, the term "pharmaceutical combination" refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

In some embodiments, the diseases condition is tumor or cancer. In some embodiments, the cancer or tumor is selected from stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer or lymphoma.

In some embodiments, the disease condition comprises abnormal cell proliferation, such as a pre-cancerous lesion.

The current invention is particularly useful for the treatment of cancer and for the inhibition of the multiplication of a tumor cell or cancer cell in an animal. Cancer, or a precancerous condition, includes a tumor, metastasis, or any disease or disorder characterized by uncontrolled cell growth, can be treated or prevented by administration the drug-ligand complex of the current invention. The compound delivers the activating moiety to a tumor cell or cancer cell. In some embodiments, the targeting moiety specifically binds to or associates with a cancer-cell or a tumor-cell-associated antigen. Because of its close proximity to the ligand, after being internalized, the activating moiety can be taken up inside a tumor cell or cancer cell through, for example, receptor-mediated endocytosis. The antigen can be attached to a tumor cell or cancer cell or can be an extracellular matrix protein associated with the tumor cell or cancer cell. Once inside the cell, the linker is hydrolytically or enzymatically cleaved by a tumor-cell or cancer-cell-associated proteases, thereby releasing the activating moiety. The released activating moiety is then free to diffuse and induce or enhance immune activity of immune cells or tumor cells. In an alternative embodiment, the activating moiety is cleaved from the compound tumor microenvironment, and the drug subsequently penetrates the cell.

Representative examples of precancerous conditions that may be targeted by the compounds of the present invention, include: metaplasia, hyperplasia, dysplasia, colorectal polyps, actinic ketatosis, actinic cheilitis, human papillomaviruses, leukoplakia, lychen planus and Bowen's disease.

Representative examples of cancers or tumors that may be targeted by compounds of the present invention include: lung cancer, colon cancer, prostate cancer, lymphoma, melanoma, breast cancer, ovarian cancer, testicular cancer, CNS cancer, renal cancer, kidney cancer, pancreatic cancer, stomach cancer, oral cancer, nasal cancer, cervical cancer and leukemia. It will be readily apparent to the ordinarily skilled artisan that the particular targeting moiety used in the compound can be chosen such that it targets the activating moiety to the tumor tissue to be treated with the drug (i.e., a targeting agent specific for a tumor-specific antigen is chosen). Examples of such targeting moiety are well known in the art, examples of which include anti-Her2 for treatment of breast cancer, anti-CD20 for treatment of lymphoma, anti-PSMA for treatment of prostate cancer and anti-CD30 for treatment of lymphomas, including non-Hodgkin's lymphoma.

In some embodiments, the abnormal proliferation is of cancer cells.

In some embodiments, the cancer is selected from the group consisting of: breast cancer, colorectal cancer, diffuse large B-cell lymphoma, endometrial cancer, follicular lymphoma, gastric cancer, glioblastoma, head and neck cancer, hepatocellular cancer, lung cancer, melanoma, multiple myeloma, ovarian cancer, pancreatic cancer, prostate cancer, and renal cell carcinoma.

In some embodiments, the present invention provides a compound for use in killing a cell. The compound is administered to the cell in an amount sufficient to kill said cell. In an exemplary embodiment, the compound is administered to a subject bearing the cell. In a further exemplary embodiment, the administration serves to retard or stop the growth of a tumor that includes the cell (e.g., the cell can be a tumor cell). For the administration to retard the growth, the rate of growth of the cell should be at least 10% less than the rate of growth before administration. Preferably, the rate of growth will be retarded at least 20%, 30%, 40%, 50%, 60%, 70%, 80%, 90%, or completely stopped.

Additionally, the present invention provides a compound or a pharmaceutical composition of the present invention for use as a medicament. The present invention also provides a compound or a pharmaceutical composition for killing, inhibiting or delaying proliferation of a tumor or cancer cell.

Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inhibition cell growth or division. In preferred embodiments, the cellular activity is at least 25% inhibited. Target plasma concentrations of active compound(s) that are capable of inducing at least about 30%, 50%, 75%, or even 90% or higher inhibition of cellular activity are presently preferred. The percentage of inhibition of cellular activity in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring cellular inhibition and adjusting the dosage upwards or downwards, as described above.

A therapeutically effective dose can also be determined from human data for compounds which are known to exhibit similar pharmacological activities. The applied dose can be adjusted based on the relative bioavailability and potency of the administered compound as compared with the known compound.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

Therapeutic amounts of specific antibodies disclosed herein can also be administered, as a component of the combination, with the immunotherapeutics, either in a single mixture form, or separately. In some embodiments, therapeutic amounts are amounts which eliminate or reduce the patient's tumor burden, or which prevent or reduce the proliferation of metastatic cells. The dosage will depend on many parameters, including the nature of the tumor, patient history, patient condition, the possible co-use of other oncolytic agents, and methods of administration. Methods of administration include injection (e.g., parenteral, subcutaneous, intravenous, intraperitoneal, etc.) for which the antibodies are provided in a nontoxic pharmaceutically acceptable carrier such as water, saline, Ringer's solution, dextrose solution, 5% human serum albumin, fixed oils, ethyl oleate, or liposomes. Typical dosages may range from about 0.01 to about 20 mg/kg, such as from about 0.1 to about 10 mg/kg. Other effective methods of administration and dosages may be determined by routine experimentation and are within the scope of this invention.

The therapeutically effective amount of the agents (disclosed herein) administered, when it is used for combination therapy, can vary depending upon the desired effects and the subject to be treated. For example, the subject can receive at least 1 mg/kg (such as 1 mg/kg to 20 mg/kg, 2.5 mg/kg to 10 mg/kg, or 3.75 mg/kg to 5 mg/kg) intravenously of each antibody agent. The dosage can be administered in divided doses (such as 2, 3, or 4 divided doses per day), or in a single dosage.

In the method for combined administration, the agent may be simultaneously administered with the antibody used in the present invention, or the agent may be administered before or after the administration of the antibody used in the present invention.

For other modes of administration, dosage amount and interval can be adjusted individually to provide plasma levels of the administered compound effective for the particular clinical indication being treated. For example, in one embodiment, a compound according to the invention can be administered in relatively high concentrations multiple times per day. Alternatively, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The present invention is further exemplified, but not limited, by the following Examples that illustrate the preparation of the compounds of the invention.

Example 1

Bi-Specific GCT Ab Targeting HER2$^+$CD47$^+$ Double Positive Cells.

To achieve a goal of Prove of Concept, one bi-specific Guided Combinational Therapeutic Antibody (GCT Ab), targeting HER2$^+$CD47$^+$ double positive cells (FIG. 4) is generated. This GCT Ab contains an engineered single domain antibody against HER2 linked to the N-terminus of CH1 and a single binding domain of engineered SIRPa against CD47 linked to the N-terminus of CK. The Fc of IgG1 is kept as wild type just for testing if the GCT Ab can selectively bind HER2$^+$CD47$^+$ double positive cells vs HER2+ or CD47+ single positive cells.

An anti-HER2 single domain antibody (Gene 069, SEQ ID No. 1 and No. 2) was engineered from the VH gene of Herceptin® by design and gene synthesize based on our Know-how arts. Second, a partially humanized anti-HER2 single domain antibody (Gene 016, SEQ ID No. 3 and No. 4) was designed and synthesized based on the published sdAb C7b (Even-Desrumeaux, K. et al: Molecular bioSystems, 2012, p. 2385-2394, Vol. 8, No. 9). They were engineered to the N-terminal of CH1 of human IgG1 heavy chain via one of the linkers (Linker SEQ ID No. 13~No. 27, including natural VH-CH1 linker, chimeric VH-CK linker, GS-flexible linker, upper and middle Hinge linker of IgG1 and IgG3, etc.).

The binding domain of human SIRPa, the receptor for CD47, was synthesized as a CD47 binding domain. Both the wild type variant 1 (Gene 007, SEQ ID No. 5 and No. 6, with an affinity of $4.5 \times 10^{-7}$M and variant 2 (Gene 012, SEQ ID No. 7 and No. 8, with an affinity of $2.8 \times 10^{-7}$M) of the binding domain of human SIRPa were synthesized (Weiskopf, K. et al: Science 341 (6141), 88-91, 2013). They were engineered to the N-terminal of CK of human kappa light chain via one of the linkers (Linker SEQ ID No. 13~No. 27)

Figure 5:
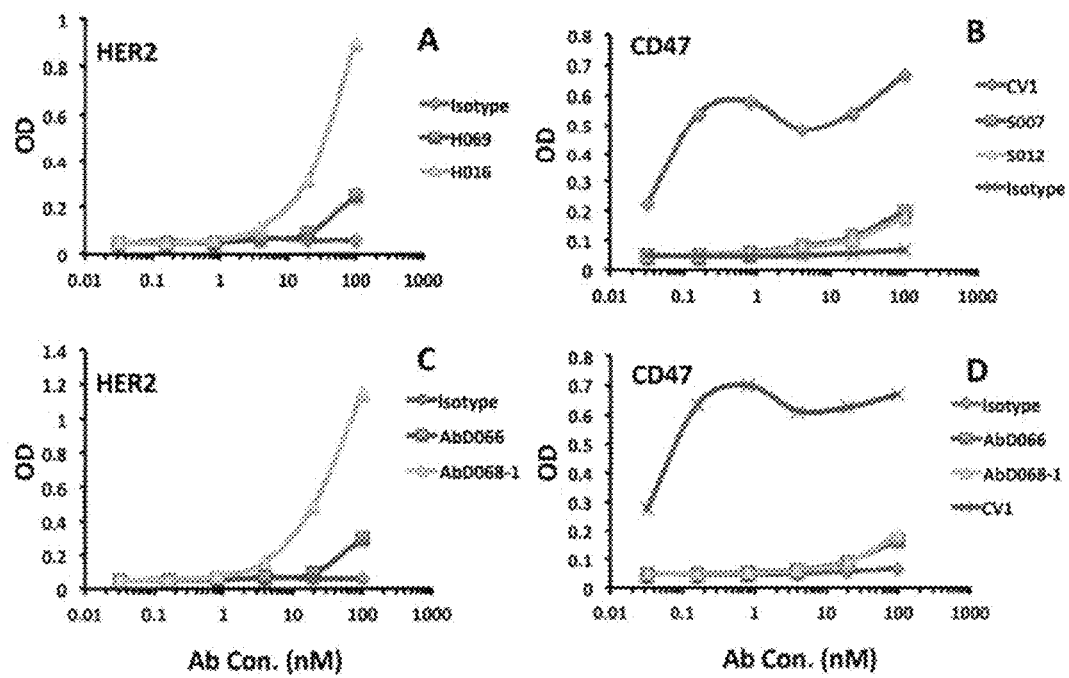
FIGS. 5A-5D show ELISA binding results of Bi-specific GCT Ab against HER2 and CD47. 5A shows the parental individual binding domain antibodies against HER2 and 5B shows the parental individual binding domain antibodies against CD47. 5C and 5D: GCT Ab AbD066 and AbD068-1 binding to HER2 and CD47, respectively.

The two anti-Her2 single domain antibodies in heavy chain were expressed by co-transfection with an empty kappa chain (without V region) into Expi293™ cells, designated as H069 and H016. Their appearance binding affinity was checked via ELISA against recombinant HER2 extracellular domain protein. As shown in FIG. 5A, the H016 of partially humanized anti-HER2 sdAb C7b has an apparent EC50 about $10^{-6}$ M, while the H069 of the single domain VH of Herceptin has an apparent EC50 weaker than about $10^{-6}$M.

The two CD47 antagonist SIRPa variants in kappa chain were expressed by co-transfection with an empty IgG1 heavy chain (without VH region) into Expi293F™ cells, designated as S007 and S012. Their appearance binding affinity was checked via ELISA against recombinant CD47 extracellular domain protein. As shown in FIG. 5B, both of the S007 antibody of SIRPa variant 2 and the S012 antibody of SIRPa variant 1 showed an EC50 binding avidity weaker than about $10^{-7}$ M, while a positive control of high affinity SIRPa mutant, CV1, showed an EC50 binding avidity stronger than $10^{-10}$ M.

We then engineered a series of recombinant bi-specific antibodies with the anti-HER2 single domains linked to IgG1 heavy chain via different linkers and the CD47 binding domain of SIRPa variants linked to kappa chain via different linkers. After primary screening the supernatant of contransfected Expi293F™ cell cultures of a matrix of the combination of different heavy and light chain constructs, we identify that two pairs of combination gave us consistent production yield and ELISA binding activity and were designated as antibody AbD066 (SEQ ID No. 36, No. 37 for heavy chain and SEQ ID No. 38, No. 39 for light chain) and AbD068-1 (SEQ ID No. 40, No. 41 for heavy chain and SEQ ID No. 42, No. 43 for light chain). As showed in FIGS. 5C and 5D, AbD066 retains weaker than about 10-7 M binding activity against CD47 or HER2 in ELISA similar to that of the H069 and S012 parent antibodies, while AbD068-1 retain the H16's ~1×10-7 M binding activity against HER2 and the S007's weaker than about 10-7 M binding activity against CD47.

Figure 6A:
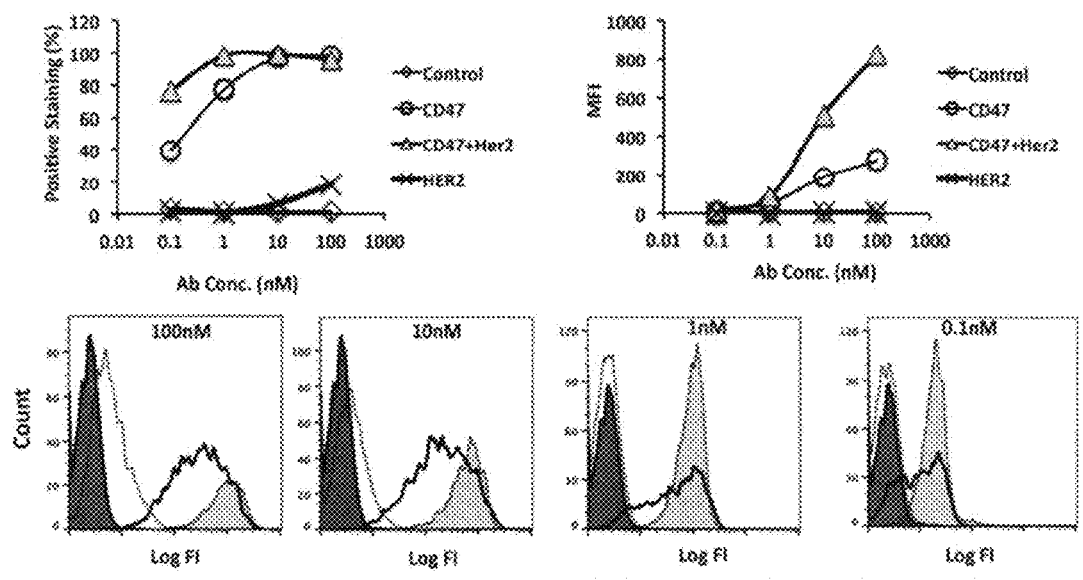
FIGS. 6A and 6B show cell surface staining results detected by flow cytometry for the Bi-specific GCT Ab against HER2 and CD47, Ab AbD066 and AbD068-1, respectively. The left top panel of 6A and 6B shows the percentage of positive cells and the right top panel of 6A and 6B show the median of florescence intensity (MFI) of cell populations stained. The lower panel of 6A and 6B shows the overlay histogram staining results over a set of 4 cell populations (Filled black: Control cells; Empty dot line: HER2+ single positive cells; Empty solid line: CD47+ single positive cells; Tint dot line: CD47+HER2+ double positive cells)
Figure 6B:
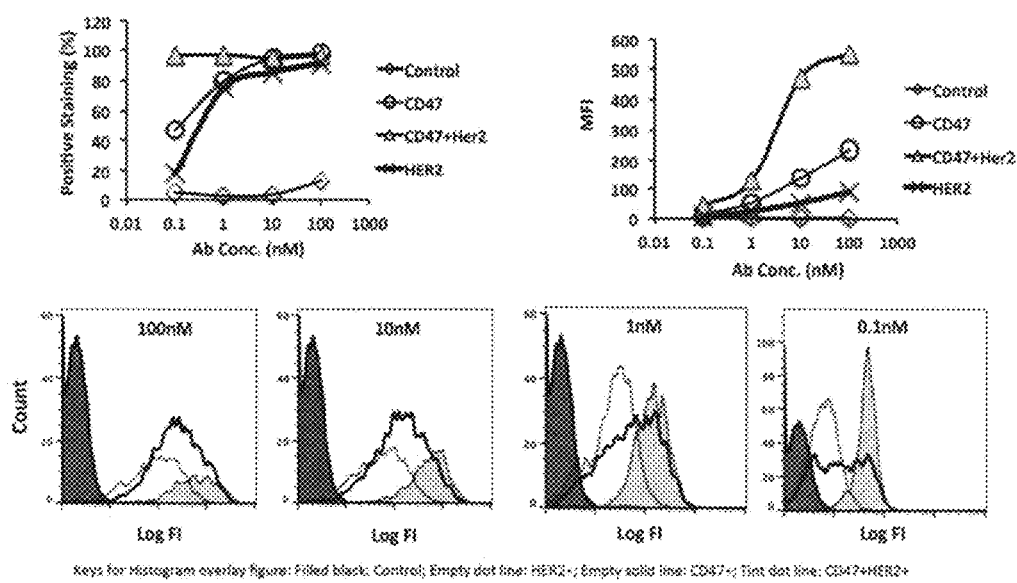

To check the binding capacity of our bi-specific Ab targeting HER2 and CD47 target on cell surface, we made a set of stable CHO-K1 cell pools that are either HER positive, CD47 positive or HER and CD47 double positive as well as controls. We performed cell surface staining experiments with our recombinant antibodies. As showed in FIGS. 6A and 6B, both the AbD066 and AbD068-1 can bind cell surface CD47 at high concentration, but the percentage and MFI of stained CD47 mono-positive CHO cell pool dropped dramatically along the titration down of antibody. The AbD066 and AbD068-1 showed differential staining of the HER2 monospecific CHO cell pool. The AbD066 only partially stained the cell at very high concentration (100 nM), which is consistent with its weak binding of HER2 in ELISA assay. The AbD068-1 showed lower but similar cell surface HER2 staining pattern to that of CD47 that the percentage and MFI of stained HER2 mono-positive CHO cell pool dropped dramatically along the titration down of antibody. Remarkably, both the AbD066 and AbD068-1 showed strong staining of the HER2 and CD47 double positive CHO cell pool. The MFI of AbD066 and AbD068-1 on the HER2 and CD47 double positive CHO cell are substantially higher than that on either HER positive or CD47 positive CHO cells alone, and are also higher than the additive of them. The percentage of stained HER2 and CD47 double positive CHO cell by both AbD066 and AbD068-1 stayed high at the low concentration of 1 nM for AbD066 (FIG. 6A) and 0.1 nM for AbD068-1 (FIG. 6B). The staining on the double targets positive CHO cell is about 100-fold stronger than that on the single target positive cells.

Therefore, these experiments demonstrated that the combination of two fine-tuned low affinity single binding domains against two different surface targets on the same cell using our GCT-Ab platform generated synergistic binding avidity effect on cells displaying double targets that is superior to the binding of cells expressing only one of the two targets. This indicates that the bispecific antibodies generated by our GCT Ab method will preferably target cells expressing both antigens over cells only express one of the targets. The novel bi-specific GCT Ab, designated as ABP366 (AbD066 and AbD068-1), are potentially effective antibody drugs for safer and effective treatment of HER2/CD47 double positive cancers. It provides highly effective multiple-functions targeting: (1) selectively targeting tumor via synergistic binding of HER2 and CD47, which are enriched on some tumor not on normal cells; (2) selectively attract Macrophage cell to attack tumor via tumor binding blocking CD47/SIRPa interaction; and (3) retaining long PK and Fc effector functions. It also provides safety fine-tuned affinity combination: (1) low affinity of CD47 binding (~1 uM), alone can not tightly bind CD47 on normal cells, but enough to block CD47's inhibitory effect when enriched on tumor; and (3) low affinity for Tumor Target HER2 (~1 uM), alone can not tightly bind low level HER2 on normal cells.

Example 2

Bi-Specific GCT Ab Targeting PD-L1$^+$CD47$^+$ Double Positive Cells.

Figure 4:
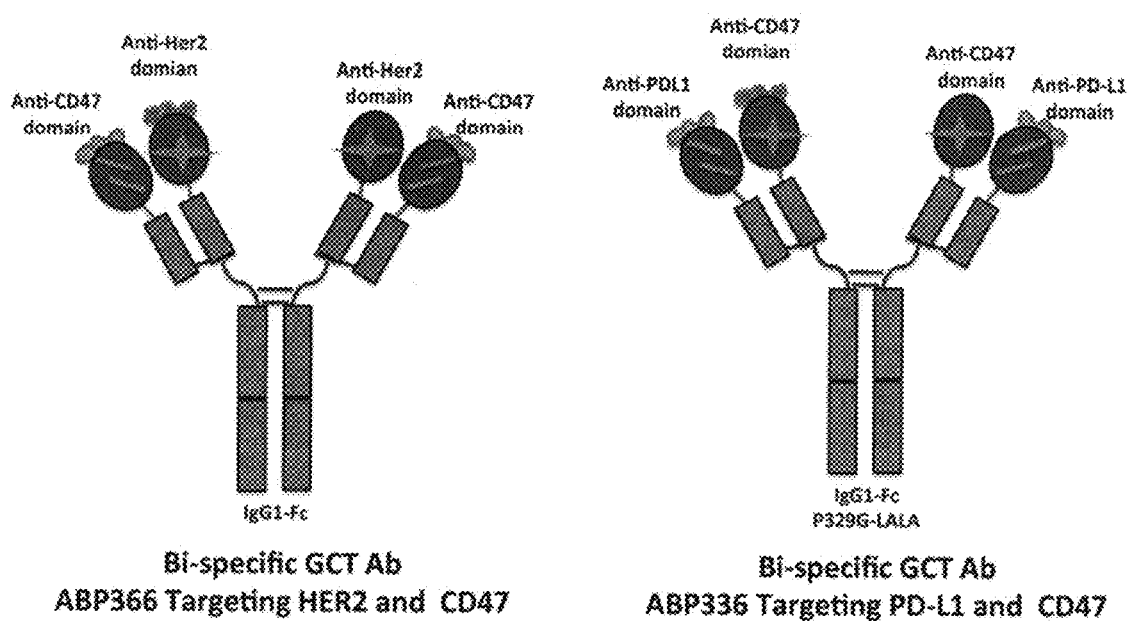
FIG. 4 depicts bi-specific GCT Ab ABP366 and ABP336. The left panel depicts the GCT Ab ABP366 that contains an engineered single domain antibody against HER2 linked to the N-terminus of CH1 via a linker and a single binding domain of engineered SIRPa against CD47 linked to the N-terminus of CK via a linker. The Fc of IgG1 is kept as wild type. The right panel depicts the GCT Ab ABP336 that contains a single binding domain of engineered SIRPa against CD47 linked to the N-terminus of CH1 via a linker and a single binding domain of engineered PD-1 against PD-L1 linked to the N-terminus of CK via a linker. The P329G-LALA mutant Fc of IgG1 is used to retain long PK while knocking out potential detrimental effects of Fc effector functions.

Both PD-L1 and CD47 are immune regulatory surface proteins employed by cancer cells to avoid the attack of effector immune cells. The PD1/PD-L1 target has been proved valuable in the field, while the CD47 target is under extensive testing. However, both targets play important immune regulatory functional roles. Blocking any one of them may often generate adverse effect. Our GCT Ab strategy has the potential of selectively targeting cancer cells over expressing both PD-L1 and CD47, while leave normal cells unharm. To prove of the concept, we designed and generated hi-specific GCT Ab targeting PD-L1 and CD47 double positive cells. This GCT Ab contains a single binding domain of engineered SIRPa against CD47 linked to the N-terminus of CH1 and a single IgV domain of PD-1 against PD-L1 linked to the N-terminus of CK (FIG. 4). The Fc part of IgG1 is engineered as P329G-LALA mutant to devoid of all effector cell functions while retain properties of FcRn binding for durable PK, Protein A binding for standard production and purification. We aimed to test if the GCT Ab can selectively bind PD-L$^+$CD47$^+$ double positive cells vs PD-L1+ or CD47+ single positive cells.

We selected native PD-1 extracellular binding domain to PD-L1 as one of the single binding domain part of our GCT Ab because PD-1 has a low affinity (3.88 uM) to PD-L1 (Maute, R. et al: Proc Natl Acad Sci USA. 112(47): E6506-14. 2015), which may be ideal for our GCT Ab design. We engineered the IgV domain of PD-1 (Gene 048, SEQ ID No. 11 and No. 12) and its lower affinity L128R mutant (Gene 050, SEQ ID No. 9 and No. 10). We selected to link the PD-L1 binding domain to CL chain because our initial experiments indicated that the position of PD-1 domain will affect its binding function to PD-L1.

Figure 7:
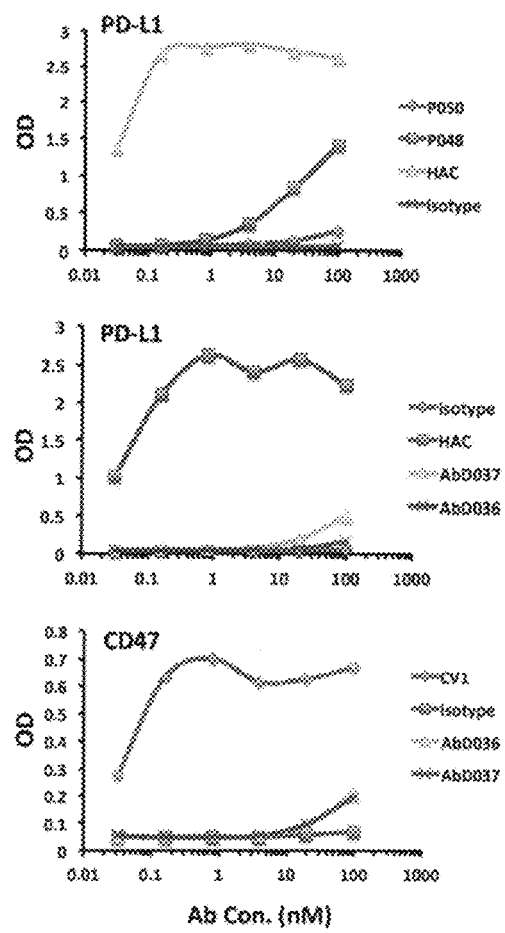
FIG. 7 show ELISA binding results of Bi-specific GCT Ab against PD-L1 and CD47. The top panel shows the parental individual binding domain antibodies against PD-L1 and the middle and lower panels show the GCT Ab AbD036 and AbD037 binding to PD-L1 and CD47, respectively. A high affinity antibody of HAC against PD-L1 and a high affinity antibody of CV1 against CD47 were used as positive controls.

The two PD-1 IgV in kappa chain were expressed by co-transfection with an empty IgG1 heavy chain (without VH region) into Expi293F™ cells, designated as P048 and P050. Their appearance binding affinity was checked via ELISA against recombinant PD-L1 extracellular domain protein. As shown in FIG. 7, both P048 and P050 of PD-1 variants showed an EC50 binding avidity weaker than 10-7 M, while a positive control of high affinity PD-1 mutant, HAC, showed an EC50 binding avidity stronger than $10^{-10}$ M.

The two anti-CD47 single domain of SIPRa (Gene 007 and Gene 012) were engineered in heavy chain and were expressed by co-transfection with an empty kappa chain (without V region) into Expi293F™ cells. Their appearance binding affinity was checked via ELISA against recombinant CD47 extracellular domain protein and was similar to that of S007 and S012 in FIG. 5B.

We then engineered a series of recombinant bi-specific antibodies with the CD47 binding domain of SIRPa variants linked to IgG1 heavy chain via different linkers and the PD-L1 binding domain of PD-1 variants linked to kappa chain via different linkers. After primary screening the supernatant of co-transfected Expi293F™ cell cultures of a matrix of the combination of different heavy and light chain constructs, we identify that two pairs of combination gave us consistent production yield and ELISA binding activity and were designated as antibody AbD036 (SEQ ID No. 28, No. 29 for heavy chain and SEQ ID No. 30, No. 31 for light chain) and AbD037 (SEQ ID No. 32, No. 33 for heavy chain and SEQ ID No. 34, No. 35 for light chain). As showed in FIG. 7, AbD036 showed weaker than about $10^{-7}$ M binding activity against CD47 or PD-L1 in ELISA, while AbD037 also showed the P048's weaker than 1×10$^{-7}$ M binding activity against PD-L1 and the S007's weaker than about $10^{-7}$ M binding activity against CD47.

Figure 8A:
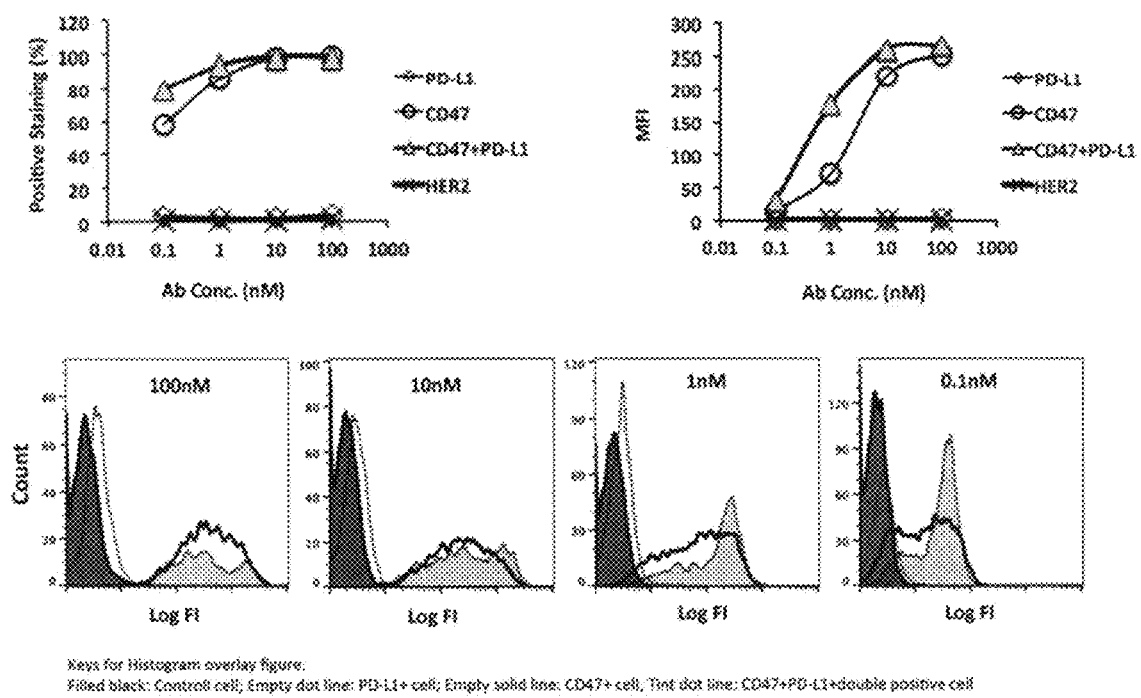
FIGS. 8A and 8B show cell surface staining results detected by flow cytometry for the Bi-specific GCT Ab against PD-L1 and CD47, Ab AbD036 and AbD037, respectively. The left top panel of 8A and 8B shows the percentage of positive cells and the right top panel of 8A and 8B show the median of florescence intensity (MFI) of cell populations stained. The lower panel of 8A and 8B shows the overlay histogram staining results over a set of 4 cell populations (Filled black: Control cells; Empty dot line: PD-L1 single positive cells; Empty solid line: CD47 single positive cells; Tint dot line: CD47 and PD-L1 double positive cells)
Figure 8B:
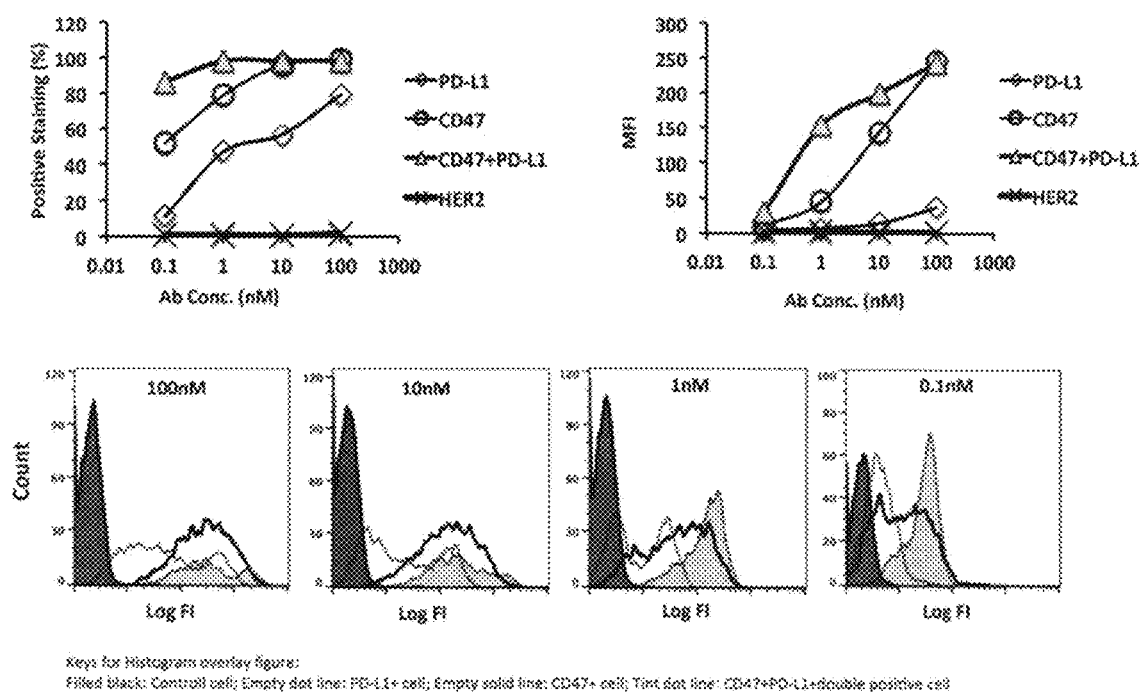

To check the binding capacity of the bi-specific Ab targeting PD-L1 and CD47-targets on cell surface, we made an additional stable CHO-K1 cell pools that are either PD-L1 positive, or PD-L1 and CD47 double positive as well as controls. We performed cell surface staining experiments with our recombinant antibodies. As showed in FIGS. 8A and 8B, both the AbD036 and AbD037 can bind cell surface CD47 well, while the percentage and MFI of stained CD47 mono-positive CHO cell pool dropped along the titration down of antibody. The AbD036 and AbD037 showed differential staining of the PD-L1 monospecific CHO cell pool. The AbD036 only partially stained the cell at very high convention (100 nM), which is consistent with its weak binding of PD-L1 in ELISA assay. The AbD037 showed lower but similar cell surface PD-L1 staining pattern to that of CD47 that the percentage and MFI of stained PD-L1 mono-positive CHO cell pool dropped dramatically along the titration down of antibody. Remarkably, both the AbD036 and AbD037 showed strong staining of the PD-L1 and CD47 double positive CHO cell pool. The MFI of AbD036 and AbD037 on the PD-L1 and CD47 double positive CHO cell are substantially higher than that on either PD-L1 positive or CD47 positive CHO cells alone, and are also higher than the additive of them. The percentage of stained PD-L1 and CD47 double positive CHO cell by both AbD036 and AbD037 stayed high at the low concentration of 1 nM for AbD036 (FIG. 8A) and 0.1 nM for AbD037 (FIG. 8B). The staining on the double targets positive CHO cell is about 10 fold stronger than that on the single target positive cells.

Therefore, we generated novel bi-specific GCT Abs of Abd036 and AbD037 that can selectively bind PD-L1 and CD47 double positive cells. Since many Cancer cells upregulating both PD-L1 and CD47 to avoid immune surveillance and elimination, our GCT Ab against PD-L1 and CD47 are potential an effective therapeutic drug for many tumor disease by selectively blocking both the PD-L1 and CD47 inhibitory pathways on tumor cells.

These experiments of both Example 1 and 2 demonstrated that the bispecific antibodies generated by our GCT Ab method may, in general, selectively target cells expressing both antigens over cells only express one of the targets. This is significant for antibody drug development against cancers.

Cancer cell are usually over expressing multiple cell surface targets that may also individually present on some normal tissues. The available of a bi-specific GCT-Ab selectively binding cancer cells over normal tissue could substantially reduce the adverse effect, expand the dosing window and improve the overall therapeutic potency and efficacy.

What is claimed is:

1. An engineered bi-specific antibody, comprising:
   (i) a first chain comprising a first antigen binding single domain linked to the N-terminal of CH1 of IgG heavy chain that binds a first target, and having a first affinity in a range between $10^{-5}$ and $10^{-8}$M; and
   (ii) a second chain comprising a second antigen binding single domain linked to the N-terminal of CL of light chain that binds a second target, and having a second affinity in a range between $10^{-5}$ and $10^{-8}$M;
   (iii) a third chain that is same as the first chain;
   (iv) a fourth chain that is the same as the second chain;
   wherein said first chain is linked to said second chain to form a first arm through dimerization between CH1 and CL, said third chain is linked to said fourth chain to form a second arm through dimerization between CH1 and CL,
   wherein said first arm is identical to said second arm, and said first arm and said second arm is linked by the IgG Fc dimerization,
   wherein said first target and second target are both co-localized on a target cell;
   wherein said bi-specific antibody more specifically binds to said target cell than to cells only expressing either said first target or said second target, with an avidity in a range between $10^{-9}$ and $10^{-12}$M;
   wherein said affinity and avidity are measured by ELISA binding activity assay; and
   wherein
   (i) the heavy chain comprises any one of the sequences of SEQ ID No. 2, No. 4, No. 37, No. 41; and
   (ii) the light chain comprises any one of the sequences of SEQ ID No. 6, No. 8, No. 39, No. 43, wherein said antibody binds to Her2 and CD47 double positive target cell; or
   wherein
   (iii) the heavy chain comprises any one of the sequences of SEQ ID No. 6, No. 8, No. 29, No. 33; and
   (iv) the light chain comprises any one of the sequences of SEQ ID No. 10, No. 12, No. 31, No. 35, wherein said antibody binds to PD-L1 and CD47 double positive target cell.

2. The antibody of claim 1, wherein said first target and second target is selected from the group consisting of a tumor target, a disease-specific receptor, and an immune regulatory function target.

3. The antibody of claim 2, wherein said tumor target is Her2.

4. The antibody of claim 2, wherein said immune regulatory function target is PD-L1 or CD47.

5. An engineered tri-specific antibody, comprising:
   (i) a first chain comprising a first antigen binding single domain linked to the N-terminal of CH1 of IgG heavy chain that binds a first target, and having a first affinity in a range between $10^{-5}$ and $10^{-8}$M; and
   (ii) a second chain comprising a second antigen binding single domain linked to the N-terminal of CL of light chain that binds a second target, and having a second affinity in a range between $10^{-5}$ and $10^{-8}$M;
   (iii) a third chain that is same as the first chain;
   (iv) a fourth chain that is the same as the second chain;
   (v) a third antigen binding single domain linked to the C-terminal of CL of light chain that binds a third target, having a third affinity in a range between $10^{-5}$ and $10^{-8}$M;
   wherein said first chain is linked to said second chain to form a first arm through dimerization between CH1 and CL, said third chain is linked to said fourth chain to form a second arm through dimerization between CH1 and CL;
   wherein said first arm is identical to said second arm, and said first arm and said second arm is linked by the IgG Fc dimerization;
   wherein said first target and second target are both co-localized on a same target cell; and
   wherein said tri-specific antibody more specifically bind to said target cell than to cells only expressing either said first target or said second target, with an avidity in a range between $10^{-9}$ and $10^{-12}$M; and wherein said third target is an effector function target; wherein said third antigen binding domain mediates effector cells to the target cell; and
   wherein said affinity and avidity are measured by ELISA binding activity assay,
   wherein
   i) the heavy chain comprises any one of the sequences of SEQ ID No. 2, No. 4, No. 37, No. 41; and
   (ii) the light chain comprises any one of the sequences of SEQ ID No. 6, No. 8, No. 53, No. 55, No. 57, No. 59, wherein said antibody binds to Her2 and CD47 double positive target cell, or wherein
   (iii) the heavy chain comprises any one of the sequences of SEQ ID No. 6, No. 8, No. 29, No. 33; and
   (iv) the light chain comprises any one of the sequences of SEQ ID No. 10, No. 12, No. 45, No. 47, No. 49, No. 51, wherein said antibody binds to PD-L1 and CD47 double positive target cell.

6. The antibody of claim 5, wherein said third target is selected from the group consisting of CD3, CD16a, and CD59.

* * * * *

```
                       SEQUENCE LISTING

<160> NUMBER OF SEQ ID NOS: 69

<210> SEQ ID NO 1
   <211> LENGTH: 360
   <212> TYPE: DNA
   <213> ORGANISM: Artificial Sequence
   <220> FEATURE:
   <223> OTHER INFORMATION: Synthetic polynucleotide

<400> SEQUENCE: 1
gaggtgcagc tggtggagtc tggaggaggc ttggtccagc ctgggggtc cctgagactc      60 tcctgtgcag cctctgggtt caacatcaaa gacacctaca tccactgggt ccgccaggct    120
ccagggaagg agcgggagtg ggtcgcccgg atttatccca aaacggtta cacacggtac     180 gcagactccg tgaagggccg attcaccatc tccagagaca atgccaagga cactgtgtat    240
cttcaaatga acagcctgag agccgaggac acggccgtgt attactgttc ccggtgggga    300
ggggacgggt tctatgctat ggactactgg ggccaaggaa cactggtcac cgtctcgagc    360

<210> SEQ ID NO 2
   <211> LENGTH: 120
   <212> TYPE: PRT
   <213> ORGANISM: Artificial Sequence
   <220> FEATURE:
   <223> OTHER INFORMATION: Synthetic polypeptide

<400> SEQUENCE: 2

Glu Val Gln Leu Val Glu Ser Gly Gly Gly Leu Val Gln Pro Gly Gly
   1               5                   10                  15

Ser Leu Arg Leu Ser Cys Ala Ala Ser Gly Phe Asn Ile Lys Asp Thr
               20                  25                  30

Tyr Ile His Trp Val Arg Gln Ala Pro Gly Lys Glu Arg Glu Trp Val
           35                  40                  45

Ala Arg Ile Tyr Pro Thr Asn Gly Tyr Thr Arg Tyr Ala Asp Ser Val
       50                  55                  60

Lys Gly Arg Phe Thr Ile Ser Arg Asp Asn Ala Lys Asp Thr Val Tyr
   65                  70                  75                  80

Leu Gln Met Asn Ser Leu Arg Ala Glu Asp Thr Ala Val Tyr Tyr Cys
                   85                  90                  95

Ser Arg Trp Gly Gly Asp Gly Phe Tyr Ala Met Asp Tyr Trp Gly Gln
               100                 105                 110

Gly Thr Leu Val Thr Val Ser Ser
           115                 120

<210> SEQ ID NO 3
   <211> LENGTH: 369
   <212> TYPE: DNA
   <213> ORGANISM: Artificial Sequence
   <220> FEATURE:
   <223> OTHER INFORMATION: Synthetic polynucleotide
```

<400> SEQUENCE: 3

```
caggtgcagc tggtgcagtc tgggggagga ttggtgcagg ctgggggctc tctgagactc    60
tcctgtgcag cctctggacg caccttcagt agttatgcca tggcctggtt ccgccaggct   120
ccagggaagg agcgtgagtt tgtagcagct attagctgga gtggtgcaaa catatacgtt   180
gcagactccg tgaagggccg attcaccatc tccagagaca acgccaagga cacggtgtat   240
ctgcaaatga acagcctgaa acctgaggac acggccgttt attactgtgc agtaaagctc   300
ggtttcgcac tgtagaaga aggcagtat gactactggg gccaggggac ccaggtcacc   360
gtctcgagc                                                          369
```

<210> SEQ ID NO 4
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 4

```
Gln Val Gln Leu Val Gln Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Phe Val
        35                  40                  45

Ala Ala Ile Ser Trp Ser Gly Ala Asn Ile Tyr Val Ala Asp Ser Val
    50                  55                  60

Lys Gly Arg Phe Thr Ile Ser Arg Asp Asn Ala Lys Asp Thr Val Tyr
65                  70                  75                  80

Leu Gln Met Asn Ser Leu Lys Pro Glu Asp Thr Ala Val Tyr Tyr Cys
                85                  90                  95

Ala Val Lys Leu Gly Phe Ala Pro Val Glu Glu Arg Gly Tyr Asp Tyr
            100                 105                 110

Trp Gly Gln Gly Thr Gln Val Thr Val Ser Ser
        115                 120
```

<210> SEQ ID NO 5
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 5

```
gaagaggaac tccaggtgat ccagcccgac aagtccgtga gcgtggctgc tggagagagc    60
gccatcctgc actgtaccgt gacctccctg atccctgtgg acccatcca gtggttcaga   120 ggagctggac ctgcaagaga actgatctac aaccagaagg agggacactt ccctagagtg   180
accacagtga gcgagtccac caagcgggag aacatggact tctccatcag catctccaac   240 atcaccctg ctgacgcagg cacctactat tgcgtgaagt tcaggaaggg cagccctgac   300
accgagttca gtccggcgc tggaaccgag ctgagcgtga gagccaagcc c             351
```

<210> SEQ ID NO 6
<211> LENGTH: 117
<212> TYPE: PRT
<213> ORGANISM: Artificial Sequence
<220> FEATURE:

<223> OTHER INFORMATION: Synthetic polypeptide

<400> SEQUENCE: 6

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro
        115

<210> SEQ ID NO 7
<211> LENGTH: 354
<212> TYPE: DNA
<213> ORGANISM: Artificial Sequence
<220> FEATURE:
<223> OTHER INFORMATION: Synthetic polynucleotide

<400> SEQUENCE: 7
gaagaggaac tccaggtgat ccagcccgac aagtccgtga gcgtggctgc tggagagagc    60
gccatcctgc actgtaccgt gacctccctg atccctgtgg acccatcca gtggttcaga    120 ggagctggac ctgcaagaga actgatctac aaccagaagg agggacactt ccctagagtg    180
accacagtga gcgagtccac caagcggaat aacatggact tctccatcag aatcggcaac    240
atcacccctg ctgacgcagg cacctactat tgcgtgaagt tcaggaaggg cagccctgac    300
gatgtcgagt tcaagtccgg cgctggaacc gagctgagcg tgagagccaa gccc          354

<210> SEQ ID NO 8
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 8

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro
        115

<210> SEQ ID NO 9
<211> LENGTH: 378
<212> TYPE: DNA
<213> ORGANISM: Artificial Sequence
<220> FEATURE:
<223> OTHER INFORMATION: Synthetic polynucleotide

<400> SEQUENCE: 9
gactccccag acaggccctg aaccccccc accttctccc cagccctgct cgtggtgacc      60
gaaggggaca cgccaccttc acctgtagc ttctccaaca catcggagag cttcgtgcta    120
aactggtatc gcatgagccc cagcaaccag acggacaagc tggccgcctt ccccgaggac    180
cgcagccagc ccggccagga ctgccgcttc cgtgtcacac aactgcccaa cgggcgtgac    240
ttccacatga gcgtggtcag agcccggcgc aatgacagcg gcacctacct ctgtggagct    300
atctcccggg cccccaaggc gcagatcaaa gagagcctgc gggcagagct gagggtgaca    360
gagagaaggg cagaagtc                                                  378

<210> SEQ ID NO 10
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 10

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Arg Ala Pro Lys Ala Gln Ile Lys Glu Ser
            100                 105                 110

Leu Arg Ala Glu Leu Arg Val Thr Glu Arg Arg Ala Glu Val
        115                 120                 125

<210> SEQ ID NO 11
<211> LENGTH: 378
<212> TYPE: DNA
<213> ORGANISM: Artificial Sequence
<220> FEATURE:
<223> OTHER INFORMATION: Synthetic polynucleotide

<400> SEQUENCE: 11
gactccccag acagaccttg aacccacct accttctccc cagcactgct cgtcgtgacc      60
gaaggagaca cgcaaccttc acctgtagc ttctccaaca catcggagag cttcgtgcta    120

```
aactggtatc gcatgagccc tagcaaccag actgacaagc tggcagcctt ccctgaggac      180
cgcagccagc caggacagga ctgccgcttc cgtgtcacac aactgcccaa cggacgtgac      240
ttccacatga gcgtggtcag agcaagacgc aatgacagcg gcacctacct ctgtggagct      300
atctccctgg ctcccaaggc acagatcaaa gagagcctga gggcagagct gagggtgaca      360
gagagaaggg cagaagtc                                                    378
```

```
<210> SEQ ID NO 12
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 12
```

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val
        115                 120                 125

```
<210> SEQ ID NO 13
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 13
tcgagcgcgt cgacc                                                       15

<210> SEQ ID NO 14
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 14
tcgagccgta cg                                                          12

<210> SEQ ID NO 15
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 15 gcgtcgacc                                                              9
```

<210> SEQ ID NO 16
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 16
gcgtcgaccg gcggtggtgg gtcg                                  24

<210> SEQ ID NO 17
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 17
gcgtcgaccg gcggaggtgg gtccggggga ggcggaagc                  39

<210> SEQ ID NO 18
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 18
gcgtcgaccg gcggaggtgg gtccggggga ggcggaagcg gagggggcgg atct    54

<210> SEQ ID NO 19
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 19
gcgtcgaccg gcggaggtgg gtccggggga ggcggaagcg gagggggcgg atctggaggt    60
agc                                                         63

<210> SEQ ID NO 20
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 20
tcgagcgcgt cgaccccact cgga                                  24

<210> SEQ ID NO 21
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 21
tcgagcgcgt cgaccccact cggagacacc aca                        33

<210> SEQ ID NO 22
<211> LENGTH: 45
<212> TYPE: DNA

<213> ORGANISM: Artificial Sequence
<220> FEATURE:
<223> OTHER INFORMATION: Synthetic polynucleotide

<400> SEQUENCE: 22
tcgagcgcgt cgaccccact cggagacacc acacacacca gccct          45

<210> SEQ ID NO 23
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 23
tcgagcgcgt cgaccccact cggagacacc acacacacca gccctagatc tcca          54

<210> SEQ ID NO 24
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 24
tcgagcgcgt cgaccagccc tagatctcca gagcccaaga gctccgacac accccacct          60

<210> SEQ ID NO 25
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 25
tcgagcgata agacccacac t          21

<210> SEQ ID NO 26
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 26
tcgagcgata agacccacac tgcgtcgacc          30

<210> SEQ ID NO 27
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 27
tcgagcgaca agacacgtac ggcgtcgacc          30

<210> SEQ ID NO 28
<211> LENGTH: 1350
<212> TYPE: DNA
<213> ORGANISM: Artificial Sequence
<220> FEATURE:
<223> OTHER INFORMATION: Synthetic polynucleotide

<400> SEQUENCE: 28

```
gaagaggaac tccaggtgat ccagcccgac aagtccgtga gcgtggctgc tggagagagc      60
gccatcctgc actgtaccgt gacctccctg atccctgtgg gacccatcca gtggttcaga     120
ggagctggac ctgcaagaga actgatctac aaccagaagg agggacactt ccctagagtg     180
accacagtga gcgagtccac caagcggaat aacatggact tctccatcag aatcggcaac     240
atcacccctg ctgacgcagg cacctactat tgcgtgaagt tcaggaaggg cagccctgac     300
gatgtcgagt tcaagtccgg cgctggaacc gagctgagcg tgagagccaa gccctcgagc     360
gcgtcgacca agggcccatc ggtcttcccg ctagcaccct cctccaagag cacctctggg     420
ggcacagcgg ccctgggctg cctggtcaag gactacttcc ccgaacctgt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaagc tgctggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gggtggtcag cgtcctcacc gtcctgcacc aggactggct gaatggcaag     960
gagtacaagt gcaaggtctc caacaaagcc ctcggagccc ccatcgagaa aaccatctcc    1020
aaagccaaag ggcagccccg agaaccacag gtgtacaccc tgcccccatc cagggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tcccgggaaa                                      1350
```

<210> SEQ ID NO 29
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 29

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110
```

Ser Val Arg Ala Lys Pro Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 30
<211> LENGTH: 705
<212> TYPE: DNA
<213> ORGANISM: Artificial Sequence
<220> FEATURE:
<223> OTHER INFORMATION: Synthetic polynucleotide

<400> SEQUENCE: 30

```
gactccccag acaggccctg aaccccccc accttctccc cagccctgct cgtggtgacc    60
gaagggaca acgccaccttc cacctgtagc ttctccaaca catcggagag cttcgtgcta   120
aactggtatc gcatgagccc cagcaaccag acggacaagc tggccgcctt ccccgaggac   180
cgcagccagc ccggccagga ctgccgcttc cgtgtcacac aactgcccaa cgggcgtgac   240
ttccacatga gcgtggtcag agcccggcgc aatgacagcg gcacctacct ctgtggagct   300
atctcccggg ccccccaaggc gcagatcaaa gagagcctgc gggcagagct gagggtgaca   360
gagagaaggg cagaagtctc gagccgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag acagcacct acagcctcag cagcaccctg   600
acgctgagca agcagactac gagaaacac aaagtctacg cctgcgaagt cacccatcag   660
ggcctgagct cgcccgtcac aaagagcttc aacaggggag agtgt              705
```

<210> SEQ ID NO 31
<211> LENGTH: 235
<212> TYPE: PRT
<213> ORGANISM: Artificial Sequence
<220> FEATURE:
<223> OTHER INFORMATION: Synthetic polypeptide

<400> SEQUENCE: 31

```
Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Arg Ala Pro Lys Ala Gln Ile Lys Glu Ser
            100                 105                 110

Leu Arg Ala Glu Leu Arg Val Thr Glu Arg Arg Ala Glu Val Ser Ser
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220
```

Pro Val Thr Lys Ser Phe Asn Arg Gly Glu Cys
225                 230                 235

<210> SEQ ID NO 32
<211> LENGTH: 1347
<212> TYPE: DNA
<213> ORGANISM: Artificial Sequence
<220> FEATURE:
<223> OTHER INFORMATION: Synthetic polynucleotide

<400> SEQUENCE: 32

| | | | | | |
|---|---|---|---|---|---|
| gaagaggaac | tccaggtgat | ccagcccgac | aagtccgtga | gcgtggctgc | tggagagagc | 60 |
| gccatcctgc | actgtaccgt | gacctccctg | atccctgtgg | gacccatcca | gtggttcaga | 120 |
| ggagctggac | ctgcaagaga | actgatctac | aaccagaagg | agggacactt | ccctagagtg | 180 |
| accacagtga | gcgagtccac | caagcgggag | aacatggact | tctccatcag | catctccaac | 240 |
| atcacccctg | ctgacgcagg | cacctactat | tgcgtgaagt | tcaggaaggg | cagccctgac | 300 |
| accgagttca | gtccggcgc | tggaaccgag | ctgagcgtga | gagccaagcc | tcgagcgcg | 360 |
| tcgaccaagg | gcccatcggt | cttcccgcta | gcaccctcct | ccaagagcac | ctctggggc | 420 |
| acagcggccc | tgggctgcct | ggtcaaggac | tacttccccg | aacctgtgac | ggtgtcgtgg | 480 |
| aactcaggcg | ccctgaccag | cggcgtgcac | accttcccgg | ctgtcctaca | gtcctcagga | 540 |
| ctctactccc | tcagcagcgt | ggtgaccgtg | ccctccagca | gcttgggcac | ccagacctac | 600 |
| atctgcaacg | tgaatcacaa | gcccagcaac | accaaggtgg | acaagaaagt | tgagcccaaa | 660 |
| tcttgtgaca | aaactcacac | atgcccaccg | tgcccagcac | ctgaagctgc | tgggggaccg | 720 |
| tcagtcttcc | tcttcccccc | aaaacccaag | gacaccctca | tgatctcccg | gacccctgag | 780 |
| gtcacatgcg | tggtggtgga | cgtgagccac | gaagaccctg | aggtcaagtt | caactggtac | 840 |
| gtggacggcg | tggaggtgca | taatgccaag | acaaagccgc | gggaggagca | gtacaacagc | 900 |
| acgtaccggg | tggtcagcgt | cctcaccgtc | ctgcaccagg | actggctgaa | tggcaaggag | 960 |
| tacaagtgca | aggtctccaa | caaagccctc | ggagccccca | tcgagaaaac | catctccaaa | 1020 |
| gccaaagggc | agccccgaga | accacaggtg | tacaccctgc | ccccatccag | ggatgagctg | 1080 |
| accaagaacc | aggtcagcct | gacctgcctg | gtcaaaggct | tctatcccag | cgacatcgcc | 1140 |
| gtggagtggg | agagcaatgg | gcagccggag | aacaactaca | agaccacgcc | tcccgtgctg | 1200 |
| gactccgacg | gctccttctt | cctctacagc | aagctcaccg | tggacaagag | caggtggcag | 1260 |
| caggggaacg | tcttctcatg | ctccgtgatg | catgaggctc | tgcacaacca | ctacacgcag | 1320 |
| aagagcctct | ccctgtctcc | cgggaaa | | | | 1347 |

<210> SEQ ID NO 33
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 33

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

-continued

Ile Tyr Asn Gln Lys Glu Gly His Phe Pro Arg Val Thr Val Ser
    50              55                  60

Glu Ser Thr Lys Arg Glu Asn Met Asp Phe Ser Ile Ser Ile Ser Asn
65              70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
    435                 440                 445

Lys

```
<210> SEQ ID NO 34
<211> LENGTH: 705
<212> TYPE: DNA
<213> ORGANISM: Artificial Sequence
<220> FEATURE:
<223> OTHER INFORMATION: Synthetic polynucleotide

<400> SEQUENCE: 34
gactccccag acagaccttg aacccacct accttctccc cagcactgct cgtcgtgacc      60
gaaggagaca acgcaacctt cacctgtagc ttctccaaca catcggagag cttcgtgcta     120
aactggtatc gcatgagccc tagcaaccag actgacaagc tggcagcctt ccctgaggac     180
cgcagccagc caggacagga ctgccgcttc cgtgtcacac aactgcccaa cggacgtgac     240
ttccacatga gcgtggtcag agcaagacgc aatgacagcg gcacctacct ctgtggagct     300
atctccctgg ctcccaaggc acagatcaaa gagagcctga gggcagagct gagggtgaca     360
gagagaaggg cagaagtctc gagccgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt                     705

<210> SEQ ID NO 35
<211> LENGTH: 235
<212> TYPE: PRT
<213> ORGANISM: Artificial Sequence
<220> FEATURE:
<223> OTHER INFORMATION: Synthetic polypeptide

<400> SEQUENCE: 35

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Ser Ser
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190
```

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 36
<211> LENGTH: 1350
<212> TYPE: DNA
<213> ORGANISM: Artificial Sequence
<220> FEATURE:
<223> OTHER INFORMATION: Synthetic polynucleotide

<400> SEQUENCE: 36
gaggtgcagc tggtggagtc tggaggaggc ttggtccagc ctggggggtc cctgagactc      60
tcctgtgcag cctctgggtt caacatcaaa gacacctaca tccactgggt ccgccaggct     120
ccagggaagg agcgggagtg ggtcgcccgg atttatccca caaacggtta cacacggtac     180
gcagactccg tgaagggccg attcaccatc tccagagaca atgccaagga cactgtgtat     240
cttcaaatga acagcctgag agccgaggac acggccgtgt attactgttc ccggtgggga     300
ggggacgggt tctatgctat ggactactgg ggccaaggaa cactggtcac cgtctcgagc     360
gcgtcgacca agggcccatc ggtcttcccg ctagcaccct cctccaagag cacctctggg     420
ggcacagcgg ccctgggctg cctggtcaag gactacttcc ccgaacctgt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggggga    720 ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gggtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc cagggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggaaa                                      1350

<210> SEQ ID NO 37
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 37

Glu Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Glu Arg Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Arg Asp Asn Ala Lys Asp Thr Val Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445
Gly Lys
    450

<210> SEQ ID NO 38
<211> LENGTH: 684
<212> TYPE: DNA
<213> ORGANISM: Artificial Sequence
<220> FEATURE:
<223> OTHER INFORMATION: Synthetic polynucleotide

<400> SEQUENCE: 38
gaagaggaac tccaggtgat ccagcccgac aagtccgtga gcgtggctgc tggagagagc      60
gccatcctgc actgtaccgt gacctccctg atccctgtgg gacccatcca gtggttcaga     120
ggagctggac tgcaagaga actgatctac aaccagaagg agggacactt ccctagagtg     180
accacagtga gcgagtccac caagcggaat aacatggact ctccatcag aatcggcaac     240 atcaccctg ctgacgcagg cacctactat tgcgtgaagt tcaggaaggg cagccctgac      300
gatgtcgagt tcaagtccgg cgctggaacc gagctgagcg tgagagccaa gccctcgagc     360
cgtacggtgg ctgcaccatc tgtcttcatc ttcccgccat ctgatgagca gttgaaatct     420
ggaactgcct ctgttgtgtg cctgctgaat aacttctatc ccagagaggc caaagtacag     480
tggaaggtgg ataacgccct ccaatcgggt aactcccagg agagtgtcac agagcaggac     540
agcaaggaca gcacctacag cctcagcagc accctgacgc tgagcaaagc agactacgag     600
aaacacaaag tctacgcctg cgaagtcacc catcagggcc tgagctcgcc cgtcacaaag     660
agcttcaaca ggggagagtg ttag                                           684

<210> SEQ ID NO 39
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 39

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Arg Thr Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
            165                 170                 175

Thr Glu Gln Asp Ser Lys Asp Ser Thr Tyr Ser Leu Ser Ser Thr Leu
        180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 40
<211> LENGTH: 1359
<212> TYPE: DNA
<213> ORGANISM: Artificial Sequence
<220> FEATURE:
<223> OTHER INFORMATION: Synthetic polynucleotide

<400> SEQUENCE: 40
caggtgcagc tggtgcagtc tggggagga ttggtgcagg ctgggggctc tctgagactc      60
tcctgtgcag cctctggacg caccttcagt agttatgcca tggcctggtt ccgccaggct    120
ccagggaagg agcgtgagtt tgtagcagct attagctgga gtggtgcaaa catatacgtt    180
gcagactccg tgaagggccg attcaccatc tccagagaca cgccaagga cacggtgtat    240 ctgcaaatga acagcctgaa acctgaggac acggccgttt attactgtgc agtaaagctc    300
ggtttcgcac ctgtagaaga aaggcagtat gactactggg gccaggggac ccaggtcacc    360
gtctcgagcg cgtcgaccaa gggcccatcg gtcttcccgc tagcaccctc ctccaagagc    420
acctctgggg gcacagcggc cctgggctgc ctggtcaagg actacttccc cgaacctgtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaaa    660
gttgagccca aatcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg ggtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
agggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtga tgcatgaggc tctgcacaac   1320
cactacacgc agaagagcct ctccctgtct ccgggaaa                           1359

<210> SEQ ID NO 41
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 41

```
Gln Val Gln Leu Val Gln Ser Gly Gly Gly Leu Val Gln Ala Gly Gly
  1               5                  10                  15

Ser Leu Arg Leu Ser Cys Ala Ala Ser Gly Arg Thr Phe Ser Ser Tyr
             20                  25                  30

Ala Met Ala Trp Phe Arg Gln Ala Pro Gly Lys Glu Arg Glu Phe Val
         35                  40                  45

Ala Ala Ile Ser Trp Ser Gly Ala Asn Ile Tyr Val Ala Asp Ser Val
     50                  55                  60

Lys Gly Arg Phe Thr Ile Ser Arg Asp Asn Ala Lys Asp Thr Val Tyr
 65                  70                  75                  80

Leu Gln Met Asn Ser Leu Lys Pro Glu Asp Thr Ala Val Tyr Tyr Cys
                 85                  90                  95

Ala Val Lys Leu Gly Phe Ala Pro Val Glu Arg Gln Tyr Asp Tyr
            100                 105                 110

Trp Gly Gln Gly Thr Gln Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 42
<211> LENGTH: 678
<212> TYPE: DNA
<213> ORGANISM: Artificial Sequence
<220> FEATURE:
<223> OTHER INFORMATION: Synthetic polynucleotide

<400> SEQUENCE: 42
gaagaggaac tccaggtgat ccagcccgac aagtccgtga gcgtggctgc tggagagagc        60
gccatcctgc actgtaccgt gacctccctg atccctgtgg acccatcca gtggttcaga       120 ggagctggac ctgcaagaga actgatctac aaccagaagg agggacactt ccctagagtg       180
accacagtga gcgagtccac caagcgggag aacatggact tctccatcag catctccaac       240
atcacccctg ctgacgcagg cacctactat tgcgtgaagt tcaggaaggg cagccctgac       300
accgagttca gtccggcgc tggaaccgag ctgagcgtga gagccaagcc ctcgagccgt       360
acggtggctg caccatctgt cttcatcttc ccgccatctg atgagcagtt gaaatctgga       420
actgcctctg ttgtgtgcct gctgaataac ttctatccca gagaggccaa agtacagtgg       480
aaggtggata acgccctcca atcgggtaac tcccaggaga gtgtcacaga gcaggacagc       540
aaggacagca cctacagcct cagcagcacc ctgacgctga gcaaagcaga ctacgagaaa       600
cacaaagtct acgcctgcga agtcacccat cagggcctga gctcgcccgt cacaaagagc       660
ttcaacaggg gagagtgt                                                     678

<210> SEQ ID NO 43
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 43

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110
```

```
Val Arg Ala Lys Pro Ser Ser Arg Thr Val Ala Ala Pro Ser Val Phe
            115                 120                 125

Ile Phe Pro Pro Ser Asp Glu Gln Leu Lys Ser Gly Thr Ala Ser Val
        130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225

<210> SEQ ID NO 44
<211> LENGTH: 1098
<212> TYPE: DNA
<213> ORGANISM: Artificial Sequence
<220> FEATURE:
<223> OTHER INFORMATION: Synthetic polynucleotide

<400> SEQUENCE: 44
gactccccag acaggccctg aaccccccc accttctccc cagccctgct cgtggtgacc      60 gaagggagaca acgccacctt cacctgtagc ttctccaaca tcggagag cttcgtgcta    120 aactggtatc gcatgagccc cagcaaccag acggacaagc tggccgcctt ccccgaggac    180
cgcagccagc ccggccagga ctgccgcttc cgtgtcacac aactgcccaa cgggcgtgac    240
ttccacatga gcgtggtcag agcccggcgc aatgacagcg gcacctacct ctgtggagct    300
atctcccggg cccccaaggc gcagatcaaa gagagcctgc gggcagagct gagggtgaca    360
gagagaaggg cagaagtctc gagccgtacg gtggctgcac atctgtctt catcttcccg    420 ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac cgagaaacac aaagtctacg cctgcgaagt cacccatcag    660
ggcctgagct cgcccgtcac aaagagcttc aacaggggag agtgtaccgt cctaggtcag    720
cccaaggcgg ccgctgaggt gcagctggtg agtctgggg gaggcttggt acagcctggg    780
gggtccctga ctctcctg tgcagcctct ggattcacct ttgacgacta tgcatgagc    840 tgggtccgcc aggctccagg gaagtggctg gagtgggtct cagatattag ctggaatggt    900
ggtagcacat actacgcaga ctccgtgaag gccggttca ccatctccag agacaatgcc    960
gagaacacgc tgtatctgca aatgaacagc ctgaaacctg acgacacggc cgtgtattac   1020
tgtgcgaaaa tgggtgaagg gggatggggt gcaaatgact actggggcca ggggacccag   1080
gtcaccgtgt cctcataa                                                  1098

<210> SEQ ID NO 45
<211> LENGTH: 365
<212> TYPE: PRT
<213> ORGANISM: Artificial Sequence
<220> FEATURE:
```

<223> OTHER INFORMATION: Synthetic polypeptide

<400> SEQUENCE: 45

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Arg Ala Pro Lys Ala Gln Ile Lys Glu Ser
            100                 105                 110

Leu Arg Ala Glu Leu Arg Val Thr Glu Arg Arg Ala Glu Val Ser Ser
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys Thr Val Leu Gly Gln
225                 230                 235                 240

Pro Lys Ala Ala Ala Glu Val Gln Leu Val Glu Ser Gly Gly Gly Leu
                245                 250                 255

Val Gln Pro Gly Gly Ser Leu Arg Leu Ser Cys Ala Ala Ser Gly Phe
            260                 265                 270

Thr Phe Asp Asp Tyr Gly Met Ser Trp Val Arg Gln Ala Pro Gly Lys
        275                 280                 285

Trp Leu Glu Trp Val Ser Asp Ile Ser Trp Asn Gly Ser Thr Tyr
    290                 295                 300

Tyr Ala Asp Ser Val Lys Gly Arg Phe Thr Ile Ser Arg Asp Asn Ala
305                 310                 315                 320

Glu Asn Thr Leu Tyr Leu Gln Met Asn Ser Leu Lys Pro Asp Asp Thr
                325                 330                 335

Ala Val Tyr Tyr Cys Ala Lys Met Gly Glu Gly Gly Trp Gly Ala Asn
            340                 345                 350

Asp Tyr Trp Gly Gln Gly Thr Gln Val Thr Val Ser Ser
        355                 360                 365

<210> SEQ ID NO 46
<211> LENGTH: 1095
<212> TYPE: DNA
<213> ORGANISM: Artificial Sequence
<220> FEATURE:

<223> OTHER INFORMATION: Synthetic polynucleotide

<400> SEQUENCE: 46

```
gactccccag acaggccctg gaaccccccc accttctccc cagccctgct cgtggtgacc      60
gaagggggaca cgccaccttt cacctgtagc ttctccaaca catcggagag cttcgtgcta    120
aactggtatc gcatgagccc cagcaaccag acggacaagc tggccgcctt ccccgaggac    180
cgcagccagc ccggccagga ctgccgcttc cgtgtcacac aactgcccaa cgggcgtgac    240
ttccacatga gcgtggtcag agcccggcgc aatgacagcg gcacctacct ctgtggagct    300
atctcccggg cccccaaggc gcagatcaaa gagagcctgc gggcagagct gagggtgaca    360
gagagaaggg cagaagtctc gagccgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgtaccgt cctaggtcag    720
cccaaggcgg ccgctgaggt gcagctggtg gagtctgggg gaggcttagt gcagcctggg    780
gagtctctga cactctcctg tgtagttgct ggaagcatct tcagcttcgc catgagctgg    840
tatcgccagg ctccaggaaa agagcgcgaa ttggtcgcac gtattggttc ggatgatcgg    900
gtaacctacg cagattccgt gaagggccga tttaccatct ccagagacaa catcaagcgc    960
acggcgggcc tgcagatgaa cagcctgaaa cctgaggaca cggccgtcta ctactgcaat   1020
gcccaaacag atttgaggga ttggactgtg cgagagtact ggggccaggg gacccaggtc   1080
accgtctcct cataa                                                    1095
```

<210> SEQ ID NO 47
<211> LENGTH: 364
<212> TYPE: PRT
<213> ORGANISM: Artificial Sequence
<220> FEATURE:
<223> OTHER INFORMATION: Synthetic polynucleotide

<400> SEQUENCE: 47

```
Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Arg Ala Pro Lys Ala Gln Ile Lys Glu Ser
            100                 105                 110

Leu Arg Ala Glu Leu Arg Val Thr Glu Arg Arg Ala Glu Val Ser Ser
        115                 120                 125

Arg Thr Val Ala Ala Pro Ser Val Phe Ile Phe Pro Pro Ser Asp Glu
    130                 135                 140
```

```
Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys Thr Val Leu Gly Gln
225                 230                 235                 240

Pro Lys Ala Ala Ala Glu Val Gln Leu Val Glu Ser Gly Gly Gly Leu
                245                 250                 255

Val Gln Pro Gly Glu Ser Leu Thr Leu Ser Cys Val Val Ala Gly Ser
            260                 265                 270

Ile Phe Ser Phe Ala Met Ser Trp Tyr Arg Gln Ala Pro Gly Lys Glu
        275                 280                 285

Arg Glu Leu Val Ala Arg Ile Gly Ser Asp Asp Arg Val Thr Tyr Ala
    290                 295                 300

Asp Ser Val Lys Gly Arg Phe Thr Ile Ser Arg Asp Asn Ile Lys Arg
305                 310                 315                 320

Thr Ala Gly Leu Gln Met Asn Ser Leu Lys Pro Glu Asp Thr Ala Val
                325                 330                 335

Tyr Tyr Cys Asn Ala Gln Thr Asp Leu Arg Asp Trp Thr Val Arg Glu
            340                 345                 350

Tyr Trp Gly Gln Gly Thr Gln Val Thr Val Ser Ser
        355                 360
```

<210> SEQ ID NO 48
<211> LENGTH: 1095
<212> TYPE: DNA
<213> ORGANISM: Artificial Sequence
<220> FEATURE:
<223> OTHER INFORMATION: Synthetic polynucleotide

<400> SEQUENCE: 48

```
gactccccag acagaccttg aacccaccct accttctccc cagcactgct cgtcgtgacc   60
gaaggagaca cgcaaccctt cacctgtagc ttctccaaca catcggagag cttcgtgcta  120
aactggtatc gcatgagccc tagcaaccag actgacaagc tggcagcctt ccctgaggac  180
cgcagccagc caggacagga ctgccgcttc cgtgtcacac aactgcccaa cggacgtgac  240
ttccacatga gcgtggtcag agcaagacgc aatgacagcg gcacctacct ctgtggagct  300
atctccctgg ctcccaaggc acagatcaaa gagagcctga ggcagagct gagggtgaca   360
gagagaaggg cagaagtctc gagccgtacg gtggctgcac catctgtctt catcttcccg  420
ccatctgatg agcagttgaa atctggaact gcctctgttg tgtgcctgct gaataacttc  480
tatcccagag aggccaaagt acagtggaag gtggataacg ccctccaatc gggtaactcc  540
caggagagtg tcacagagca ggacagcaag acagcacct acagcctcag cagcaccctg  600
acgctgagca agcagactac gagaaacac aaagtctacg cctgcgaagt cacccatcag  660
ggcctgagct cgcccgtcac aaagagcttc aacaggggag agtgtaccgt cctaggtcag  720
cccaaggcgg ccgctgaggt gcagctggtg agtctgggg gaggcttggt acagcctggg  780
gggtccctga gactctcctg tgcagcctct ggattcacct ttgacgacta tggcatgagc  840
```

```
tgggtccgcc aggctccagg gaagtggctg gagtgggtct cagatattag ctggaatggt    900
ggtagcacat actacgcaga ctccgtgaag gccggttca ccatctccag agacaatgcc     960
gagaacacgc tgtatctgca aatgaacagc ctgaaacctg acgacacggc cgtgtattac   1020
tgtgcgaaaa tgggtgaagg gggatggggt gcaaatgact actggggcca ggggacccag   1080
gtcaccgtgt cctca                                                    1095
```

<210> SEQ ID NO 49
<211> LENGTH: 365
<212> TYPE: PRT
<213> ORGANISM: Artificial Sequence
<220> FEATURE:
<223> OTHER INFORMATION: Synthetic polypeptide

<400> SEQUENCE: 49

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
                100                 105                 110

Leu Arg Ala Glu Leu Arg Val Thr Glu Arg Arg Ala Glu Val Ser Ser
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys Thr Val Leu Gly Gln
225                 230                 235                 240

Pro Lys Ala Ala Ala Glu Val Gln Leu Val Glu Ser Gly Gly Gly Leu
                245                 250                 255

Val Gln Pro Gly Gly Ser Leu Arg Leu Ser Cys Ala Ala Ser Gly Phe
            260                 265                 270

Thr Phe Asp Asp Tyr Gly Met Ser Trp Val Arg Gln Ala Pro Gly Lys
        275                 280                 285

Trp Leu Glu Trp Val Ser Asp Ile Ser Trp Asn Gly Gly Ser Thr Tyr
    290                 295                 300
```

Tyr Ala Asp Ser Val Lys Gly Arg Phe Thr Ile Ser Arg Asp Asn Ala
305                 310                 315                 320

Glu Asn Thr Leu Tyr Leu Gln Met Asn Ser Leu Lys Pro Asp Asp Thr
            325                 330                 335

Ala Val Tyr Tyr Cys Ala Lys Met Gly Glu Gly Gly Trp Gly Ala Asn
        340                 345                 350

Asp Tyr Trp Gly Gln Gly Thr Gln Val Thr Val Ser Ser
        355                 360                 365

<210> SEQ ID NO 50
<211> LENGTH: 1092
<212> TYPE: DNA
<213> ORGANISM: Artificial Sequence
<220> FEATURE:
<223> OTHER INFORMATION: Synthetic polynucleotide

<400> SEQUENCE: 50
gactccccag acagaccttg aacccacct accttctccc cagcactgct cgtcgtgacc      60
gaaggagaca acgcaacctt cacctgtagc ttctccaaca catcggagag cttcgtgcta     120
aactggtatc gcatgagccc tagcaaccag actgacaagc tggcagcctt ccctgaggac     180
cgcagccagc caggacagga ctgccgcttc cgtgtcacac aactgcccaa cggacgtgac     240
ttccacatga gcgtggtcag agcaagacgc aatgacagcg gcacctacct ctgtggagct     300
atctccctgg ctcccaaggc acagatcaaa gagagcctga gggcagagct gagggtgaca     360
gagagaaggg cagaagtctc gagccgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgtaccgt cctaggtcag     720
cccaaggcgg ccgctgaggt gcagctggtg gagtctgggg gaggcttagt gcagcctggg     780
gagtctctga cactctcctg tgtagttgct ggaagcatct tcagcttcgc catgagctgg     840
tatcgccagg ctccaggaaa agagcgcgaa ttggtcgcac gtattggttc ggatgatcgg     900
gtaacctacg cagattccgt gaagggccga tttaccatct ccagagacaa catcaagcgc     960
acggcgggcc tgcagatgaa cagcctgaaa cctgaggaca cggccgtcta ctactgcaat    1020
gcccaaacag atttgaggga ttggactgtg cgagagtact ggggccaggg acccaggtc    1080 accgtctcct ca                                                        1092

<210> SEQ ID NO 51
<211> LENGTH: 364
<212> TYPE: PRT
<213> ORGANISM: Artificial Sequence
<220> FEATURE:
<223> OTHER INFORMATION: Synthetic polypeptide

<400> SEQUENCE: 51

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
                100                 105                 110

Leu Arg Ala Glu Leu Arg Val Thr Glu Arg Arg Ala Glu Val Ser Ser
            115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys Thr Val Leu Gly Gln
225                 230                 235                 240

Pro Lys Ala Ala Ala Glu Val Gln Leu Val Glu Ser Gly Gly Gly Leu
                245                 250                 255

Val Gln Pro Gly Glu Ser Leu Thr Leu Ser Cys Val Val Ala Gly Ser
                260                 265                 270

Ile Phe Ser Phe Ala Met Ser Trp Tyr Arg Gln Ala Pro Gly Lys Glu
            275                 280                 285

Arg Glu Leu Val Ala Arg Ile Gly Ser Asp Asp Arg Val Thr Tyr Ala
            290                 295                 300

Asp Ser Val Lys Gly Arg Phe Thr Ile Ser Arg Asp Asn Ile Lys Arg
305                 310                 315                 320

Thr Ala Gly Leu Gln Met Asn Ser Leu Lys Pro Glu Asp Thr Ala Val
                325                 330                 335

Tyr Tyr Cys Asn Ala Gln Thr Asp Leu Arg Asp Trp Thr Val Arg Glu
                340                 345                 350

Tyr Trp Gly Gln Gly Thr Gln Val Thr Val Ser Ser
            355                 360

<210> SEQ ID NO 52
<211> LENGTH: 1077
<212> TYPE: DNA
<213> ORGANISM: Artificial Sequence
<220> FEATURE:
<223> OTHER INFORMATION: Synthetic polynucleotide

<400> SEQUENCE: 52
gaagaggaac tccaggtgat ccagcccgac aagtccgtga gcgtggctgc tggagagagc      60
gccatcctgc actgtaccgt gacctccctg atccctgtgg acccatcca gtggttcaga     120 ggagctggac ctgcaagaga actgatctac aaccagaagg agggacactt ccctagagtg     180
accacagtga gcgagtccac caagcggaat aacatggact ctccatcag aatcggcaac     240

-continued

```
atcacccctg ctgacgcagg cacctactat tgcgtgaagt tcaggaaggg cagccctgac    300
gatgtcgagt tcaagtccgg cgctggaacc gagctgagcg tgagagccaa gccctcgagc    360
tcgagccgta cggtggctgc accatctgtc ttcatcttcc cgccatctga tgagcagttg    420
aaatctggaa ctgcctctgt tgtgtgcctg ctgaataact tctatcccag agaggccaaa    480
gtacagtgga aggtggataa cgccctccaa tcgggtaact cccaggagag tgtcacagag    540
caggacagca aggacagcac ctacagcctc agcagcaccc tgacgctgag caaagcagac    600
tacgagaaac acaaagtcta cgcctgcgaa gtcacccatc agggcctgag ctcgcccgtc    660
acaaagagct tcaacagggg agagtgtacc gtcctaggtc agcccaaggc ggccgctgag    720
gtgcagctgg tggagtctgg gggaggcttg gtacagcctg gggggtccct gagactctcc    780
tgtgcagcct ctggattcac ctttgacgac tatggcatga gctgggtccg ccaggctcca    840
gggaagtggc tggagtgggt ctcagatatt agctggaatg gtggtagcac atactacgca    900
gactccgtga agggccggtt caccatctcc agagacaatg ccgagaacac gctgtatctg    960
caaatgaaca gcctgaaacc tgacgacacg gccgtgtatt actgtgcgaa aatgggtgaa   1020
gggggatggg gtgcaaatga ctactggggc caggggaccc aggtcaccgt gtcctca      1077
```

<210> SEQ ID NO 53
<211> LENGTH: 359
<212> TYPE: PRT
<213> ORGANISM: Artificial Sequence
<220> FEATURE:
<223> OTHER INFORMATION: Synthetic polypeptide

<400> SEQUENCE: 53

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ser Ser Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220
```

```
Asn Arg Gly Glu Cys Thr Val Leu Gly Gln Pro Lys Ala Ala Glu
225                 230                 235                 240

Val Gln Leu Val Glu Ser Gly Gly Gly Leu Val Gln Pro Gly Gly Ser
            245                 250                 255

Leu Arg Leu Ser Cys Ala Ala Ser Gly Phe Thr Phe Asp Asp Tyr Gly
        260                 265                 270

Met Ser Trp Val Arg Gln Ala Pro Gly Lys Trp Leu Glu Trp Val Ser
    275                 280                 285

Asp Ile Ser Trp Asn Gly Ser Thr Tyr Tyr Ala Asp Ser Val Lys
290                 295                 300

Gly Arg Phe Thr Ile Ser Arg Asp Asn Ala Glu Asn Thr Leu Tyr Leu
305                 310                 315                 320

Gln Met Asn Ser Leu Lys Pro Asp Asp Thr Ala Val Tyr Tyr Cys Ala
            325                 330                 335

Lys Met Gly Glu Gly Gly Trp Gly Ala Asn Asp Tyr Trp Gly Gln Gly
        340                 345                 350

Thr Gln Val Thr Val Ser Ser
        355
```

<210> SEQ ID NO 54
<211> LENGTH: 1074
<212> TYPE: DNA
<213> ORGANISM: Artificial Sequence
<220> FEATURE:
<223> OTHER INFORMATION: Synthetic polynucleotide

<400> SEQUENCE: 54

```
gaagaggaac tccaggtgat ccagcccgac aagtccgtga gcgtggctgc tggagagagc      60
gccatcctgc actgtaccgt gacctccctg atccctgtgg acccatcca gtggttcaga     120
ggagctggac ctgcaagaga actgatctac aaccagaagg agggacactt ccctagagtg     180
accacagtga gcgagtccac caagcggaat aacatggact ctccatcag aatcggcaac     240
atcaccctg ctgacgcagg cacctactat tgcgtgaagt tcaggaaggg cagccctgac     300
gatgtcgagt tcaagtccgg cgctggaacc gagctgagcg tgagagccaa gccctcgagc     360
tcgagccgta cggtggctgc accatctgtc ttcatcttcc cgccatctga tgagcagttg     420
aaatctggaa ctgcctctgt tgtgtgcctg ctgaataact tctatcccag agaggccaaa     480
gtacagtgga aggtggataa cgccctccaa tcgggtaact cccaggagag tgtcacagag     540
caggacagca aggacagcac ctacagcctc agcagcaccc tgacgctgag caaagcagac     600
tacgagaaac acaaagtcta cgcctgcgaa gtcacccatc agggcctgag ctcgcccgtc     660
acaaagagct tcaacagggg agagtgtacc gtcctaggtc agcccaaggc ggccgctgag     720
gtgcagctgg tggagtctgg gggaggctta gtgcagcctg gggagtctct gacactctcc     780
tgtgtagttg ctggaagcat cttcagcttc gccatgagct ggtatcgcca ggctccagga     840
aaagagcgcg aattggtcgc acgtattggt tcggatgatc gggtaaccta cgcagattcc     900
gtgaagggcc gatttaccat ctccagagac aacatcaagc gcacggcggg cctgcagatg     960
aacagcctga aacctgagga cacggccgtc tactactgca atgcccaaac agatttgagg    1020
gattggactg tgcgagagta ctggggccag gggacccagg tcaccgtctc ctca          1074
```

<210> SEQ ID NO 55
<211> LENGTH: 358
<212> TYPE: PRT
<213> ORGANISM: Artificial Sequence
<220> FEATURE:
<223> OTHER INFORMATION: Synthetic polypeptide

<400> SEQUENCE: 55

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ser Ser Arg Thr Val Ala Ala Pro
        115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys Thr Val Leu Gly Gln Pro Lys Ala Ala Ala Glu
225                 230                 235                 240

Val Gln Leu Val Glu Ser Gly Gly Gly Leu Val Gln Pro Gly Glu Ser
                245                 250                 255

Leu Thr Leu Ser Cys Val Val Ala Gly Ser Ile Phe Ser Phe Ala Met
            260                 265                 270

Ser Trp Tyr Arg Gln Ala Pro Gly Lys Glu Arg Glu Leu Val Ala Arg
        275                 280                 285

Ile Gly Ser Asp Asp Arg Val Thr Tyr Ala Asp Ser Val Lys Gly Arg
290                 295                 300

Phe Thr Ile Ser Arg Asp Asn Ile Lys Arg Thr Ala Gly Leu Gln Met
305                 310                 315                 320

Asn Ser Leu Lys Pro Glu Asp Thr Ala Val Tyr Tyr Cys Asn Ala Gln
                325                 330                 335

Thr Asp Leu Arg Asp Trp Thr Val Arg Glu Tyr Trp Gly Gln Gly Thr
            340                 345                 350

Gln Val Thr Val Ser Ser
        355

<210> SEQ ID NO 56
<211> LENGTH: 1074
<212> TYPE: DNA
<213> ORGANISM: Artificial Sequence
<220> FEATURE:
<223> OTHER INFORMATION: Synthetic polynucleotide

<400> SEQUENCE: 56

```
gaagaggaac tccaggtgat ccagcccgac aagtccgtga gcgtggctgc tggagagagc      60
gccatcctgc actgtaccgt gacctccctg atccctgtgg gacccatcca gtggttcaga     120
ggagctggac ctgcaagaga actgatctac aaccagaagg agggacactt ccctagagtg     180
accacagtga gcgagtccac caagcgggag aacatggact ctccatcag catctccaac      240
atcacccctg ctgacgcagg cacctactat tgcgtgaagt tcaggaaggg cagccctgac     300
accgagttca gtccggcgc tggaaccgag ctgagcgtga gagccaagcc ctcgagctcg      360
agccgtacgg tggctgcacc atctgtcttc atcttcccgc catctgatga gcagttgaaa     420
tctggaactg cctctgttgt gtgcctgctg aataacttct atcccagaga ggccaaagta     480
cagtggaagg tggataacgc cctccaatcg ggtaactccc aggagagtgt cacagagcag     540
gacagcaagg acagcaccta cagcctcagc agcaccctga cgctgagcaa agcagactac     600
gagaaacaca agtctacgc ctgcgaagtc acccatcagg gcctgagctc gcccgtcaca      660
aagagcttca cagggga gtgtaccgtc taggtcagc ccaaggcggc cgctgaggtg         720
cagctggtgg agtctggggg aggcttggta cagcctgggg ggtccctgag actctcctgt     780
gcagcctctg gattcacctt tgacgactat ggcatgagct gggtccgcca ggctccaggg     840
aagtggctgg agtgggtctc agatattagc tggaatggtg gtagcacata ctacgcagac     900
tccgtgaagg gccggttcac catctccaga gacaatgccg agaacacgct gtatctgcaa     960
atgaacagcc tgaaacctga cgacacggcc gtgtattact gtgcgaaaat gggtgaaggg    1020
ggatggggtg caaatgacta ctggggccag gggacccagg tcaccgtgtc ctca          1074
```

<210> SEQ ID NO 57
<211> LENGTH: 358
<212> TYPE: PRT
<213> ORGANISM: Artificial Sequence
<220> FEATURE:
<223> OTHER INFORMATION: Synthetic polypeptide

<400> SEQUENCE: 57

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ser Ser Arg Thr Val Ala Ala Pro Ser
        115                 120                 125

Val Phe Ile Phe Pro Pro Ser Asp Glu Gln Leu Lys Ser Gly Thr Ala
    130                 135                 140
```

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
            165                 170                 175

Val Thr Glu Gln Asp Ser Lys Asp Ser Thr Tyr Ser Leu Ser Ser Thr
        180                 185                 190

Leu Thr Leu Ser Lys Ala Asp Tyr Glu Lys His Lys Val Tyr Ala Cys
            195                 200                 205

Glu Val Thr His Gln Gly Leu Ser Ser Pro Val Thr Lys Ser Phe Asn
210                 215                 220

Arg Gly Glu Cys Thr Val Leu Gly Gln Pro Lys Ala Ala Ala Glu Val
225                 230                 235                 240

Gln Leu Val Glu Ser Gly Gly Gly Leu Val Gln Pro Gly Gly Ser Leu
            245                 250                 255

Arg Leu Ser Cys Ala Ala Ser Gly Phe Thr Phe Asp Asp Tyr Gly Met
            260                 265                 270

Ser Trp Val Arg Gln Ala Pro Gly Lys Trp Leu Glu Trp Val Ser Asp
        275                 280                 285

Ile Ser Trp Asn Gly Gly Ser Thr Tyr Tyr Ala Asp Ser Val Lys Gly
        290                 295                 300

Arg Phe Thr Ile Ser Arg Asp Asn Ala Glu Asn Thr Leu Tyr Leu Gln
305                 310                 315                 320

Met Asn Ser Leu Lys Pro Asp Asp Thr Ala Val Tyr Tyr Cys Ala Lys
            325                 330                 335

Met Gly Glu Gly Gly Trp Gly Ala Asn Asp Tyr Trp Gly Gln Gly Thr
            340                 345                 350

Gln Val Thr Val Ser Ser
            355

<210> SEQ ID NO 58
<211> LENGTH: 1071
<212> TYPE: DNA
<213> ORGANISM: Artificial Sequence
<220> FEATURE:
<223> OTHER INFORMATION: Synthetic polynucleotide

<400> SEQUENCE: 58
gaagaggaac tccaggtgat ccagcccgac aagtccgtga gcgtggctgc tggagagagc      60
gccatcctgc actgtaccgt gacctccctg atccctgtgg acccatcca gtggttcaga     120 ggagctggac ctgcaagaga actgatctac aaccagaagg agggacactt ccctagagtg     180
accacagtga gcgagtccac caagcgggag aacatggact tctccatcag catctccaac     240
atcacccctg ctgacgcagg cacctactat tgcgtgaagt tcaggaaggg cagccctgac     300
accgagttca gtccggcgc tggaaccgag ctgagcgtga gccaagcc ctcgagctcg     360 agccgtacgg tggctgcacc atctgtcttc atcttcccgc catctgatga gcagttgaaa     420
tctggaactg cctctgttgt gtgcctgctg aataacttct atcccagaga ggccaaagta     480
cagtggaagg tggataacgc cctccaatcg ggtaactccc aggagagtgt cacagagcag     540
gacagcaagg acagcaccta cagcctcagc agcaccctga cgctgagcaa agcagactac     600
gagaaacaca agtctacgc ctgcgaagtc acccatcagg gcctgagctc gcccgtcaca     660
aagagcttca caggggaga gtgtaccgtc ctaggtcagc ccaaggcggc cgctgaggtg     720
cagctggtgg agtctggggg aggcttagtg cagcctgggg agtctctgac actctcctgt     780

```
gtagttgctg gaagcatctt cagcttcgcc atgagctggt atcgccaggc tccaggaaaa      840
gagcgcgaat tggtcgcacg tattggttcg gatgatcggg taacctacgc agattccgtg      900
aagggccgat ttaccatctc cagagacaac atcaagcgca cggcgggcct gcagatgaac      960
agcctgaaac ctgaggacac ggccgtctac tactgcaatg cccaaacaga tttgagggat     1020
tggactgtgc gagagtactg gggccagggg acccaggtca ccgtctcctc a              1071
```

<210> SEQ ID NO 59
<211> LENGTH: 357
<212> TYPE: PRT
<213> ORGANISM: Artificial Sequence
<220> FEATURE:
<223> OTHER INFORMATION: Synthetic polypeptide

<400> SEQUENCE: 59

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ser Ser Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220

Arg Gly Glu Cys Thr Val Leu Gly Gln Pro Lys Ala Ala Ala Glu Val
225                 230                 235                 240

Gln Leu Val Glu Ser Gly Gly Gly Leu Val Gln Pro Gly Glu Ser Leu
                245                 250                 255

Thr Leu Ser Cys Val Val Ala Gly Ser Ile Phe Ser Phe Ala Met Ser
            260                 265                 270

Trp Tyr Arg Gln Ala Pro Gly Lys Glu Arg Glu Leu Val Ala Arg Ile
        275                 280                 285

Gly Ser Asp Asp Arg Val Thr Tyr Ala Asp Ser Val Lys Gly Arg Phe
    290                 295                 300

Thr Ile Ser Arg Asp Asn Ile Lys Arg Thr Ala Gly Leu Gln Met Asn
305                 310                 315                 320
```

Ser Leu Lys Pro Glu Asp Thr Ala Val Tyr Tyr Cys Asn Ala Gln Thr
                325                 330                 335

Asp Leu Arg Asp Trp Thr Val Arg Glu Tyr Trp Gly Gln Gly Thr Gln
            340                 345                 350

Val Thr Val Ser Ser
        355

<210> SEQ ID NO 60
<211> LENGTH: 1344
<212> TYPE: DNA
<213> ORGANISM: Artificial Sequence
<220> FEATURE:
<223> OTHER INFORMATION: Synthetic polynucleotide

<400> SEQUENCE: 60

| | |
|---|---:|
| gaggtgcagc tggtggagtc tgggggaggc ttggtccagc ctggggggtc cctgagactc | 60 |
| tcctgtgcag cctctggatt caccttcagt agcagctaca tgagctgggt ccgccaggct | 120 |
| ccagggaagg ggctggagtg ggtctcaggc attaataccg atggtagctt cacacgctac | 180 |
| gcagactccg tgaagggccg attcaccatc tccagagaca atgccaagaa cacgctgtat | 240 |
| cttcaaatga acagcctgaa atctgaggac acggctctgt attactgtgc ggtaggcggc | 300 |
| gggttaggct atggacccag gggcaggga accctggtca ctgtctcctc agcgtcgacc | 360 |
| aagggcccat cggtcttccc gctagcaccc tcctccaaga gcacctctgg ggcacagcg | 420 |
| gccctgggct gcctggtcaa ggactacttc cccgaacctg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaag ctgctggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcggagg agcagtacaa cagcacgtac | 900 |
| cgggtggtca gcgtcctcac cgtcctgcac caggactggc tgaatggcaa ggagtacaag | 960 |
| tgcaaggtct ccaacaaagc cctcggagcc cccatcgaga aaaccatctc caaagccaaa | 1020 |
| gggcagcccc gagaaccaca ggtgtacacc ctgcccccat cccgggatga gctgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atga | 1344 |

<210> SEQ ID NO 61
<211> LENGTH: 447
<212> TYPE: PRT
<213> ORGANISM: Artificial Sequence
<220> FEATURE:
<223> OTHER INFORMATION: Synthetic polypeptide

<400> SEQUENCE: 61

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser
             20                  25                  30

Tyr Met Ser Trp Val Arg Gln Ala Pro Gly Lys Gly Leu Glu Trp Val
         35                  40                  45

Ser Gly Ile Asn Thr Asp Gly Ser Phe Thr Arg Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Leu Tyr Tyr Cys
                 85                  90                  95

Ala Val Gly Gly Gly Leu Gly Tyr Gly Pro Arg Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys
        435                 440                 445

<210> SEQ ID NO 62
<211> LENGTH: 1098
<212> TYPE: DNA
<213> ORGANISM: Artificial Sequence
<220> FEATURE:
<223> OTHER INFORMATION: Synthetic polynucleotide

<400> SEQUENCE: 62
gaggtgcagc tggtggagtc tggaggaggc ttgatccagc ctggggggtc cctgagactc      60
tcctgtgcag cctctgggtt caccttcagt cgccgctgca tggcctggtt ccgccaggct     120
ccagggaagg agcgggagcg ggtcgcaaag ctgctgacca ctagcggtag cacataccctg    180
gcagactccg tgaagggccg attcaccatc tccagagaca attccaagaa cacggtgtat     240
cttcaaatga acagcctgag agccgaggac acggccgtgt attactgtgc ggccgacagc     300
tcgaggaccc ccacctgcac cctggtgacc agcagcggcg cctttcagta ctggggccag     360
ggcaccctgg tcaccgtgtc ctcacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgtaccgt cctaggtcag     720
cccaaggcgg ccgctgaggt gcagctggtg gagtctgggg gaggcttggt acagcctggg     780
gggtccctga gactctcctg tgcagcctct ggattcacct ttgacgacta tgcatgagc     840
tgggtccgcc aggctccagg gaagtggctg gagtgggtct cagatattag ctggaatggt     900
ggtagcacat actacgcaga ctccgtgaag gccggttca ccatctccag agacaatgcc     960
gagaacacgc tgtatctgca aatgaacagc ctgaaacctg acgacacggc cgtgtattac    1020
tgtgcgaaaa tgggtgaagg gggatggggt gcaaatgact actggggcca ggggacccag    1080
gtcaccgtgt cctcataa                                                  1098

<210> SEQ ID NO 63
<211> LENGTH: 365
<212> TYPE: PRT
<213> ORGANISM: Artificial Sequence
<220> FEATURE:
<223> OTHER INFORMATION: Synthetic polypeptide

<400> SEQUENCE: 63

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys Thr Val Leu Gly Gln
225                 230                 235                 240

Pro Lys Ala Ala Ala Glu Val Gln Leu Val Glu Ser Gly Gly Gly Leu
                245                 250                 255

Val Gln Pro Gly Gly Ser Leu Arg Leu Ser Cys Ala Ala Ser Gly Phe
            260                 265                 270

Thr Phe Asp Asp Tyr Gly Met Ser Trp Val Arg Gln Ala Pro Gly Lys
        275                 280                 285

Trp Leu Glu Trp Val Ser Asp Ile Ser Trp Asn Gly Ser Thr Tyr
    290                 295                 300

Tyr Ala Asp Ser Val Lys Gly Arg Phe Thr Ile Ser Arg Asp Asn Ala
305                 310                 315                 320

Glu Asn Thr Leu Tyr Leu Gln Met Asn Ser Leu Lys Pro Asp Asp Thr
                325                 330                 335

Ala Val Tyr Tyr Cys Ala Lys Met Gly Glu Gly Gly Trp Gly Ala Asn
            340                 345                 350

Asp Tyr Trp Gly Gln Gly Thr Gln Val Thr Val Ser Ser
        355                 360                 365

<210> SEQ ID NO 64
<211> LENGTH: 1095
<212> TYPE: DNA
<213> ORGANISM: Artificial Sequence
<220> FEATURE:
<223> OTHER INFORMATION: Synthetic polynucleotide

<400> SEQUENCE: 64
gaggtgcagc tggtggagtc tggaggaggc ttgatccagc ctggggggtc cctgagactc      60
tcctgtgcag cctctgggtt caccttcagt cgccgctgca tggcctggtt ccgccaggct     120
ccagggaagg agcgggagcg ggtcgcaaag ctgctgacca ctagcggtag cacatacctg     180
gcagactccg tgaagggccg attcaccatc tccagagaca attccaagaa cacggtgtat     240
cttcaaatga acagcctgag agccgaggac acggccgtgt attactgtgc ggccgacagc     300
ttcgaggacc ccacctgcac cctggtgacc agcagcggcg cctttcagta ctggggccag     360
ggcaccctgg tcaccgtgtc ctcacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540

-continued

```
caggagagtg tcacagagca ggacagcaag gacagcacct acagcctcag cagcaccctg      600
acgctgagca aagcagacta cgagaaacac aaagtctacg cctgcgaagt cacccatcag      660
ggcctgagct cgcccgtcac aaagagcttc aacaggggag agtgtaccgt cctaggtcag      720
cccaaggcgg ccgctgaggt gcagctggtg gagtctgggg gaggcttagt gcagcctggg      780
gagtctctga cactctcctg tgtagttgct ggaagcatct tcagcttcgc catgagctgg      840
tatcgccagg ctccaggaaa agagcgcgaa ttggtcgcac gtattggttc ggatgatcgg      900
gtaacctacg cagattccgt gaagggccga tttaccatct ccagagacaa catcaagcgc      960
acggcgggcc tgcagatgaa cagcctgaaa cctgaggaca cggccgtcta ctactgcaat     1020
gcccaaacag atttgaggga ttggactgtg cgagagtact ggggccaggg gacccaggtc     1080
accgtctcct cataa                                                      1095
```

<210> SEQ ID NO 65
<211> LENGTH: 364
<212> TYPE: PRT
<213> ORGANISM: Artificial Sequence
<220> FEATURE:
<223> OTHER INFORMATION: Synthetic polypeptide

<400> SEQUENCE: 65

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys Thr Val Leu Gly Gln
225                 230                 235                 240

Pro Lys Ala Ala Ala Glu Val Gln Leu Val Glu Ser Gly Gly Gly Leu
                245                 250                 255
```

Val Gln Pro Gly Glu Ser Leu Thr Leu Ser Cys Val Val Ala Gly Ser
            260                 265                 270

Ile Phe Ser Phe Ala Met Ser Trp Tyr Arg Gln Ala Pro Gly Lys Glu
        275                 280                 285

Arg Glu Leu Val Ala Arg Ile Gly Ser Asp Asp Arg Val Thr Tyr Ala
    290                 295                 300

Asp Ser Val Lys Gly Arg Phe Thr Ile Ser Arg Asp Asn Ile Lys Arg
305                 310                 315                 320

Thr Ala Gly Leu Gln Met Asn Ser Leu Lys Pro Glu Asp Thr Ala Val
                325                 330                 335

Tyr Tyr Cys Asn Ala Gln Thr Asp Leu Arg Asp Trp Thr Val Arg Glu
            340                 345                 350

Tyr Trp Gly Gln Gly Thr Gln Val Thr Val Ser Ser
        355                 360

<210> SEQ ID NO 66
<211> LENGTH: 1362
<212> TYPE: DNA
<213> ORGANISM: Artificial Sequence
<220> FEATURE:
<223> OTHER INFORMATION: Synthetic polynucleotide

<400> SEQUENCE: 66
caggtgcagc tggtgcagtc tgggggagga ttggtgcagg ctgggggctc tctgagactc      60
tcctgtgcag cctctggacg caccttcagt agttatgcca tggcctggtt ccgccaggct     120
ccagggaagg agcgtgagtt tgtagcagct attagctgga gtggtgcaaa catatacgtt     180
gcagactccg tgaagggccg attcaccatc tccagagaca acgccaagga cacggtgtat     240
ctgcaaatga acagcctgaa acctgaggac acggccgttt attactgtgc agtaaagctc     300
ggtttcgcac tgtagaaga aaggcagtat gactactggg gccaggggac ccaggtcacc     360
gtctcctcag cgtcgaccaa gggcccatcg gtcttcccgc tagcaccctc ctccaagagc     420
acctctgggg gcacagcggc cctgggctgc ctggtcaagg actacttccc cgaacctgtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt ggacaagaaa     660
gttgagccca aatcttgtga caaaactcac acatgcccac cgtgcccagc acctgaagct     720
gctgggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg ggtggtcagc gtcctcaccg tcctgcacca ggactggctg     960
aatggcaagg agtacaagtg caaggtctcc aacaaagccc tcggagcccc catcgagaaa    1020
accatctcca aagccaaagg gcagccccga gaaccacagg tgtacaccct gcccccatcc    1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaat ga                       1362

<210> SEQ ID NO 67

```
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 67
```

| | | | | | | | | | | | | | | | |
|---|---|---|---|---|---|---|---|---|---|---|---|---|---|---|---|
| Gln | Val | Gln | Leu | Val | Gln | Ser | Gly | Gly | Gly | Leu | Val | Gln | Ala | Gly | Gly |
| 1 | | | | 5 | | | | | 10 | | | | | 15 | |
| Ser | Leu | Arg | Leu | Ser | Cys | Ala | Ala | Ser | Gly | Arg | Thr | Phe | Ser | Ser | Tyr |
| | | | 20 | | | | | 25 | | | | | 30 | | |
| Ala | Met | Ala | Trp | Phe | Arg | Gln | Ala | Pro | Gly | Lys | Glu | Arg | Glu | Phe | Val |
| | | 35 | | | | | 40 | | | | | 45 | | | |
| Ala | Ala | Ile | Ser | Trp | Ser | Gly | Ala | Asn | Ile | Tyr | Val | Ala | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Asp | Thr | Val | Tyr |
| 65 | | | | | 70 | | | | | 75 | | | | | 80 |
| Leu | Gln | Met | Asn | Ser | Leu | Lys | Pro | Glu | Asp | Thr | Ala | Val | Tyr | Tyr | Cys |
| | | | | 85 | | | | | 90 | | | | | 95 | |
| Ala | Val | Lys | Leu | Gly | Phe | Ala | Pro | Val | Glu | Glu | Arg | Gln | Tyr | Asp | Tyr |
| | | | 100 | | | | | 105 | | | | | 110 | | |
| Trp | Gly | Gln | Gly | Thr | Gln | Val | Thr | Val | Ser | Ser | Ala | Ser | Thr | Lys | Gly |
| | | | 115 | | | | | 120 | | | | | 125 | | |
| Pro | Ser | Val | Phe | Pro | Leu | Ala | Pro | Ser | Ser | Lys | Ser | Thr | Ser | Gly | Gly |
| | | 130 | | | | | 135 | | | | | 140 | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | | 195 | | | | | 200 | | | | | 205 | | |
| Asn | His | Lys | Pro | Ser | Asn | Thr | Lys | Val | Asp | Lys | Lys | Val | Glu | Pro | Lys |
| | | 210 | | | | | 215 | | | | | 220 | | | |
| Ser | Cys | Asp | Lys | Thr | His | Thr | Cys | Pro | Pro | Cys | Pro | Ala | Pro | Glu | Ala |
| 225 | | | | | 230 | | | | | 235 | | | | | 240 |
| Ala | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | | 275 | | | | | 280 | | | | | 285 | | |
| Glu | Val | His | Asn | Ala | Lys | Thr | Lys | Pro | Arg | Glu | Glu | Gln | Tyr | Asn | Ser |
| | | | 290 | | | | | 295 | | | | | 300 | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Gly | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Ser | Arg | Asp | Glu | Leu | Thr | Lys | Asn | Gln |
| | | | 355 | | | | | 360 | | | | | 365 | | |
| Val | Ser | Leu | Thr | Cys | Leu | Val | Lys | Gly | Phe | Tyr | Pro | Ser | Asp | Ile | Ala |
| | | | 370 | | | | | 375 | | | | | 380 | | |

```
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450
```

<210> SEQ ID NO 68
<211> LENGTH: 1368
<212> TYPE: DNA
<213> ORGANISM: Artificial Sequence
<220> FEATURE:
<223> OTHER INFORMATION: Synthetic polynucleotide

<400> SEQUENCE: 68

```
gatgtgcagc tgcaggcktc tggaggaggc tcggtgcagg cgggagggtc tctgaggctc      60
tcctgtgcag cggatgcata catctacagt aggaaccgtc tggcctggtt ccgccggtct     120
ccaggaaagg accgcgaggg agtcgcaaca atgtgtgacg aaacacata ctatagcgac      180
tccgcgaagg gccgattcac catctcccaa gacaacgcca agaacgagct aattctgcaa     240
atgagcagcc tgagacctga ggacactgcc acgtacttct gtgcaggccg accgtcttcc     300
attgaaaatt gtggtagcct cagtctgcat gattataact tctggggcca agggacccag     360
gtcaccgtct cctcagcgtc gaccaagggc ccatcggtct tccgctagc accctcctcc      420
aagagcacct ctgggggcac agcggccctg ggctgcctgg tcaaggacta cttccccgaa     480
cctgtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagaaagttg agcccaaatc ttgtgacaaa actcacacat gcccaccgtg cccagcacct     720
gaagctgctg ggggaccgtc agtcttcctc ttcccccca aacccaagga caccctcatg      780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgggtg gtcagcgtcc tcaccgtcct gcaccaggac     960
tggctgaatg gcaaggagta caagtgcaag gtctccaaca aagccctcgg agcccccatc    1020
gagaaaacca tctccaaagc caagggcag cccgagaac cacaggtgta ccctgccc       1080
ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaatga                 1368
```

<210> SEQ ID NO 69
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 69

Asp Val Gln Leu Gln Ala Ser Gly Gly Gly Ser Val Gln Ala Gly Gly
1               5                   10                  15

Ser Leu Arg Leu Ser Cys Ala Ala Asp Ala Tyr Ile Tyr Ser Arg Asn
            20                  25                  30

Arg Leu Ala Trp Phe Arg Arg Ser Pro Gly Lys Asp Arg Glu Gly Val
        35                  40                  45

Ala Thr Met Cys Asp Gly Asn Thr Tyr Tyr Ser Asp Ser Ala Lys Gly
    50                  55                  60

Arg Phe Thr Ile Ser Gln Asp Asn Ala Lys Asn Glu Leu Ile Leu Gln
65                  70                  75                  80

Met Ser Ser Leu Arg Pro Glu Asp Thr Ala Thr Tyr Phe Cys Ala Gly
                85                  90                  95

Arg Pro Ser Ser Ile Glu Asn Cys Gly Ser Leu Ser Leu His Asp Tyr
            100                 105                 110

Asn Phe Trp Gly Gln Gly Thr Gln Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Gly Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

```
Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450             455
```